US011266636B2

(12) United States Patent
Bachhav et al.

(10) Patent No.: US 11,266,636 B2
(45) Date of Patent: Mar. 8, 2022

(54) MALEATE SALT OF THE FREE BASE OF N-[5-(AMINOSULFONYL)-4-METHYL-1,3-THIAZOL-2-YL]-N-METHYL-2-[4-(2-PYRIDINYL)-PHENYL]-ACETAMIDE, PHARMACEUTICAL FORMULATIONS, METHODS OF MANUFACTURE AND USES THEREOF FOR THE TREATMENT OF HERPES VIRUSES

(71) Applicant: AICURIS ANTI-INFECTIVE CURES GMBH, Wuppertal (DE)

(72) Inventors: Yogeshwar Bachhav, Mumbai (IN); Wilfried Schwab, Werder (DE); Alexander Birkmann, Wuppertal (DE); Susanne Bonsmann, Cologne (DE); Thomas Goldner, Wuppertal (DE)

(73) Assignee: AICURIS GMBH & CO. KG, Wuppertal (DE)

( * ) Notice: Subject to any disclaimer, the term of this patent is extended or adjusted under 35 U.S.C. 154(b) by 48 days.

(21) Appl. No.: 16/464,189

(22) PCT Filed: Nov. 28, 2017

(86) PCT No.: PCT/EP2017/080695
§ 371 (c)(1),
(2) Date: May 24, 2019

(87) PCT Pub. No.: WO2018/096177
PCT Pub. Date: May 31, 2018

(65) Prior Publication Data
US 2020/0289485 A1 Sep. 17, 2020

(30) Foreign Application Priority Data
Nov. 28, 2016 (EP) .................... 16201009

(51) Int. Cl.
A61K 31/4439 (2006.01)
A61K 9/00 (2006.01)
A61K 45/06 (2006.01)
C07D 417/12 (2006.01)

(52) U.S. Cl.
CPC ........ A61K 31/4439 (2013.01); A61K 9/0014 (2013.01); A61K 45/06 (2013.01); C07D 417/12 (2013.01)

(58) Field of Classification Search
CPC .............. C07D 417/12; A61K 31/4439; A61K 9/0014; A61K 45/06
See application file for complete search history.

(56) References Cited

U.S. PATENT DOCUMENTS

| 7,105,553 | B2 | 9/2006 | Fischer et al. |  |
|---|---|---|---|---|
| 8,784,887 | B2* | 7/2014 | Laich | ..... A61K 31/18 424/465 |
| 9,119,786 | B2 | 9/2015 | Schwab et al. |  |
| 9,340,535 | B2 | 5/2016 | Schwab et al. |  |
| 9,592,225 | B2 | 3/2017 | Schwab et al. |  |
| 9,889,124 | B2 | 2/2018 | Schwab et al. |  |
| 10,137,117 | B2 | 11/2018 | Schwab et al. |  |
| 11,021,474 | B2* | 6/2021 | Bachhav | ................ A61P 31/22 |
| 2004/0006076 | A1 | 1/2004 | Fischer et al. |  |
| 2014/0065224 | A1 | 3/2014 | Schwab et al. |  |
| 2014/0221433 | A1 | 8/2014 | Schwab et al. |  |
| 2015/0366849 | A1 | 12/2015 | Schwab et al. |  |
| 2016/0008341 | A1 | 1/2016 | Schwab et al. |  |
| 2017/0348297 | A1 | 12/2017 | Schwab et al. |  |
| 2020/0123145 | A1* | 4/2020 | Bachhav | .............. C07D 417/12 |
| 2021/0269429 | A1* | 9/2021 | Bachhav | ................ A61P 31/22 |

FOREIGN PATENT DOCUMENTS

| EP | 2598502 A1 | 6/2013 |
|---|---|---|
| WO | 0147904 A1 | 7/2001 |
| WO | 2013045479 A1 | 4/2013 |

OTHER PUBLICATIONS

Rodriguez-Spong et al., "General Principles, etc.," Adv. Drug Delivery Reviews 56, 241-274. (Year: 2004).*
Guillory (in Brittain ed.) Polymorphism in Pharmaceutical Solids NY:Marcel Dekker, Inc., 1-2, 183-226. (Year: 1999).*
Verbeeck; Eur. J. Pharm. Sci. 2006, 28, 1-6. doi:10.1016/j.ejps.2005.12.001 (Year: 2006).*
Wald; N. Engl. J. Med. 2014, 370, 201-210. DOI: 10.1056/NEJMoa1301150 (Year: 2014).*
"Background and Legal Framework of the European Pharmacopoeia", Downloaded Oct. 14, 2021 at: https://www.edqm.eu/en/European-Pharmacopoeia-Background-Mission (Year: 2021).*
"Usp quality standards for compounding", Downloaded Oct. 14, 2021 at https://www.usp.org/sites/default/files/usp/document/about/usp-quality-standards-for-compounding.pdf (Year: 2021).*
ICH Guideline Q1B "Stability Testing: Photostability Testing of New Drug Substances and Products" Nov. 6, 1996. Downloaded on Oct. 13, 2021 From https://database.ich.org/sites/default/files/Q1B%20Guideline.pdf (Year: 1996).*
International Search Report for PCT/EP2017/080695 dated Feb. 21, 2018.

* cited by examiner

Primary Examiner — Daniel R Carcanague
(74) Attorney, Agent, or Firm — Millen, White, Zelano & Branigan, PC; Ryan Pool

(57) ABSTRACT

The present invention relates to the field of anti-viral active agents, particularly to salts, more particularly to a maleate salt of the free base of N-[5-(aminosulfonyl)-4-methyl-1,3-thiazol-2-yl]-N-methyl-2-[4-(2-pyridinyl)-phenyl]-acetamide, to pharmaceutical formulations thereof as well as to methods for the production of these salts. The present invention also relates to the use of theses salts and of respective pharmaceutical formulations thereof in methods of treatment and/or prevention of human herpes simplex virus infections, particularly infections caused by HSV-1 and HSV-2.

15 Claims, 47 Drawing Sheets

FIG. 1:

| Identification code | mo_P07102ACE1101_0m |
|---|---|
| Empirical formula | $C_{22} H_{22} N_4 O_7 S_2$ |
| Formula weight | 518.55 |
| Temperature | 100(2) K |
| Wavelength | 0.71073 Å |
| Crystal system | Monoclinic |
| Space group | $C2/c$ |
| Unit cell dimensions | a = 36.307(2) Å, $\alpha$ = 90°<br>b = 4.6551(3) Å, $\beta$ = 115.0135(17)°<br>c = 29.3265(18) Å, $\gamma$ = 90° |
| Volume | 4491.7(5) Å$^3$ |
| Z | 8 |
| Density (calculated) | 1.534 Mg / m$^3$ |
| Absorption coefficient | 0.291 mm$^{-1}$ |
| F(000) | 2160 |
| Crystal size | 0.40 x 0.02 x 0.01 mm$^3$ |
| Theta range for data collection | 2.296 to 30.608° |
| Index ranges | $-52 \leq h \leq 38, -6 \leq k \leq 6, -41 \leq l \leq 41$ |
| Reflections collected | 26525 |
| Obs. Independent reflections | 5414 [R(int) = 0.0388] |
| Completeness to theta = 30.608° | 99.0 % |
| Absorption correction | Multi-scan |
| Max. and min. transmission | 0.997 and 0.914 |
| Refinement method | Full-matrix least-squares on F$^2$ |
| Data / restraints / parameters | 6853 / 0 / 335 |
| Goodness-of-fit on F2 | 1.028 |
| Final R indices [I>2sigma(I)] | R1 = 0.0377, wR2 = 0.0882 |
| R indices (all data) | R1 = 0.0561, wR2 = 0.0961 |
| Largest diff. peak and hole | 0.443 and -0.423 e·Å$^{-3}$ |

FIG. 10:

| 2θ (°) | d (Å) | Rel. Int. % | 2θ (°) | d (Å) | Rel. Int. % | 2θ (°) | d (Å) | Rel. Int. % |
|---|---|---|---|---|---|---|---|---|
| 5,3 | 16,70 | 14,2 | 23,9 | 3,73 | 26 | 31,1 | 2,88 | 10,9 |
| 6,6 | 13,47 | 36,9 | 24,1 | 3,68 | 14,5 | 31,3 | 2,85 | 6,2 |
| 9,9 | 8,91 | 27,9 | 24,3 | 3,67 | 12,6 | 31,7 | 2,82 | 8,1 |
| 10,1 | 8,75 | 65,2 | 24,5 | 3,63 | 48,8 | 31,9 | 2,80 | 9,5 |
| 10,7 | 8,25 | 9,5 | 24,8 | 3,59 | 9,9 | 32,2 | 2,78 | 10,6 |
| 11,9 | 7,41 | 16 | 25,0 | 3,56 | 23,4 | 32,6 | 2,74 | 4 |
| 13,0 | 6,80 | 41,6 | 25,2 | 3,53 | 8,5 | 32,9 | 2,72 | 7,1 |
| 13,2 | 6,70 | 100 | 25,7 | 3,47 | 18,8 | 33,2 | 2,69 | 6,4 |
| 15,9 | 5,56 | 25,5 | 26,1 | 3,41 | 70,8 | 33,5 | 2,67 | 17,4 |
| 16,2 | 5,45 | 34,3 | 26,4 | 3,37 | 19,2 | 33,9 | 2,64 | 10,9 |
| 17,5 | 5,06 | 6,7 | 26,6 | 3,34 | 32 | 34,4 | 2,61 | 7 |
| 18,1 | 4,89 | 31,5 | 26,8 | 3,33 | 31,3 | 34,7 | 2,58 | 8,4 |
| 19,1 | 4,65 | 33,9 | 27,0 | 3,30 | 17 | 35,1 | 2,56 | 4,7 |
| 19,5 | 4,55 | 32,2 | 27,5 | 3,24 | 10 | 35,3 | 2,54 | 4 |
| 19,9 | 4,46 | 83,3 | 28,0 | 3,19 | 11,6 | 35,5 | 2,53 | 3,4 |
| 20,2 | 4,39 | 45,9 | 28,2 | 3,16 | 8,1 | 35,8 | 2,50 | 5,1 |
| 20,5 | 4,34 | 43,3 | 28,6 | 3,12 | 44,4 | 36,2 | 2,48 | 7,7 |
| 20,9 | 4,24 | 22,8 | 28,8 | 3,09 | 6,6 | 36,5 | 2,46 | 5,2 |
| 21,3 | 4,17 | 70 | 29,1 | 3,07 | 9,8 | 36,9 | 2,43 | 10,3 |
| 21,6 | 4,12 | 10,7 | 29,3 | 3,05 | 13,2 | 37,8 | 2,38 | 7,4 |
| 22,0 | 4,04 | 8,7 | 29,5 | 3,03 | 22,5 | 38,3 | 2,35 | 9,1 |
| 22,3 | 3,99 | 16,8 | 29,8 | 3,00 | 5,3 | 38,5 | 2,34 | 11,3 |
| 22,5 | 3,94 | 78,2 | 30,1 | 2,97 | 5,2 | 38,7 | 2,32 | 8,4 |
| 22,8 | 3,89 | 13 | 30,3 | 2,95 | 11,6 | 39,3 | 2,29 | 8,1 |
| 23,2 | 3,83 | 42,6 | 30,7 | 2,91 | 10,5 | 39,6 | 2,27 | 7,8 |
| 23,7 | 3,75 | 15 | 30,8 | 2,90 | 10,6 | | | |

FIG. 13:

| (ppm) | Description | J (Hz) |
|---|---|---|
| 2.48 | s, 3H | - |
| 3.72 | s, 3H | - |
| 4.24 | s, 2H | - |
| 6.27 | s, 2H | - |
| 7.38 | m, 1H | - |
| 7.40 | d, 2H | 8.4 |
| 7.64 | s, 2H | - |
| 7.91 | td, 1H | 7.9, 1.8 |
| 7.98 | d, 1H | 8.0 |
| 8.07 | d, 2H | 8.3 |
| 8.68 | dm, 1H | 4.8 |

FIG. 15:

| (ppm) | (ppm) |
|---|---|
| 16.6 | 137.5 |
| 34.8 | 138.1 |
| 120.8 | 148.6 |
| 123.1 | 149.7 |
| 127.1 | 156.1 |
| 128.8 | 158.9 |
| 130.6 | 167.2 |
| 130.8 | 172.2 |
| 135.7 | |

FIG. 17:

| Wavenumber (cm$^{-1}$) | Peak shape | Wavenumber (cm$^{-1}$) | Peak shape |
|---|---|---|---|
| 3338.8 | b me | 1155.0 | s st |
| 3237.5 | b me | 1133.0 | s we |
| 3082.6 | b we | 1097.4 | b we |
| 3057.8 | b we | 1075.8 | b st |
| 2124.2 | b we | 1011.0 | s we |
| 2084.0 | b we | 996.6 | s we |
| 1704.5 | s we | 967.0 | b me |
| 1656.8 | s me | 940.1 | s we |
| 1618.8 | s me | 894.4 | s me |
| 1556.2 | b we | 876.4 | s me |
| 1521.2 | b we | 858.6 | s st |
| 1473.1 | b me | 827.3 | s we |
| 1451.4 | s st | 805.1 | b we |
| 1413.5 | s st | 782.9 | s st |
| 1379.0 | s we | 767.8 | s st |
| 1354.4 | s me | 739.5 | s we |
| 1329.6 | s st | 725.9 | s me |
| 1310.1 | s st | 686.7 | s me |
| 1266.4 | s we | 644.3 | s st |
| 1250.1 | b we | 638.0 | s st |
| 1211.0 | b we | 614.2 | s me |
| 1195.4 | b we | 605.8 | s me |
| 1173.4 | s we | | |

| Wavelenght (nm) | Absorbance |
|---|---|
| 248 | 0.205 |
| 281 | 0.271 |
| 730 | 0.032 |
| 893 | 0.058 |

FIG. 21:

| m/z | Fragment |
|---|---|
| 401.1 | Pritelivir free base fragment |
| 281.0 | - |
| 115.0 | Maleate fragment |

FIG. 47:

| Time [h] | Mean concentration [mg/L] | | | | | |
|---|---|---|---|---|---|---|
| | Mono ethane | Maleate salt | Mono benzene | Hemi ethane | Free base prit. | Mesylate salt |
| FaSSGF | | | | | | |
| 0 | 393 | 128 | 97.8 | 211 | 206 | 123 |
| 30 | 137 | 53.8 | 42.8 | 104 | 107 | 145 |
| 60 | 119 | 65.6 | 34.9 | 95.0$^a$ | 101 | 145 |
| 120 | 99.0 | 58.7 | 33.7$^a$ | 94.0 | 94.7 | 111 |
| FeSSIF | | | | | | |
| 0 | 5.92 | 5.90 | 9.18 | 5.92 | 0.700 | 3.08 |
| 30 | 48.7 | 24.7 | 19.9 | 29.8 | 0.516 | 2.27 |
| 60 | 13.3 | 19.0 | 18.7 | 22.1 | 0.538 | 3.32 |
| 120 | 44.9 | 17.5 | 17.5 | 21.5 | 0.516 | 24.9 |
| FaSSIF | | | | | | |
| 0 | 19.3 | 17.9 | 3.68 | 18.9 | 2.10 | 6.68 |
| 30 | 4.61 | 3.25 | 2.00 | 6.51 | 1.48 | 4.08 |
| 60 | 3.63 | 2.27 | 1.56 | 1.84 | 1.27 | 1.94 |
| 120 | 1.58 | 1.56 | 1.49 | 1.46 | 1.19 | 1.30 | a: Mean of n=2

FIG. 48:

| Compound | concentration [mg/mL] | pH |
|---|---|---|
| Free base pritelivir | 0.00130 | 6.56 |
| Mesylate salt | 1.20 | 2.80 |
| Sulfate salt | 0.175 | 3.48 |
| Mono ethane sulfonate | 0.606 | 3.03 |
| Maleate salt | 0.483 | 3.16 |
| Mono benzene sulfonate | 0.229 | 3.69 |
| Hemi ethane-1,2-disulfonate | 0.434 | 3.20 |

FIG. 49:

| Form of pritelivir | Solubility [mg/mL] | | | | |
|---|---|---|---|---|---|
| | Captisol® | HP-beta CD | EtOH | PG | PEG |
| free base | 1.79 | 1.91 | 0.197 | 2.09 | 89.6 |
| mesylate salt | 34.9 | 37.7 | 0.485 | 11.6 | 8.26 |
| sulfate salt | 37.6 | 24.3 | 0.245 | 12.5 | 15.2 |
| mono ethane sulfonate | 26.7 | 23.5 | 0.290 | 5.96 | 6.74 |
| maleate salt | 24.5 | 24.1 | 0.439 | 5.23 | 32.2 |
| mono benzene sulfonate salt | 18.5 | 21.0 | 0.333 | 3.03 | 6.79 |
| hemi ethane-1,2-disulfonate salt | 34.2 | 32.7 | 0.285 | 0.769 | 8.48 |

Captisol: 30% captisol, HP-beta CD: 30% HP-β-cyclodextrin, EtOH: ethanol, PG: propylene glycol, PEG: polyethylene glycol

FIG. 50:

| Vehicle | % Recovery | | | | | | |
|---|---|---|---|---|---|---|---|
| | Free base | Mesylate | Sulfate | Mono ethane | Maleate salt | Mono benz. | Hemi ethane |
| Captisol® | 99.0 | 95.8 | 105 | 100 | 103 | 107 | 103 |
| HP-beta CD | 97.9 | 107 | 106 | 113 | 117 | 105 | 102 |
| Ethanol | 87.6 | 93.4 | 95.2 | 96.6 | 94.4 | 94.5 | 92.7 |
| PEG | 88.2 | 118 | 111 | 109 | 109 | 98.1 | 96.4 |
| PG | 81.7 | 102 | 106 | 119 | 99.8 | 103 | 93.9 |

Captisol: 30% captisol, HP-beta CD: 30% HP-β-cyclodextrin, PG: propylene glycol, PEG: polyethylene glycol

FIG. 51:

| Vehicle | % Recovery | | | | | | |
|---|---|---|---|---|---|---|---|
| | Free base | Mesylate salt | Sulfate salt | Mono ethane | Maleate salt | Mono benz. | Hemi ethane |
| HP-beta CD | 88.9 | 102 | 104 | 109 | 103 | 99.9 | 96.2 |
| Captisol® | 103 | 97.1 | 98.7 | 101 | 103 | 106 | 105 |
| Ethanol | 21.3 | 99.7 | 101 | 105 | 96.8 | 93.5 | 92.5 |
| PEG | 78.3 | 94.4 | 113 | 80.1 | 87.1 | 74.7 | 75.4 |
| PG | 0.00 | 96.4 | 96.2 | 120 | 96.1 | 102 | 98.9 |

Captisol: 30% captisol, HP-beta CD: 30% HP-β-cyclodextrin, PG: propylene glycol, PEG: polyethylene glycol

FIG. 52:

| Compound | Free base pritelivir % Peak Area (280 nm) | |
|---|---|---|
| | dark control | irradiated |
| free base of pritelivir | 99.8 | 99.6 |
| mesylate salt | 100 | 97.4 |
| sulfate salt | 99.9 | 98.1 |
| mono ethane sulfonate salt | 100 | 100 |
| maleate salt | 99.2 | 98.7 |
| mono benzene sulfonate salt | 99.6 | 99.6 |
| hemi ethane-1,2-disulfonate salt | 100 | 99.9 |

FIG. 53:

| Compound | Free base of pritelivir % Total Peak Area (280 nm) | |
|---|---|---|
| | dark control | irradiated |
| free base of pritelivir | 98.0[a] | 10.7 |
| mesylate salt | 98.7[a] | 7.20 |
| sulfate salt | 98.0 | 6.67 |
| mono ethane sulfonate salt | 98.1 | 8.05 |
| maleate salt | 97.4 | 71.5 |
| mono benzene sulfonate salt | 97.9 | 8.11 |
| hemi ethane-1,2-disulfonate salt | 98.2 | 11.9 | a: mean of n=2

MALEATE SALT OF THE FREE BASE OF N-[5-(AMINOSULFONYL)-4-METHYL-1,3-THIAZOL-2-YL]-N-METHYL-2-[4-(2-PYRIDINYL)-PHENYL]-ACETAMIDE, PHARMACEUTICAL FORMULATIONS, METHODS OF MANUFACTURE AND USES THEREOF FOR THE TREATMENT OF HERPES VIRUSES

FIELD OF THE INVENTION

The present invention relates to the field of anti-viral active agents, particularly to salts, more particularly to a maleate salt of the free base of N-[5-(aminosulfonyl)-4-methyl-1,3-thiazol-2-yl]-N-methyl-2-[4-(2-pyridinyl)-phenyl]-acetamide (said acetamide compound may hereinafter also being referred to as "pritelivir"), to pharmaceutical formulations thereof as well as to methods for the production of these salts. The present invention also relates to the use of said salts, particularly of the maleate salt and respective pharmaceutical formulations thereof in the treatment and/or prevention of human herpes simplex virus infections.

BACKGROUND

N-[5-(aminosulfonyl)-4-methyl-1,3-thiazol-2-yl]-N-methyl-2-[4-(2-pyridinyl)-phenyl]-acetamide (i.e. "pritelivir"), the free base and mesylate salts thereof are known anti-viral compounds used in the treatment of herpes simplex viruses (Herpes Simplex Virus 1 and 2, respectively; hereinafter abbreviated as HSV-1 and HSV-2) as e.g. disclosed in WO 2006/103011 A1.

WO 01/47904 A1 describes thiazolyl amide derivatives, a method for producing them and their uses as medicaments, especially as antiviral medicaments.

WO 03/000259 A1 describes the topical application of substituted thiazolyl amides in the treatment of herpes infections in humans, preparations suitable for the topical application and methods for the production thereof.

The aforementioned WO 2006/103011 A1 describes pharmaceutical preparations for oral administration containing N-[5-(aminosulfonyl)-4-methyl-1,3-thiazol-2-yl]-N-methyl-2-[4-(2-pyridinyl)-phenyl]-acetamide or hydrates or solvates thereof, as well as an acid thereof. Said document also concerns a method of producing said preparations, as well as uses thereof for treating/preventing diseases mediated by herpesviruses, in particular diseases mediated by Herpesvirus simplex.

WO 2013/045491 A1 describes crystalline mesylate monohydrate salts of N-[5-(aminosulfonyl)-4-methyl-1,3-thiazol-2-yl]-N-methyl-2-[4-(2-pyridinyl)-phenyl]-acetamide in a definite particle size distribution and with a specific surface area range, which demonstrates increased long-term stability and release kinetics from pharmaceutical compositions thereof. Accordingly, also pharmaceutical compositions containing said crystalline mesylate monohydrate salts of N-[5-(aminosulfonyl)-4-methyl-1,3-thiazol-2-yl]-N-methyl-2-[4-(2-pyridinyl)-phenyl]-acetamide are described therein.

Likewise, EP 2 598 502 A1 describes the crystalline mono mesylate monohydrate salt of N-[5-(aminosulfonyl)-4-methyl-1,3-thiazol-2-yl]-N-methyl-2-[4-(2-pyridinyl)phenyl]-acetamide in a definite particle size distribution and a specific surface area range, which has demonstrated increased long term stability and release kinetics from pharmaceutical compositions, as well as to pharmaceutical compositions containing said N-[5-(aminosulfonyl)-4-methyl-1,3-thiazol-2-yl]-N-methyl-2-[4-(2-pyridinyl)phenyl]acetamide mono mesylate monohydrate having the afore-mentioned particle size distribution and specific surface area range.

WO 2013/045479 A1 describes an improved and shortened synthesis process of N-[5-(aminosulfonyl)-4-methyl-1,3-thiazol-2-yl]-N-methyl-2-[4-(2-pyridinyl)-phenyl]-acetamide and the mesylate salt thereof by using boronic acid derivatives or borolane reagents while avoiding toxic organic tin compounds. Moreover, also the crystalline mesylate monohydrate salt of N-[5-(aminosulfonyl)-4-methyl-1,3-thiazol-2-yl]-N-methyl-2-[4-(2-pyridinyl)-phenyl]-acetamide is described therein with increased long-term stability and release kinetics from pharmaceutical compositions thereof.

Said pritelivir is an innovative, highly active and specific inhibitor of herpes simplex virus (HSV) infections. As a compound derived from the chemical class of thiazolylamides, pritelivir is active against both types of herpes simplex virus causing labial and genital herpes, respectively, and retains activity against viruses which have become resistant to marketed drugs. Pritelivir has a mode of action that is distinct from other antiviral agents currently in use for treatment of HSV infections (i.e., the nucleoside analogues acyclovir and its prodrug valacyclovir as well as famciclovir, the prodrug of penciclovir). Whereas nucleoside analogs terminate ongoing DNA chain elongation through inhibition of viral DNA polymerase, pritelivir prevents de novo synthesis of virus DNA through inhibition of the helicase-primase complex. In addition, it does not require activation within an HSV infected cell by viral thymidine kinase and therefore, is also protective to uninfected cells.

HSV-1 and/or HSV-2 infections are the cause of diseases such as labial herpes (e.g. clinically manifested as cold sores which are mainly due to infections with HSV-1), genital herpes (mainly due to HSV-2 infections), but may rarely also cause severe diseases, such as keratitis and encephalitis. The viruses are ubiquitously distributed throughout the world. A well-known drug used in the treatment of herpes simplex infections is acyclovir (i.e. 2-Amino-1,9-dihydro-9-((2-hydroxyethoxy)methyl)-6H-purin-6-one), which is a specific inhibitor of the viral DNA polymerase.

Thus, herpes simplex viruses are widespread in the human population (seroprevalence up to 100%, depending on geographic area and subpopulation), and are divided into herpes simplex virus type 1 (HSV-1) and type 2 (HSV-2). Infections lead to lifelong persistence of the virus, with frequent and sometimes painful recurrences. While HSV-1 predominantly causes oral lesions (cold sores), HSV-2 manifests in the genital region and is mainly sexually transmitted. In immunocompromised patients, HSV can lead to serious complications. In the immune competent, the negative stigma associated with genital herpes and visible facial lesions might cause psychological distress.

According to the WHO an estimated 3.7 billion people worldwide under the age of 50, or 67% of the population, were infected with HSV-1 in 2012. Prevalence of the infection was estimated highest in Africa (87%) and lowest in the Americas (40 to 50%).

Antiviral drugs against herpes viruses can be administered to a patient in multiple ways, e.g., systemically, orally, topically, and parenterally. As with all drugs, the physico-chemical stability, the storage stability and in-use stability when used in methods of treatment and/or prevention on or in the patients is of utmost importance. While the physico-chemical stability of the compound pritelivir is already quite good, said compound as such demonstrates UV absorption.

It is thus an object of the invention to provide even more stable, and particularly photostable compounds that show fewer impurities. Mesylate salt forms of the compound pritelivir are an example of a quite stable form, but residual impurities may be present in conventionally produced products, which is another object of the invention to overcome. The aforementioned and other objectives have been achieved by the present invention.

The physico-chemical stability and photostability of the salts, and particularly of a maleate salt of the free base of N-[5-(aminosulfonyl)-4-methyl-1,3-thiazol-2-yl]-N-methyl-2-[4-(2-pyridinyl)-phenyl]-acetamide as provided by the present invention ensures that respective pharmaceutical compositions that are formulated to comprise said salts, specifically said maleate salt, have a substantially reduced amount of any decomposition/decay products. In other words, said salts and particularly the maleate salt of the invention as active pharmaceutical ingredient (hereinafter abbreviated as "API") is present at higher degrees of purity (i.e. lower amount of decay products) or the dose of such API per volume unit is higher. These characteristics of these salts, and particularly of the maleate salt of the invention permits reducing the initial amount of API upon formulation of pharmaceutical compositions thereof, because the effective concentration per volume unit of a given pharmaceutical is achieved at respective lower level and can be maintained for a longer period of time when directly compared with formulations that are not based on these salts, particularly on a maleate salt of the free base of N-[5-(aminosulfonyl)-4-methyl-1,3-thiazol-2-yl]-N-methyl-2-[4-(2-pyridinyl)-phenyl]-acetamide.

In summary, the present invention provides for stable salt forms, especially for a stable maleate salt of the free base of pritelivir, whereby surprisingly with the addition of a weak acid such as e.g. maleic acid, salts of free base pritelivir could be obtained which result in higher intrinsic pH values without a simultaneous decreasing of solubility properties, so to still ensure a pharmaceutical use in topical (higher pH reduces skin irritation effects) and oral applications (without change of bioavailability properties).

Further, the herein described inventive manufacturing processes of the salts of the free base of pritelivir, particularly of the maleate salt as disclosed herein, ensures that impurities arising from the production process, e.g. from solvents, or decay products of either the maleate salt as API or other compounds used in the manufacturing process are essentially absent. By contrast, as aforementioned, it is known that mesylate salts of active compounds are an example of an essentially stable form, but they contain potentially residual impurities arising in conventionally produced products thereof.

Therefore, the present invention provides surprisingly and unexpectedly for physio-chemically stable salt forms of the free base N-[5-(aminosulfonyl)-4-methyl-1,3-thiazol-2-yl]-N-methyl-2-[4-(2-pyridinyl)-phenyl]-acetamide, particularly with maleic acids. Specifically the herein provided maleate salts of the free base of pritelivir exhibit unexpectedly higher intrinsic pH values without decreasing the solubility properties.

Very surprisingly, the maleate salts of the invention exhibit a significant photostability, which is advantageous particularly for the use in topical formulations thereof that are intended to be used in methods of treating/preventing infections with herpes virus infections. A pharmaceutical formulation of a photostable API at higher pH simultaneously reduces skin irritation effects and allows for stability thereof even under light exposure. Moreover, when said maleate salts as API are used in oral administration forms, due to the above-described properties, the bioavailability properties of the maleate salts are not affected.

In addition, the present invention provides unexpectedly for stable salt forms, particularly of a maleate salt of the free base of pritelivir that per se have a high degree of purity when directly being obtained from the herein disclosed manufacturing processes and due to the stability can be stored for prolonged periods of time. Furthermore, upon formulation as pharmaceuticals and storage of these salts, specifically the maleate salt as API, this API is present at high concentrations essentially without or extremely low decomposition which ensures that the therapeutically effective concentration per volume unit of a pharmaceutical provided by the invention remains high.

Abbreviations

2-Me-THF 2-methyl tetrahydrofurane
ac acetone
ACN acetonitrile
am. amorphous
API active pharmaceutical ingredient
COX cyclooxygenase
DCM dichloromethane
DMSO dimethylsulfoxide
DSC differential scanning calorimetry
HPLC high performance liquid chromatography
HP-beta CD Hydroxypropyl-beta-cyclodextrin
Hept n-heptane
HSV herpes simplex virus
IPA isopropanol
LIMS-Sample/ID unique number provided by LIMS system for analytical samples
LIMS-Task/ID unique number provided by LIMS system for analytical task/measurement
MVTR moisture vapor transmission rate
MCH methyl cyclohexane
MEK 2-butanone (methyl ethyl ketone)
MIBK methyl isobutyl ketone
NSAIDs non-steroidal anti-inflammatory drugs
NMP N-Methyl-2-pyrrolidone
NMR nuclear magnetic resonance (spectroscopy)
PSAs produce pressure sensitive adhesives
STX Saxitoxin
TBME tert butyl methyl ether (MtBE)
TGA thermogravimetry
THF tetrahydrofurane
Tol toluene
TTX tetrodotoxin
XRPD X-ray powder diffraction

DETAILED DESCRIPTION OF THE INVENTION

Before describing the invention in detail, it is deemed expedient to provide definitions for certain technical terms used throughout the description. Although the present invention will be described with respect to particular embodiments, this description is not to be construed in a limiting sense. Before describing in detail exemplary embodiments of the present invention, definitions important for understanding the present invention are given.

Definitions

The term "pritelivir" with the context of the invention denotes the compound N-[5-(aminosulfonyl)-4-methyl-1,3- thiazol-2-yl]-N-methyl-2-[4-(2-pyridinyl)-phenyl]-acetamide per se. That is, an expression such as "the free base of pritelivir" or similar expressions denote the free base of the compound N-[5-(aminosulfonyl)-4-methyl-1,3-thiazol-2-yl]-N-methyl-2-[4-(2-pyridinyl)-phenyl]-acetamide. Likewise, a mesylate salt of pritelivir would denote a mesylate salt of a compound N-[5-(aminosulfonyl)-4-methyl-1,3-thiazol-2-yl]-N-methyl-2-[4-(2-pyridinyl)-phenyl]-acetamide.

With the context of the invention, similar expressions which all would denote the compound pritelivir are "BAY 57-1293", "AIC090096" and "AIC316".

Likewise, the terms "pritelivir", "BAY 57-1293", "AIC090096" and "AIC316" or the compound "N-[5-(aminosulfonyl)-4-methyl-1,3-thiazol-2-yl]-N-methyl-2-[4-(2-pyridinyl)-phenyl]-acetamide" would reflect throughout the text a compound having the structural formula:

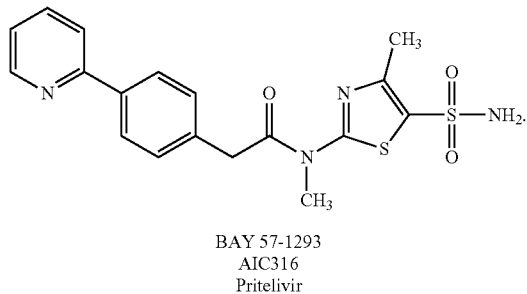 [SMILES: Cc1nc(N(C)C(=O)Cc2ccc(-c3ccccn3)cc2)sc1S(N)(=O)=O]

BAY 57-1293
AIC316
Pritelivir

The term "maleate salt" or similar terms denote a maleate salt of the free base of the compound N-[5-(aminosulfonyl)-4-methyl-1,3-thiazol-2-yl]-N-methyl-2-[4-(2-pyridinyl)-phenyl]-acetamide.

In the context of the description the expression "maleate salt" or similar expressions denote the salt obtained from the free base of N-[5-(aminosulfonyl)-4-methyl-1,3-thiazol-2-yl]-N-methyl-2-[4-(2-pyridinyl)-phenyl]-acetamide when reacted with maleic acid. The maleate ion is the ionized form of maleic acid. Maleic acid or cis-butenedioic acid is an organic compound that is a dicarboxylic acid, a molecule with two carboxyl groups. Its chemical formula is $HO_2CCHCHCO_2H$. Maleic acid is the cis-isomer of butenedioic acid, whereas fumaric acid is the trans-isomer. Maleic acid is a less stable molecule than fumaric acid. Maleic acid is more soluble in water than fumaric acid. The melting point of maleic acid (135° C.) is also much lower than that of fumaric acid (287° C.). Both properties of maleic acid can be explained on account of the intramolecular hydrogen bonding that takes place in maleic acid at the expense of intermolecular interactions, and that are not possible in fumaric acid for geometric reasons. Specifically, maleic acid and the ionized form of maleic acid, i.e. the maleate ion, is further characterized by three double-bondings.

As used in this specification and in the appended claims, the singular forms of "a" and "an" also include the respective plurals unless the context clearly dictates otherwise.

The term "photostability" or similar expressions denote(s) the physico-chemical stability of the maleate salt of the free base N-[5-(aminosulfonyl)-4-methyl-1,3-thiazol-2-yl]-N-methyl-2-[4-(2-pyridinyl)-phenyl]-acetamide under light exposure of 300-800 nm wavelengths, and with a light exposure quantity of at least 1.2 million Lux hours, and with a light exposure energy of at least 200 watt hours/$m^2$ which does not result in pharmaceutically unacceptable change. Photostability may be tested in accordance with the ICH Topic Q1B guidance on Photostability Testing of New Active Substances and Medicinal Products, which is hereby incorporated by reference.

In the context of the present invention, the terms "about" and "approximately" denote an interval of accuracy that a person skilled in the art will understand to still ensure the technical effect of the feature in question. The term typically indicates a deviation from the indicated numerical value of ±20%, preferably ±15%, more preferably ±10%, and even more preferably ±5%.

It is to be understood that the term "comprising" is not limiting. For the purposes of the present invention the term "consisting of" is considered to be a preferred embodiment of the term "comprising of". If hereinafter a group is defined to comprise at least a certain number of embodiments, this' is meant to also encompass a group which preferably consists of these embodiments only.

Furthermore, the terms "first", "second", "third" or "(a)", "(b)", "(c)", "(d)" etc. and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

In case the terms "first", "second", "third" or "(a)", "(b)", "(c)", "(d)" etc. relate to steps of a method or use there is no time or time interval coherence between the steps, i.e. the steps may be carried out simultaneously or there may be time intervals of seconds, minutes, hours, days, weeks, months or even years between such steps, unless otherwise indicated in the application as set forth herein above or below.

According to the present invention, the term "antiviral effective amount" means the total amount of each active component that is sufficient to show a meaningful patient benefit, i.e., healing of acute conditions characterized by inhibition of the herpes virus infection. When applied to an individual active ingredient, administered alone, the term refers to that ingredient alone. When applied to a combination, the term refers to combined amounts of the active ingredients that result in the therapeutic effect, whether administered in combination, serially or simultaneously.

In one aspect, the terms "prophylaxis or prevention" as used herein and in the claims refers to the administration or use of the herein disclosed compounds or compositions in order to protect e.g. a non-infected organism or e.g. a non-infected cell of an organism from being infected. With the context of the invention, however, this also means that an organism may be already infected by a virus, but the spread of said virus in the organism (from cell to cell) or within the organisms' social environment is prevented by the salts of the invention, particularly by a maleate salt of the invention. The organism may be human or other mammal, whereby human is preferred. Thus, in one aspect of the invention, the organism to whom the compound or pharmaceutical composition is administered is a human being that is infected by a herpes virus, e.g., HSV-1 and/or HSV-2, or a human being that is in danger of being infected by such viruses. For further definitions on "prophylaxis/prevention" aspects of the invention see below.

The terms "treat, treating, treatment" as used herein and in the claims means preventing or ameliorating diseases associated with herpes virus infection.

The physical characterization(s) of the salts of the invention, specifically of the maleate salts of the invention, as referred to herein, were performed using compendial methods as per European Pharmacopoeia (Ph. Eur.) and/or the U.S. Pharmacopeial Convention (USP).

Herein below, various embodiments of the invention are explained in more detail. Wherever respective alternatives in terms of ingredients in compositions, types of pharmaceutical compositions, concentrations of ingredients, periods of time of administration, frequencies of administration, medical indications to be treated are mentioned, the person skilled in the would immediately understand that individual combinations can be made as long as these are technically possible or if not otherwise explicitly indicated.

A Maleate Salt of the Free Base of Pritelivir

In one embodiment the present application relates to a maleate salt of the free base of N-[5-(amino-sulfonyl)-4-methyl-1,3-thiazol-2-yl]-N-methyl-2-[4-(2-pyridinyl)phenyl]acetamide having the molecular formula $HO_2CCHCHCO_2H$. Characteristic properties of said maleate salt of the invention are shown in FIG. 1. An Ortep Plot of the maleate salt is shown in FIG. 2. Characteristic XRPD-peaks thereof are depicted in the FIGS. 10 and 11.

Said maleate salt is further characterized by a compound of the formula (I):

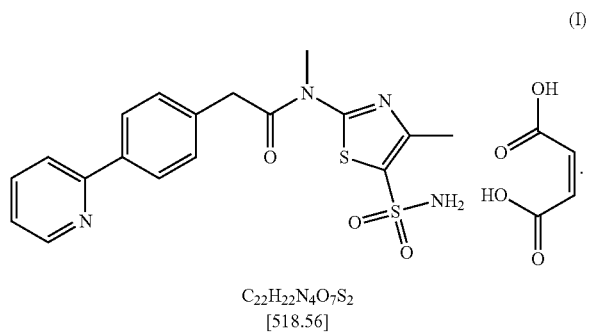

$C_{22}H_{22}N_4O_7S_2$
[518.56]

As used herein, the terms "storage stable" or "photostable" and corresponding terms indicate that the maleate salt of the invention does not decompose or decay for prolonged periods of time. This means that the maleate salt concentration remains constantly very high as can be measured using standard measuring methods permitting the identification of said compound and/or decomposition products thereof, e.g. HPLC, XRPD, and $^{13}$C- and $^1$H-NMR-spectroscopy methods showing the standard profile of the compound N-[5-(amino-sulfonyl)-4-methyl-1,3-thiazol-2-yl]-N-methyl-2-[4-(2-pyridinyl)phenyl]acetamide (i.e. pritelivir).

The physico-chemical characterisation of the salts of the invention, and particularly of the maleate salt as referred to herein was generally performed by using compendial methods as per European Pharmacopoeia (Ph. Eur.) and/or the U.S. Pharmacopeial Convention (USP).

Due to the above-mentioned general absence of impurities (either of the salts of the invention, specifically of the maleate salt as directly obtained from the manufacturing processes or due to decomposition of the N-[5-(aminosulfonyl)-4-methyl-1,3-thiazol-2-yl]-N-methyl-2-[4-(2-pyridinyl)phenyl]acetamide), the purity of these salts, specifically of the maleate salt of the free base of pritelivir as the manufacturing product and upon formulation of compositions or medicaments comprising initially these salts of the free base of pritelivir is very high, i.e. a high concentration of N-[5-(amino-sulfonyl)-4-methyl-1,3-thiazol-2-yl]-N-methyl-2-[4-(2-pyridinyl)phenyl]acetamide per volume unit is achieved.

This is very beneficial when the salts of the invention are used in the formulation of pharmaceuticals and medicaments, specifically when used in topical formulations thereof, because the effective concentration of the active compound per volume unit is very high.

This allows reducing the amount of the inventive salts, specifically of a maleate salt of the free base of pritelivir upon formulation whilst at the same time keeping a suitably high effective dose of the active compound. This is particularly desirable for pharmaceuticals used as topical compositions (unlike single unit dosage forms, e.g. essentially solid pharmaceuticals in form of tablets, etc., or—as another example—dosage forms for reconstitution in a pharmaceutically acceptable medium or carrier for immediate use as understood by the skilled person, e.g., for systemic or parenteral use), because the active ingredient in topically applied pharmaceuticals are subject to harsh environmental conditions in terms of changes in temperature, light exposure, such as UV-irradiation, (relative) humidity, mechanical stress upon application to affected areas of the skin or mucosa, and the like.

Under such harsh conditions, it is important that a sufficiently high and therapeutically effective concentration of the API is achieved as fast as possible on the treated surfaces and in the cells forming the surfaces (e.g. the epidermal and dermal layers of the skin where herpes viruses damage affected cells). When the effective antiviral concentration in the treated area (cells, organs, e.g. the skin, or parts thereof) is reached fast, the number of herpes viruses in the treated area decreases. This reduces also the number of viruses, particularly herpes simplex viruses, in the affected area that may infect nerve cells in which these viruses may persist in a latent state, only to be reactivated by a physico-chemical stimulus, for example, changes in the cells due to psychological stress, UV-stress, or any other factor shifting the balance in the affected cell from herpes virus latency (and expression of respective virally encoded polypeptides and/or polynucleotides) to herpes virus reactivation. Reactivation causes the herpes virus to exit the state of latency and leave the cells forming the latency reservoir only to infect and productively proliferate in cells that are later destroyed, either by the viruses themselves or by host defence mechanisms, e.g. by the immune cells.

With the above context, a further embodiment of the present invention is a method of treatment or suppression of the incidence of a herpes simplex virus subtype 1 or 2 infection, or suppression of transmission of a herpes simplex virus subtype 1 or 2 infection, comprising administering to a subject in need thereof an effective amount of a composition of the salts of the invention, specifically of a maleate salt of the free base of N-[5-(aminosulfonyl)-4-methyl-1,3-thiazol-2-yl]-N-methyl-2-[4-(2-pyridinyl)-phenyl]acetamide.

In another aspect of the invention, the term(s) "prophylaxis and/or prevention" or similar term(s) in the art pertinent to the instant invention clearly mean to one of ordinary skill in the art the suppression or reduction of the recurrence of infection or the suppression or reduction of transmission of infection with herpes simplex virus subtype 1 or 2.

In the context of the invention, the term(s) "prophylaxis and/or prevention" does not mean, even under the broadest reasonable interpretation, the complete and total absence of any infectious virus particles or infected cells from a patient. With the background of the instant invention, such a position is reasonable in the art pertinent to the herein disclosed subject matter. In support of these definitions of the term(s) "prophylaxis and/or prevention" the following publications are herein incorporated by reference:

Abdool Karim, S. S., et al. (2015). Tenofovir Gel for the Prevention of Herpes Simplex Virus Type 2 Infection. N Engl. J Med 373, 530-539.

Andrei, G. et al (2011). Topical tenofovir, a microbicide effective against HIV, inhibits herpes simplex virus-2 replication. Cell Host. Microbe 10, 379-389.

Corey, L., et al., (2004). Once-daily valacyclovir to reduce the risk of transmission of genital herpes. N. Engl. J. Med. 350, 11-20.

Kleymann, G., et al. (2002). New helicase-primase inhibitors as drug candidates for the treatment of herpes simplex disease. Nat. Med. 8, 392-398.

Mertz, G. J., et al., (1985). Frequency of acquisition of first-episode genital infection with herpes simplex virus from symptomatic and asymptomatic source contacts. Sex Transm. Dis. 12, 33-39.

Reitano, M., et al., (1998). Valaciclovir for the suppression of recurrent genital herpes simplex virus infection: a large-scale dose range-finding study. International Valaciclovir HSV Study Group. J. Infect. Dis. 178, 603-610.

Schiffer, J. T., et al., (1997). Frequent genital herpes simplex virus 2 shedding in immunocompetent women. Effect of acyclovir treatment. J. Clin Invest 99, 1092-1097.

Wald, A., et al. (2014). Helicase-primase inhibitor pritelivir for HSV-2 infection. N Engl. J Med 370, 201-210.

Wald, A., et al. (2000). Reactivation of genital herpes simplex virus type 2 infection in asymptomatic seropositive persons. N. Engl. J. Med. 342, 844-850.

Zhu, J., et al. (2007). Virus-specific CD8+ T cells accumulate near sensory nerve endings in genital skin during subclinical HSV-2 reactivation. J. Exp. Med. 204, 595-603.

Gold, D., and Corey, L., MINIREVIEW Acyclovir Prophylaxis for Herpes Simplex Virus Infection. Antimicrobial Agents and Chemotherapy, March 1987, p. 361-367.

Tyring, S., Baker, D., Snowden, W., Valacyclovir for Herpes Simplex Virus Infection: Long-Term Safety and Sustained Efficacy after 20 Years' Experience with Acyclovir. The Journal of Infectious Diseases 2002; 186(Suppl 1):S40-6.

These documents also support the correlation between helicase-primase inhibition and the prevention or prevention of transmission of herpes simplex virus infection as having been demonstrated in the art.

Furthermore, the above mentioned Kleymann, 2002, teaches on page 396, bottom of the left column, that recurrent disease and asymptomatic virus shedding are nearly completely suppressed by helicase-primase inhibitors, which should decrease person-to-person transmission, i.e., to effectively prevent the transmission of HSV.

The above-mentioned disclosure in Corey, 2004, teaches at the bottom of page 11 and on page 17, first column, that once daily suppressive therapy with valacyclovir significantly reduces the risk of transmission, i.e., prevented the transmission, of genital herpes among heterosexual, HSV-2 discordant couples. The study achieved these results by a drug that has been shown to suppress shedding of HSV type 2 (HSV-2) on genital mucosal surfaces. See the top of page 11. Further, it has been found that the frequency and amount of HSV that is shed subclinically on genital mucosal surfaces is the principal source of transmitted infections. See citations 20-22, dating back to 1997, 1998 and 1997 in the order recited. As such, an approach to reduce the frequency and amount of HSV that is shed subclinically on genital mucosal surfaces is a way to achieve prevention of transmission of herpes.

Karim, 2015, teaches at the bottom of page 530 that based on the study therein, it was shown that pericoital application of tenofovir gel reduced HSV-2 acquisition in women, i.e., prevented getting HSV. The effectiveness was a reduction of 51%. See page 534, second column. In an earlier study by the same group dating back to 2010 (see citation 6 in this reference), it was shown that pericoital application of a topical vaginal-gel formulation of tenofovir reduced HIV acquisition. While HIV is a different virus, it is not unbelievable by those of ordinary skill in the art in view of the above that a drug is able to prevent the acquisition of a viral infection. Moreover, such is explicitly confirmed to occur by Karim in the case of HSV. Gold and Corey from March 1987 support the well-known effective prophylaxis of acyclovir (i.e., viral DNA polymerase inhibitor). In addition, Tyring et al. from 2002 supports the efficacy of the prodrug valacyclovir (i.e., viral DNA polymerase inhibitor).

The person skilled in the art is aware that in case of HSV-1 and HSV-2 infection, although the viruses are present within the body due to infection, there is no symptomatic outbreak because the maleate salt of the free base of N-[5-(aminosulfonyl)-4-methyl-1,3-thiazol-2-yl]-N-methyl-2-[4-(2-pyridinyl)phenyl]acetamide effectively suppresses viral shedding and outbreak, which is "prophylaxis" or "suppression" against the resultant symptoms of HSV-1 and HSV-2 infection.

In further support of the "prophylaxis equates suppression" aspect of the invention, the above mentioned citations for valacyclovir (i.e. Tyring et al. 2002) and acyclovir (i.e. Gold et al. 1987) are reiterated, which also prove that it is well established that HSV infections are in normal individuals asymptomatic, and what prophylactic/suppressive therapy means in this art. Moreover, effective HSV-prophylaxis has been clinically demonstrated in human trials, as such.

In this regard, a poster from ICAAC 2014 for the HSV-2 genital herpes indication is incorporated by reference (Wald et al., 2014, supra). Finally, one of ordinary skill in the art knows that by analogy to Tenofovir, the salts, specifically the maleate salt of the free base of N-[5-(amino-sulfonyl)-4-methyl-1,3-thiazol-2-yl]-N-methyl-2-[4-(2-pyridinyl)phenyl]acetamide as helicase-primase inhibitor(s) is/are known to have an even higher antiviral efficacy than Tenofovir in case of HIV, and thus, for the skilled person, N-[5-(aminosulfonyl)-4-methyl-1,3-thiazol-2-yl]-N-methyl-2-[4-(2-pyridinyl)phenyl]acetamide also would be expected to have a more pronounced prophylactic efficacy. In this regard, particularly relevant are the publications by Andrei et al. and Kleymann et al. as mentioned above. The $IC_{50}$-values demonstrated therein for Tenofovir are significantly higher when compared to the maleate salt of the free base of N-[5-(amino-sulfonyl)-4-methyl-1,3-thiazol-2-yl]-N-methyl-2-[4-(2-pyridinyl)phenyl]acetamide.

As used herein, the term "anti-inflammatory agent" refers generally to any compound or combination of compounds that, upon administration to an individual which is experiencing inflammation, tends to reduce such inflammation, e.g. steroids, and non-steroidal anti-inflammatory drugs (NSAIDs) as defined also in the section supra.

As used herein "centrally and peripherally acting analgesics" comprise opioid analgesics. Opioid analgesics comprise, e.g. buprenorphine or a physiologically acceptable salt or ester thereof, suitable opioid analgesics include alfentanil, allylprodine, alphaprodine, anileridine, benzylmorphine, bezitramide, butorphanol, clonitazene, cyclazocine, desomorphine, dextromoramide, dezocine, diampromide, diamorphone, dihydrocodeine, dihydromorphine, dimenoxadol, dimepheptanol, dimethylthiambutene, dioxaphetylbutyrate, dipipanone, eptazocine, ethoheptazine, ethylmethylthiambutene, ethylmorphine, etonitazene, fentanyl, heroin, hydromorphone, hydroxypethidine, isomethadone, ketobemidone, levallorphan, levorphanol, levophenacylmorphan, lofentanil, meperidine, meptazinol, metazocine, methadone, metopon, morphine, myrophine, nalbuphine, narceine, nicomorphine, norlevorphanol, normethadone, nalbuphine, nalorphine, naloxone, naltrexone, normorphine, norpipanone, opium, oxycodone, oxymorphone, papaveretum, pentazocine, phenadoxone, phenomorphan, phenazocine, phenoperidine, piminodine, piritramide, profadol, prophepτazine, promedol, properidine, propiram, propoxyphene, sufentanil, tilidine and tramadol. Also included are esters, salts and mixtures of any of the foregoing.

As used herein, non-opioid analgesic comprise, e.g. NSAID, a tricylic antidepressant (e.g. amitryptyline), an anticonvulsant (e.g. gabapentin) or an antimigraine compound (e.g. sumatriptan or naratriptan). The NSAID may be a cyclooxygenase (COX) COX-1 or COX-2 inhibitor. Specific examples of NSAIDs include ibuprofen, flurbiprofen, diclofenac, indomethacin, piroxicam, ketoprofen, etodolac, diflusinal, meloxicam, aceclofenac, fenoprofen, naproxen, tiaprofenic acid, tolmetin, celecoxib and rofecoxib, and their physiologically acceptable salts and esters. Suitable salts are alkali addition salts such as the potassium or sodium salt.

In the compositions of the invention, long and short acting local and volatile anesthetics may be used that are selected from the group comprising bupivacaine, lidocaine, xyclocaine, tetrodotoxin (TTX), Saxitoxin (STX), etc.

Topical Application

In general, fast drug delivery through the skin barrier is crucial for topical application forms. Suspended drug forms could have a significant impact on the topical delivery properties, since only drugs in soluble state can cross the stratum corneum of the epidermis. With drugs in suspended forms, the amount of topically delivered drug could be low since suspended drugs would first need to go into solution. This also might slow down the drug delivery rate for topical application forms.

In contrast, when a drug is topically applied in dissolved form, the drug delivery should be faster and the extent of drug delivered should be manifold higher when compared to its $IC_{90}$ values.

pH/Apparent pH/Topical Formulations pH is an important parameter for topical formulations especially due to its impact on the patient compliance, drug stability and skin permeation of the active moiety. Most conventional topical formulations are based on aqueous systems such as gels, creams and lotions, however, non-aqueous systems such as oils, ointments are also used for hydrophobic drugs. Precise pH measurement of non-aqueous formulations is much more complex compared to aqueous formulations.

In theory, while measuring pH of the aqueous solutions, a proportion of the water molecules are dissociated into H+ and $OH^-$ ions, and therefore pH value can be precisely obtained on the scale of 0 to 14. However, the pH scale of 0 to 14 may not be applicable for non-aqueous systems.

As the pH value is a measure of hydrogen ion activity, in a solution with aprotic solvents the concentration of hydrogen ions would be markedly reduced or almost negligible.

The pH electrodes used in normal lab setting are calibrated using aqueous buffers and very well suited to record $H^+$ ion concentration of aqueous systems. The electrochemistry of these pH electrodes may not be suited to record $H^+$ ion concentrations in the non-aqueous systems due to very less concentration.

Porras and Kenndler suggested that pH measurement of non-aqueous system is possible using an aqueous calibration, however, the pH value should be considered as an apparent pH. Apparent pH provides relative acidity/alkalinity of the system.

Several practical difficulties can be encountered while measuring apparent pH of the non-aqueous systems. Low $H^+$ ion concentration can be responsible for imprecise detection of the electrochemical potential between the glass pH-indicating electrode and the test sample, which can result in fluctuating pH measurements, long response times and inaccurate readings.

There are other factors that can contribute to these effects:

Majority of pH electrodes rely on a hydrated gel layer on the outside of the glass bulb to detect $H^+$ activity. Dehydration of the gel layer due to the low water content in non-aqueous samples results in slow response times and imprecise measurements.

Non-aqueous systems may have poor electrical conductance and therefore decrease the efficiency of the electrical components required for detecting changes in $H^+$ activity.

Aqueous buffers used for calibrating the pH meter may not be compatible with non-aqueous samples therefore the results cannot be directly translated.

The instant inventors surprisingly found that the salts of the invention, and specifically the maleate salt of the invention as active substance is more stable at ≥pH 4.0. Therefore, the invention also provides e.g. for ointment formulations with a pH around 4.0, although it is well known that this is an apparent pH due to very low concentration of the aqueous component.

With this context it is important to note that stability analysis of the inventors revealed apparent pH values ranging from 4-7 without any impact on the purity of the API. Therefore, a measured shift in apparent pH has no impact on assay and purity of the salts of the invention of the pritelivir free base forms, e.g. in an ointment formulation thereof.

Thus, in another embodiment the present application relates to a pharmaceutical composition as defined in any one of the embodiments further outlined below, wherein the maleate salt of the free base of N-[5-(amino-sulfonyl)-4-methyl-1,3-thiazol-2-yl]-N-methyl-2-[4-(2-pyridinyl)phenyl]-acetamide is present in an amount of 5.0% w/w, wherein the pharmaceutical composition is an ointment, and wherein said ointment is administered 5 times a day, and wherein said ointment is administered over a period of 4 days.

In another embodiment the present application relates to the pharmaceutical composition as defined in any one of the embodiments below, wherein the maleate salt of the free base of N-[5-(amino-sulfonyl)-4-methyl-1,3-thiazol-2-yl]-N-methyl-2-[4-(2-pyridinyl)phenyl]-acetamide is present in an amount of 5.0% w/w, wherein the pharmaceutical composition is a gel, and wherein said gel is administered 5 times a day, and wherein said gel is administered over a period of 4 days.

In another, embodiment the present application relates to the pharmaceutical composition as defined in any one of the embodiments below, wherein the maleate salt of the free base of N-[5-(amino-sulfonyl)-4-methyl-1,3-thiazol-2-yl]-N-methyl-2-[4-(2-pyridinyl)phenyl]-acetamide is present in an amount of 5.0% w/w, wherein the pharmaceutical composition is a cream, and wherein said cream is administered 5 times a day, and wherein said cream is administered over a period of 4 days.

In another aspect of the invention, the pharmaceutical compositions as disclosed herein for the pritelivir salts of the invention, particularly for the maleate salt may be suitably formulated for systemic, oral, topical or parenteral administration.

The N-[5-(aminosulfonyl)-4-methyl-1,3-thiazol-2-yl]-N-methyl-2-[4-(2-pyridinyl)-phenyl]-acetamide free base maleate according to the invention is a useful compound in methods of treatment and/or prophylaxis of infectious diseases and/or for use in the prevention of transmission of infectious diseases. Moreover, the N-[5-(aminosulfonyl)-4-methyl-1,3-thiazol-2-yl]-N-methyl-2-[4-(2-pyridinyl)-phenyl]acetamide free base maleate is highly active in therapeutic/preventive methods against herpesviruses and infections caused by herpes viruses and/or transmission of a herpes virus or herpes viruses.

Therefore, the N-[5-(aminosulfonyl)-4-methyl-1,3-thiazol-2-yl]-N-methyl-2-[4-(2-pyridinyl)-phenyl]acetamide free base maleate is especially useful for the preparation of a pharmaceutical composition to be used in methods of treatment and/or prophylaxis of diseases, which are caused by herpesviruses or caused by the transmission of a herpes virus or herpes viruses.

The N-[5-(aminosulfonyl)-4-methyl-1,3-thiazol-2-yl]-N-methyl-2-[4-(2-pyridinyl)-phenyl]-acetamide free base maleate is especially useful in methods for the treatment and/or prophylaxis of infections, which are caused by herpes simplex viruses, or for the use in the prevention of transmission of a herpes virus or herpes viruses.

Infections with herpes simplex viruses (HSV, subtype 1 and 2) are categorized into one of several distinct disorders based on the site of infection. Orofacial herpes simplex infection, the visible symptoms of which are colloquially called cold sores or fever blisters, affects the face and mouth. Orofacial herpes is the most common form of infection. Genital herpes is the second common form of a herpes simplex infection. Although genital herpes is largely believed to be caused by HSV-2 only, genital HSV-1 infections are increasing. Other disorders such as herpetic whitlow, herpes gladiatorum, ocular herpes (keratitis), cerebral herpes infection encephalitis, Mollaret's meningitis, neonatal herpes, and possibly Bell's palsy are also caused by herpes simplex viruses.

The N-[5-(aminosulfonyl)-4-methyl-1,3-thiazol-2-yl]-N-methyl-2-[4-(2-pyridinyl)-phenyl]-acetamide free base maleate is thus useful in methods for the treatment and/or prophylaxis of infections which are caused by herpes simplex viruses and/or in methods for the prevention of transmission of herpes simplex viruses.

The N-[5-(aminosulfonyl)-4-methyl-1,3-thiazol-2-yl]-N-methyl-2-[4-(2-pyridinyl)-phenyl]-acetamide free base maleate of the present invention can be combined and administered together with other pharmaceutically active ingredients, e.g., anti-inflammatory agents such as acetylsalicylic acid and acetaminophen, or with (local) anaesthetics, or other antiviral agents, etc.

Combinations of the inventive N-[5-(aminosulfonyl)-4-methyl-1,3-thiazol-2-yl]-N-methyl-2-[4-(2-pyridinyl)-phenyl]acetamide free base maleate with anaesthetics as well as pharmaceutical compositions containing such a combination are another embodiment of the present invention.

Furthermore, in another aspect, the inventive N-[5-(aminosulfonyl)-4-methyl-1,3-thiazol-2-yl]-N-methyl-2-[4-(2-pyridinyl)-phenyl]acetamide free base maleate can be combined and can be used in combination with an anti-viral agent. The anti-viral agent is preferably an antimetabolite and most preferably a nucleobase analogue, nucleotide analogue or nucleoside analogue drug.

It is further preferred if the anti-viral agent is useful against herpesviruses and/or against the transmission of a herpes virus or herpes viruses and is selected from the group of drugs comprising but not limited to or consisting of: trifluridine, idoxuridine, foscarnet, cidofovir, ganciclovir, aciclovir or penciclovir or the respective prodrugs valaciclovir, famciclovir or valganciclovir.

The combination of the inventive N-[5-(aminosulfonyl)-4-methyl-1,3-thiazol-2-yl]-N-methyl-2-[4-(2-pyridinyl)-phenyl]acetamide free base maleate and a further active agent like an anti-inflammatory, immunomodulatory, or anti-viral, agent, such as therapeutic vaccines, siRNAs, antisense oligonucleotides, nanoparticles or virus-uptake inhibitors such as n-docosanol, may be administered simultaneously in one single pharmaceutical composition or in more than one pharmaceutical composition, wherein each composition comprises at least one active agent.

The pharmaceutical compositions of the present invention can be prepared in a conventional solid and a conventional pharmaceutically-made adjuvant at suitable dosage level in a known way. Preferred preparations may be adapted for oral application. These administration forms include, for example, pills, tablets, film tablets, coated tablets, sustained release formulations, and capsules.

The pharmaceutical compositions according to the invention may comprise 5 to 70% by weight, more preferably 10 to 30% by weight of the N-[5-(aminosulfonyl)-4-methyl-1,3-thiazol-2-yl]-N-methyl-2-[4-(2-pyridinyl)-phenyl]acetamide free base maleate salt (all percentage data are percentages by weight based on the weight of the pharmaceutical preparation).

An inventive pharmaceutical composition may contain the following preservatives: phenoxyethanol, formaldehyde solution, parabens, pentanediol, or sorbic acid.

As pharmaceutically acceptable carrier, excipient and/or diluents can be used carriers such as preferably an inert carrier like lactose, starch, sucrose, cellulose, magnesium stearate, dicalcium phosphate, calcium sulfate, talc, mannitol, ethyl alcohol (liquid filled capsules); suitable binders include starch, gelatin, natural sugars, corn sweeteners, natural and synthetic gums such as acacia, sodium alginate, carboxymethylcellulose, polyethylene glycol and waxes, sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate; lubricants such as boric acid, sodium benzoate, sodium acetate, sodium chloride, magnesium stearate, calcium stearate, or potassium stearate, stearic acid, high melting point waxes, and other water soluble lubricants such as sodium chloride, sodium benzoate, sodium acetate, sodium oleate, polyethylene glycols and D, L-leucine; disintegrating agents (disintegrates) such as starch, methylcellulose, guar gum, modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures; coloring agents, sweetening agents, flavoring agents, preservatives; glidents are for example silicon dioxide and talc; suitable adsorbent are clay, aluminum oxide, suitable diluents are water or water/propylene glycol solutions for parenteral injections, juice, sugars such as lactose, sucrose, mannitol, and sorbitol, starches derived from wheat, corn rice, and potato, and celluloses such as microcrystalline cellulose.

Patches

The salt compounds, particularly a maleate salt and pharmaceutical compositions thereof in accordance with the present invention can also be administered using patches that are applied on parts of the body of an organism, e.g. of a human being, that is infected by a herpes virus, e.g. infected with HSV-1 and/or HSV-2. More particularly, such patches of the invention comprise a skin adhesive layer, a backing layer and a release liner, the adhesive layer comprising a salt compound of the invention, particularly a maleate salt of the free base of pritelivir of the invention, and/or other active compounds dissolved in a low volatile solvent and a polymeric adhesive soluble in highly volatile solvents. A salt compound of the invention, particularly a maleate salt of the free base of pritelivir of the invention may be incorporated as antiviral agent in the adhesive layer in a therapeutically and/or prophylactically effective amount, e.g., from 0.1 to 10% by weight of the dried adhesive layer, dissolved in a low volatile solvent.

"Solvents" can be classified in function of their physical-chemical properties. Key properties, among the others, include density, viscosity, dielectric constant, dipole moment, melting and boiling point. "Solvents" can be broadly classified as low, middle or highly boiling according to boiling temperature at 1 bar: low boiling: boiling ranges below 100° C.; medium boiling: boiling ranges between 100° C. and 150° C.; high boiling: boiling ranges above 150° C. A low boiling solvent is a highly volatile solvent whereas a high boiling solvent is a solvent with a poor inclination to evaporate so that it can be defined as a low volatile solvent. An example of a low volatile solvent according to the invention is dimethylsulfoxide that may be present in an amount from 10 to 50% by weight of the dried adhesive layer. The adhesive polymer is selected from pectin, agar gum, acacia gum, xanthan gum, polyvinyl alcohol, polymethacrylic acid, polymethacrylate, acrylates/alkylmethacrylates copolymers, any acrylic ester copolymer, aminoalkyl methacrylate copolymer, polyvinyl pyrrolidone, cellulose or cellulose derivatives, such as hydroxypropylcellulose, hydroxyethylcellulose, or blends thereof. The adhesive layer may be formed from a solution of the adhesive polymer in a highly volatile solvent, i.e. having a low boiling point (in the range of 40° C. to 100° C.) and high vapor pressure. Said solvent is then usually evaporated during the manufacturing process even though a certain amount, up to 15% by weight, may be left in the adhesive layer after drying. The adhesive polymer or the adhesive polymer blend may be present in an amount from 20 to 50% by weight of the dried adhesive layer.

A patch of the present invention may further contain citric acid, succinic acid, lactic acid and esters thereof as a non-polymeric crystallization inhibitors, in an amount from, e.g., 0.5 to 15% by the weight of the dried adhesive layer. The patch may also contain other excipients such as cross-linkers, penetration enhancers, plasticizers, preservatives, antioxidants, fragrances, emollients. The backing layer may be transparent, semi-occlusive or occlusive, oxygen permeable, e.g., consisting of polyurethane ether or ester film, polyethylene, ethylene vinyl acetate or polyolephine film with a moisture vapor transmission rate (MVTR) from 50 to 3500 g/m$^2$/day and a thickness from 20 to 150 µm. The backing layer should be very flexible and soft, transparent or colored and can be occlusive or perspirating, providing a masking effect of the cold sore. Moreover, it protects the damaged skin and the viral lesions from the external contact, thus reducing the patient's pain and the possibility of further contaminations or infections, and improving the re-epithelization process. The adhesive layer is protected from the external environment through a release liner, that has to be removed before applying the patch to the site of the body interested by the viral lesions. Once the patch is applied, through the self-adhesive layer, it can be kept on-site up 6 to 24 hours, delivering the active ingredient into and across the skin.

In accordance with the invention, patches are prepared by a process comprising the steps of blending the solution of adhesive polymers in highly volatile solvents together with the other components and then casting the mixture on a silicone coated liner film, before drying and the final lamination. Highly volatile solvents evaporate, leaving the adhesive film on the release liner whereas the low volatile solvent remains in the adhesive layer preventing the drug crystallization. The polymers used according to this invention are those normally used to produce pressure sensitive adhesives (PSAs) or bio-adhesive film in an organic or aqueous solution, in a concentration ranging from 20 to 80%, preferably from 20 to 50% of the composition of the adhesive mixture, while the concentrations of the highly volatile solvent are from 10 to 50%.

In accordance with the instant invention, other components of the adhesive layer or of the reservoir layer include thickening agents, chemical permeation enhancers, non-polymeric crystallization inhibitors, flavors, surfactants, cross-linkers, buffering agents, plasticizers, preservatives, anti-oxidants, pigments. The selected solvents and polymers must of course be compatible and form an homogeneous solution which may be uniformly casted. Low boiling point solvents, i.e. high volatile solvents with boiling point not higher than 100° C., are preferably water, ethanol, methanol, isopropyl alcohol, ethyl acetate, more preferably water.

Thus, per the invention, it is possible to produce an anti-herpes patch, having an effective amount of the salt compound of the invention, particularly of the maleate salt of the invention, as effective drug agent that can be continuously delivered to the site of application. The low volatile solvents helps to avoid crystallization by keeping dissolved the active substances in the matrix and affects the diffusivity of the drug through the matrix, to reach the skin and the site of action. The matrix must be chosen according to the physical-chemical properties of the low volatile solvents or the solvents blend. The polymer must provide a good cohesiveness to the final product. The quantitative composition of the adhesive blend is chosen in order to have an acceptable film in terms of thickness, cohesion properties, mechanical resistance, skin adhesion, peel properties and handling. The polymer blend range in the dry matrix is 5 to 50%, most preferably 20 to 35%, solubilized in a low boiling point solvent or solvent mixture. The solvent percentage ranges from 20 to 70%, preferably from 35 to 55%, in the mixture that has to be casted to produce the adhesive layer or the reservoir layer. In the dry matrix the amount of low boiling point solvent must not exceed 15% by weight. The low volatile solvents, instead, are included in the dry matrix, entangled in the polymer and dissolving the active ingredients. The amount of these solvents in the dry state is in the range 10 to 50%, particularly in the range of 30 to 55%.

Processes for the Manufacture of the Salts of the Invention
Maleate Salt of the Free Base of Pritelivir

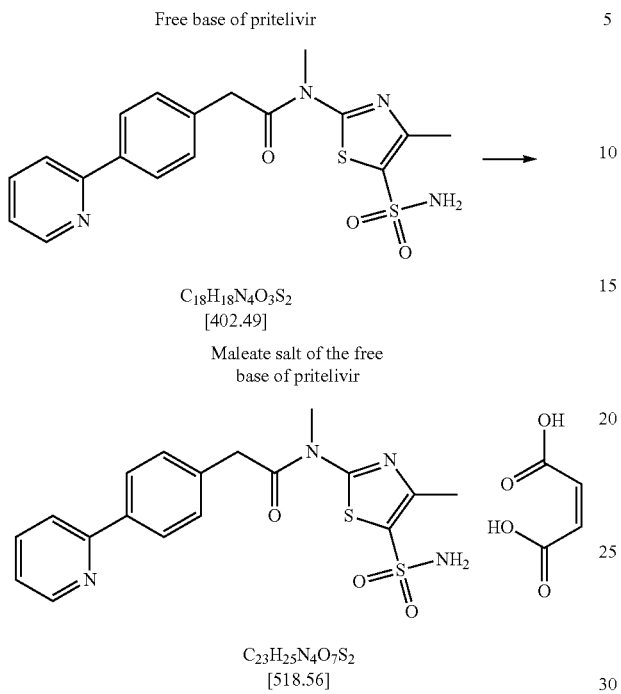

Synthesis Scheme of a Maleate Salt of the Free Base of Pritelivir.

In another aspect of the invention a process for the manufacture of the maleate salt of the free base of pritelivir is provided.

Said process comprises the following steps:
i) providing a mixing means, preferably a mixing means with overhead stirring,
ii) filling said mixing means of step i) with 460 to 490 g free base of pritelivir,
iii) suspending the free base of pritelivir of step ii) with 3 to 5 volumes of water,
iv) heating the suspension of step iii) to 45 to 55° C. by suitable heating means,
v) adding 225 to 240 g of maleic acid in solid form over a time period of 40 to 90 min. until resultant solution is obtained,
vi) cooling the solution obtained under step v) down towards 44 to 52° C.
vii) seeding an aliquot of the solution of step vi) with a maleate salt of the free base of pritelivir,
viii) over a period as of from 1.5 to 2.5 hours the resultant suspension of step vii) is allowed to cool down towards 18 to 24° C.,
ix) stirring the suspension of step viii) overnight follows,
x) the suspension of step ix) was filtered, so to obtain a resultant filter cake,
xi) the solid filter cake obtained under step x) is transferred to a mixing means, preferably a flask,
xii) rotary evaporation of the mixing means of step xi) follows for 25 to 32 hours while applying the following conditions:
   a. an ambient temperature of 30 to 40° C.,
   b. a pressure of 15 to 25 mbar,
   so to obtain a constant mass,
xiii) homogenisation follows, preferably homogenisation with mortar and pastle follows,
xiv) so to obtain a maleate salte of the free base of pritelivir in accordance with the invention.

In a preferred embodiment of the above process, said process comprises the following steps:
i) providing a mixing flask with overhead stirring,
ii) filling said mixing flask of step i) with about 475.4 g free base of pritelivir,
iii) suspending the free base of pritelivir of step ii) with about 4 volumes of water,
iv) heating the suspension of step iii) to about 51° C. by suitable heating means,
v) adding about 232 g of maleic acid in solid form over a time period of about 60 min. until resultant solution is obtained,
vi) cooling the solution obtained under step v) down towards about 48° C.,
vii) seeding an aliquot of the solution of step vi) with a maleate salt of the free base of pritelivir,
viii) over a period of about 2 hours the resultant suspension of step vii) is allowed to cool down towards about 21° C.,
ix) stirring the suspension of step viii) overnight follows,
x) the suspension of step ix) was filtered, so to obtain a resultant filter cake,
xi) the solid filter cake obtained under step x) is transferred to a mixing means, preferably a flask,
xii) rotary evaporation of the mixing means of step xi) follows for about 28 hours while applying the following conditions:
   a. an ambient temperature of about 35° C.,
   b. a pressure of about 20 mbar,
   so to obtain a constant mass,
xiii) homogenisation follows, preferably homogenisation with mortar and pastle follows,
xiv) so to obtain a maleate salte of the free base of pritelivir in accordance with the invention.

Other Tested Salts of the Invention

N-methyl-N-(4-methyl-5-sulfamoylthiazol-2-yl)-2-(4-(pyridin-2-yl)phenyl)acetamide Sulfate Salt of the Free Base of Pritelivir Process for the Manufacture of a Sulfate Salt of the Free Base of Pritelivir

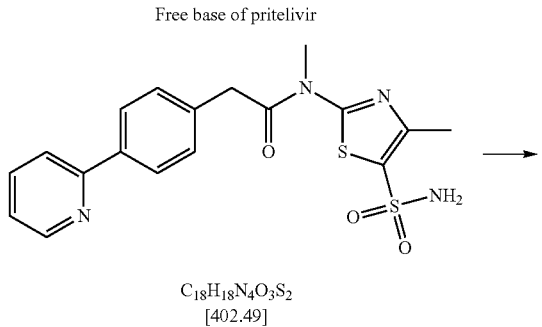

-continued

Sulphate salt of the free base of pritelivir

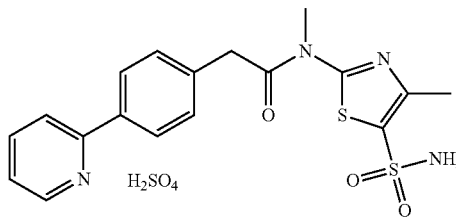

c$_{18}$H$_{20}$N$_4$O$_7$S$_3$
[500.57]

Synthesis Scheme of a Sulfate Salt of the Free Base of Pritelivir.

General Process Description

All equivalents, volumes (L/kg) and weights (kg/kg) refer to the weight of starting material free base of pritelivir. In a 2.5 L sulfonation flask with overhead stirring free base of pritelivir (1 eq., 1 wt., 250.0 g) is suspended in water (4.0 vol.) and ethanol (4.0 vol.). The suspension is heated to 50° C. A solution of sulphuric acid (96%, 1.05 eq., 0.256 wt.) in water (0.256 vol.) is prepared and 15% of the solution is added to the suspension at 50° C. After 5 minutes at 50° C. the suspension converts to a thicker suspension and is stirred for further 150 minutes at 50° C. The remaining sulphuric acid solution is added at 50° C. during 75 minutes to the suspension. The suspension cooled down to 21° C. during 3 hours and stirred for 13 hours at said 21° C. The suspension is filtered and the filter cake is washed with a mixture of water (0.8 vol.) and ethanol (0.8 vol.). After deliquoring the filter cake on the filter the solid is transferred to a flask and dried on a rotovap (35° C., <20 mbar, 6 h) to constant mass.

IPC: 93.59% dry mass (160° C.).

294.43 g sulfate salt of pritelivir free base (94.7% yield not corrected for assay).

Characterisation of Sulfate Salt of Free Base of Pritelivir:

Ethanol content by NMR: <100 ppm (below quantification limit).

Water content by Karl Fischer titration: 6.33% w/w (monohydrate 3.5%, dihydrate 6.7% w/w).

Assay by NMR: 95.3% w/w as monosulfate (calculated monosulfate content by NMR higher than Karl Fischer titration allows).

76.6% w/w as free base of pritelivir.

Sulfate salt: 18.1% w/w, theoretical (monohydrate monosulfate): 18.9% w/w (calculated, (difference free base) vs. (100%—water content)).

19.4% w/w (calculated from elementary analysis and NMR assay (free base of pritelivir).

Elementary analysis: atom found (% w/w) theoretical (% w/w)

| | |
|---|---|
| C: 41.7 | 41.7 |
| H: 4.5 | 4.3 |
| N: 10.8 | 10.8 |
| S: 17.8 | 18.6 |
| O: 25.4 | 24.7 |

Specific Process Description for Sulfate Salt of Pritelivir Free Base

Suspended free base of pritelivir in 1 L Ethanol and 1 L water is heated to a temperature of 50° C. 0.16 eq. sulfuric acid is added during 1 min. After approx. 5 min. a thick suspension is formed. Stirring for about further 2 hours follows to obtain a stirring suspension and 0.9 eq. sulfuric acid are added during 75 min. at temperature of 50° C. The suspension is allowed to cool down to room temperature and stirred for further 18 hours. Filtering, washing with 0.4 L ethanol/water 1/1 (v/v) and drying in vacuum follows.

Results:

Crude sulfate salt of pritelivir free base obtained: 294.4 g white solid (dry mass:93.6% (160° C.), <100 ppm Ethanol.

Sulfate content: pending (to be calculated from elementary analysis).

NMR: 85.7% w/w calculated as monosulfate
TGA: 6.48% weight loss
Karl Fischer: 6.23% w/w water
Scale purity: 250 G
Product (% theory): 94.7 (uncorrected)

N-methyl-N-(4-methyl-5-sulfamoylthiazol-2-yl)-2-(4-(pyridin-2-yl)phenyl)acetamide hemiethane-1,2-disulphonate Salt of Free Base of Pritelivir Process for the Manufacture of Ethane-1,2-disulfonic Acid Salt of Free Base of Pritelivir Free base of pritelivir

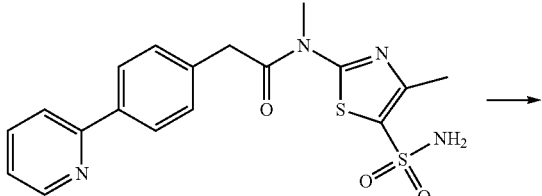

C$_{18}$H$_{18}$N$_4$O$_3$S$_2$
[402.49]

Hemiethane-1,2-disulfonate salt of the free base of pritelivir

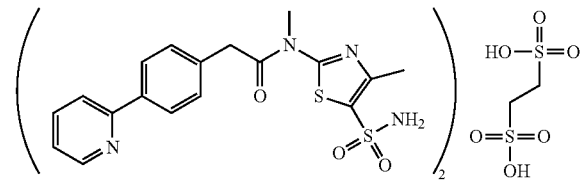

C$_{38}$H$_{42}$N$_8$O$_{12}$S$_6$
[995.18]

Synthesis Scheme of the Ethane-1,2-Disulfonic Acid Salt of the Free Base of Pritelivir.

General Process Description of the Ethane-1,2-disulfonic Acid Salt of the Free Base of Pritelivir All equivalents, volumes (L/kg) and weights (kg/kg) refer to the weight of starting material free base of pritelivir. In a 2.5 L sulfonation flask with overhead stirring the free base pritelivir (1 eq., 1 wt., 250.0 g) is suspended in water (4.0 vol.) and ethanol (4.0 vol.). The suspension is heated to 53° C. A solution of ethane-1,2-disulfonic acid (0.60 eq., 0.312 wt.) in water (0.31 vol.) is prepared and 15% of the solution is added to the suspension at 53° C. The suspension is seeded (0.02% w/w) and after 45 minutes the addition of the acid solution continued during 10 minutes. The suspension is stirred for 90 minutes at 53° C. and cooled down to 21° C. during 3 hours and stirred for 13 hours at said 21° C. The suspension is filtered and the filter cake is washed with a mixture of water (0.8 vol.) and ethanol (0.8 vol.). After deliquoring the filter cake on the filter the solid is transferred to a flask and dried on a rotovap (35° C., <20 mbar, 3 hours) to constant mass.

Results:
 IPC: 96.84% dry mass (160° C.).
 305.12 g crude ethane-1,2-disulfonic acid salt of the free base of pritelivir (98.7% yield not corrected for assay).
Characterisation of the ethane-1,2-disulfonic Acid Salt of the Free Base of Pritelivir
 Ethanol content by NMR: not detectable.
 Water content by Karl Fischer titration: 3.48% w/w (monohydrate 1.8%, dihydrate 3.5% w/w).
 Assay by NMR: 95.6% w/w as hemisulfonate.
 77.3% w/w as free base.
Specific Process Description of the Ethane-1,2-Disulfonic Acid Salt of the Free Base of Pritelivir
 Free base of pritelivir is suspended in 1 L Ethanol and 1 L water and heated to temperature of 54° C. 0.09 eq. of ethane-1,2 disulfonic acid (11.6 g) are dissolved in 11.6 g water and filtered over syringe filter. Said ethane-1,2 disulfonic acid solution is added to free base suspension during 1 min. Seeds of ethane-1,2 disulfonic acid salt are added. Suspension is stirred for 40 min. at 54° C. 0.51 eq. ethane-1,2-disulfonic acid (66.4 g) is dissolved in water (66 g, filtered over syringe filter) during 1 hour at 54° C. 90 min. stirring follows at 54° C. The mixture is allowed to cool down to room temperature and stirred for further 18 hours at room temperature. Filtering, washing with ethanol/water 1/1 (v/v, 0.4 L) and drying in vacuum follows.

Results:
 crude ethane-1,2 disulfonic acid salt: 305.1 g white solid (dry mass:96.8% (160° C.), no ethanol in NMR visible.
 Ethane-1,2-disulfonic acid content: 0.53 eq. (NMR)
 NMR: 95.6% w/w calculated as hemi salt.
 Karl Fischer: 3.48% w/w water
 Scale (purity): 250 g
 Product (% theory): 98.7 (uncorrected)

N-methyl-N-(4-methyl-5-sulfamoylthiazol-2-VI)-2-(4-(pyridin-2-yl)phenyl)acetamide benzenesulfonate salt of free base of pritelivir Process for the Manufacture of Benzene Sulfonic Acid Salt of Free Base of Pritelivir Free base of pritelivir

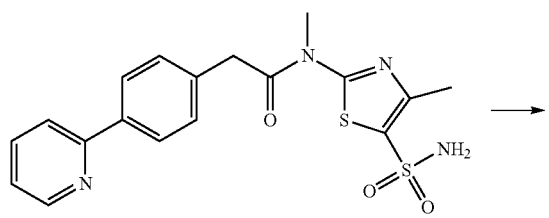

C₁₈H₁₈N₄O₃S₂
[402.49]

-continued
Benzenesulfonate salt of the free base of pritelivir

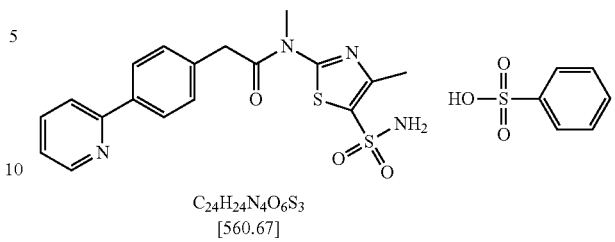

C₂₄H₂₄N₄O₆S₃
[560.67]

Synthesis Scheme of the Benzene Sulfonic Acid Salt of the Free Base of Pritelivir.
General Description of the Process for Manufacture of the Benzene Sulfonic Acid Salt of the Free Base of Pritelivir
 All equivalents, volumes (L/kg) and weights (kg/kg) refer to the weight of starting material pritelivir free base. In a 2.5 L sulfonation flask with overhead stirring, the free base of pritelivir (1 eq., 1 wt., 250.0 g) is suspended in water (4.0 vol.) and ethanol (4.0 vol.). The suspension is heated to 53° C. A solution of benzenesulfonic acid monoyhdrate (1.0 eq., 0.442 wt.) in water (0.15 vol.) is prepared and 15% of the solution is added to the suspension at 50° C. The suspension is seeded (0.02% w/w) and after 30 minutes the addition of the acid solution continues during 90 minutes. The suspension is cooled down to 21° C. during 3 hours and stirred for 14 hours at 21° C. The suspension is filtered and the filter cake is washed with a mixture of water (0.8 vol.) and ethanol (0.8 vol.). After deliquoring the filter cake on the filter, the solid is transferred to a flask and dried on a rotovap (35° C., <20 mbar, 4 h) to constant mass.

Results:
 IPC: 99.63% dry mass (160° C.).
 322.51 g crude benzene sulfonic acid salt of the free base of pritelivir (92.6% yield not corrected for assay).
Characterisation of the Benzene Sulfonic Acid Salt of the Free Base of Pritelivir
 Ethanol content by NMR: 500 ppm
 Water content by Karl Fischer titration: 0.17% w/w (monohydrate 3.1% w/w)
 Assay by NMR: 102.1% w/w as benzenesulfonate
 73.4% w/w as free base
Specific Description of the Process of Benzene Sulfonic Acid Salt of the Free Base of Pritelivir
 Free base of pritelivir is suspended in 1 L Ethanol and 1 L water and heated to a temperature of 52° C. 0.15 eq. benzene sulfonic acid (16.4 g) is added as solution in water (6.3 g) during 1 min. Seeds of benzene sulfonic acid salt of the free base of pritelivir are added and stirred for 30 min. at temperature of 52° C. 0.85 eq. benzene sulfonic acid (94.0 g) is added as a solution in water (30.5 g) during 90 min. This mixture is allowed to cool down to room temperature. Further stirring for about 18 hours at room temperature follows. Filtering, washing with 0.4 L ethanol/water 1/1 (v/v) and drying in vacuum follows.

Results:
 crude benzene sulfonic acid salt of the free base of pritelivir:322.5 g white solid (dry mass:99.6% (160° C.)
 500 ppm Ethanol
 Benzene sulfonic acid content: 0.93 eq. (NMR)
 NMR: 102.1% w/w calculated as monosulfate
 TGA: 0.15% weight loss
 Karl Fischer: 0.17% w/w water
 Scale (purity): 250 g
 Product (% theory): 92.6 (uncorrected)

N-methyl-N-(4-methyl-5-sulfamoylthiazol-2-yl)-2-(4-(pyridin-2-yl)phenyl)acetamide ethanesulfonate Salt of Free Base of Pritelivir Process for the Manufacture of an Ethane Sulfonic Acid Salt of Free Base of Pritelivir

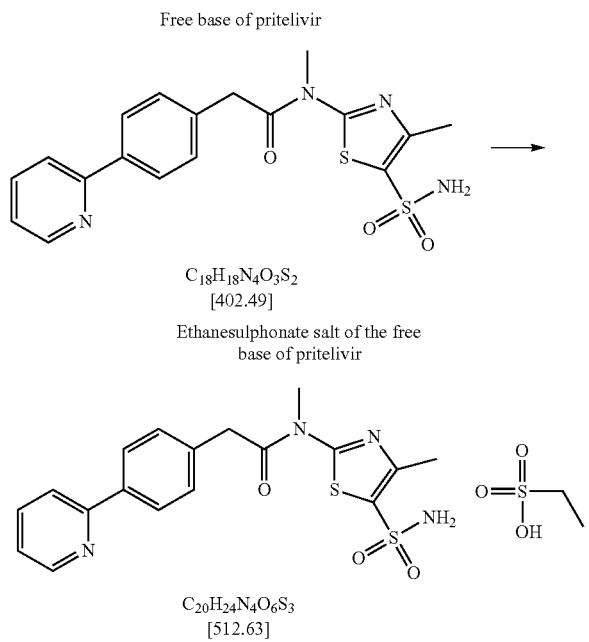

Scheme of the Synthesis of an Ethane Sulfonic Acid Salt of Free Base of Pritelivir.

General Description of the Process of Manufacture of an Ethane Sulfonic Acid Salt of Free Base of Pritelivir All equivalents, volumes (L/kg) and weights (kg/kg) refer to the weight of starting material free base of pritelivir. In a 2.5 L sulfonation flask with overhead stirring free base of pritelivir (1 eq., 1 wt., 250.0 g) is suspended in water (4.0 vol.) and ethanol (4.0 vol.). The suspension is heated to 55° C. Ethanesulfonic acid (1.56 eq., 0.427 wt.) is dissolved in water (0.43 vol.) and added during 50 minutes. The suspension is allowed to cool down during 3 hours to 21° C. (at around 38° C. a thick suspension is may be formed) and further stirring for 14 hours at 21° C. follows. The suspension is filtered and the filter cake is washed with a mixture of water (0.8 vol.) and ethanol (0.8 vol.). After deliquoring the filter cake on the filter, the solid is transferred to a flask and dried on a rotovap (35° C., <20 mbar, 4 hours) to constant mass.

Results:
IPC: 96.31% dry mass (160° C.).
314.28 g crude ethane sulfonic acid salt of free base of pritelivir (98.7% yield not corrected for assay).

Characterisation:
Ethanol content by NMR: 220 ppm
Water content by Karl Fischer titration: 3.35% w/w (monohydrate 3.4% w/w)
Assay by NMR: 95.0% w/w as maleate
72.1% w/w as free base Specific Description of the Process for Manufacture of Ethane Sulfonic Acid Salt of Free Base of Pritelivir Free base of pritelivir is suspended in 1 L Ethanol and 1 L water and heated to temperature of 60° C. 1.56 eq. ethane sulfonic acid (106.8 g) is dissolved in water (107 g) and added during 50 minutes to the suspension. The suspension is allowed to cool down to room temperature and further stirred for 18 hours. Filtering, washing with 0.4 L ethanol/water 1/1 (v/v) and drying in vacuum follows.

Results:
crude ethane sulfonic acid salt of free base of pritelivir: 314.3 g white solid (dry mass:96.3% (160° C.)
200 ppm Ethanol (NMR)
1 eq. ethane sulfonic acid (NMR)
NMR: 95.0% w/w calculated as mono esylate
TGA: 3.46% weight loss
Karl Fischer: 3.35% w/w water
Scale (purity): 250 g
Product (% theory): 98.7 (uncorrected)

CONCLUSION

Besides the maleate salt of the free base of pritelivir of the invention, the inventors further surprisingly found 4 additional salts, which:
i) all are crystalline,
ii) all include water,
iii) according to NMR data have no residual ethanol present which would be outside the specifications
iv) DSC indicates possible form changes for all salts, and
v) all identified salt forms of the invention are physicochemically stable for 4 weeks at 40° C./75% relative humidity.

With the above context, the following consecutively numbered embodiments provide other specific aspects of the invention:

1. A maleate salt of the free base of N-[5-(amino-sulfonyl)-4-methyl-1,3-thiazol-2-yl]-N-methyl-2-[4-(2-pyridinyl)phenyl]acetamide.
   In addition to embodiment 1, the present invention also provides for a sulfate-, hemiethane-1,2-disulfonate-, benzenesulfonate-, and ethanesulfonate salt of the free base of pritelivir.

2. The maleate salt according to embodiment 1, wherein said maleate salt is characterised by a photostability of at least 70% residual free base of N-[5-(amino-sulfonyl)-4-methyl-1,3-thiazol-2-yl]-N-methyl-2-[4-(2-pyridinyl)phenyl]acetamide after light exposure with wavelengths ranging as of from 300 nm to 800 nm, and with a light exposure quantity of at least 1.2 million Lux hours, and with a light exposure energy of at least 200 Wh/m$^2$ over at least 29 hours when said photostability is determined by using a compendial method as per "Ph. Eur" and/or "USP" methods.

3. The maleate salt according to any one of the preceding embodiments, wherein said maleate salt is further characterised by having characteristic XRPD peaks at 6.6, 15.9, 16.2, 18.1, 20.5, 22.5, 26.1, and 28.6 2theta when determined by using a compendial method as per "Ph. Eur" and/or "USP" methods.

4. The maleate salt according to any one of the preceding embodiments, wherein said maleate salt is physicochemical stable characterised by recoveries of said maleate salt of the start concentration of at least 85% after two weeks storage at room temperature and at a pH as of from 3.5-7.0 in aqueous solution when determined by using a compendial method as per "Ph. Eur" and/or "USP" methods.

5. The maleate salt according to any one of the preceding embodiments, wherein said maleate, salt is characterised by solubility in water of about 0.48 mg/mL when determined by using a compendial method as per "Ph. Eur" and/or "USP" methods.
6. A pharmaceutical composition comprising a maleate salt according to any one of the preceding embodiments, wherein said pharmaceutical composition further comprises at least one pharmaceutically acceptable excipient.
   In addition to embodiment 6, likewise, pharmaceutical formulations as disclosed herein are provided for the sulfate-, hemiethane-1,2-disulfonate-, benzenesulfonate-, and ethanesulfonate salt of the free base of pritelivir.
7. A photostable pharmaceutical composition obtainable by formulating the maleate salt as defined in any of the embodiments 1 to 5 with at least one pharmaceutically acceptable excipient.
8. The pharmaceutical composition according to any of the embodiments 6 or 7, further comprising another pharmaceutically active ingredient selected from the group comprising anti-inflammatory agents, anti-viral agents, centrally and peripherally acting analgesics, (local) anesthetics.
   In addition to embodiment 8, likewise, the herein disclosed sulfate-, hemiethane-1,2-disulfonate-, benzenesulfonate-, and ethanesulfonate salts of the free base of pritelivir may be also combined in pharmaceutical formulations with another pharmaceutically active ingredient selected from the group comprising anti-inflammatory agents, anti-viral agents, centrally and peripherally acting analgesics, (local) anesthetics.
9. The pharmaceutical composition according to embodiment 8, wherein said local anesthetic is lidocaine.
10. The pharmaceutical composition according to any of the embodiments 6 to 8, further comprising an ultraviolet radiation blocking agent selected from a group comprising Octisalate, titanium dioxide, zinc oxide, PABA, homosalate, trolamine salicylate, Dioxybenzone, sulisobenzone, oxybenzone, avobenzone, ecasmule, meradimate, cinoxate, octocrylene.
    In addition to embodiment 10, likewise, the herein disclosed sulfate-, hemiethane-1,2-disulfonate-, benzenesulfonate-, and ethanesulfonate salts of the free base of pritelivir may be also combined in pharmaceutical formulations with an ultraviolet radiation blocking agent selected from a group comprising Octisalate, titanium dioxide, zinc oxide, PABA, homosalate, trolamine salicylate, Dioxybenzone, sulisobenzone, oxybenzone, avobenzone, ecasmule, meradimate, cinoxate, octocrylene.
11. A topical pharmaceutical formulation comprising the maleate salt as defined in any of the embodiments 1 to 5, and wherein said formulation is further comprising formulations for patch administration, creames, ointments, salves, gels, skin lotions, wax formulations, lippsticks, tonics, mousses, foam, films, emulsions, paste, solutions, oils, and lipogels.
    In addition to embodiment 11, in another aspect of the invention also the sulfate-, hemiethane-1,2-disulfonate-, benzenesulfonate-, and ethanesulfonate salts of the free base of pritelivir may be further comprised in formulations for patch administration, creames, ointments, salves, gels, skin lotions, wax formulations, lipsticks, tonics, mousses, foam, films, emulsions, paste, solutions, oils, and lipogels.
12. The topical pharmaceutical formulation as defined in embodiment 11, wherein the said maleate salt has a mean percentage recovery of about 95 to 105% when measured according to ICH guideline Q1B.
13. The topical pharmaceutical formulation as defined in any one of the embodiments 11 to 12, wherein the said maleate salt has a mean purity ranging from 95 to 105%, preferably of about 100% area/area as measured according to ICH guideline Q1B.
14. The pharmaceutical composition or topical pharmaceutical formulation as defined in any one of the embodiments 6 to 13, wherein the said maleate salt is present in dissolved form in an amount of 0.1 to 10% w/w when determined by using a compendial method as per "Ph. Eur" and/or "USP" methods.
15. The pharmaceutical composition or topical pharmaceutical formulation as defined in any one of the embodiments 6 to 14, wherein the maleate salt is present in an amount of 3.0 to 8% w/w when determined by using a compendial method as per "Ph. Eur" and/or "USP" methods.
16. The pharmaceutical composition or topical pharmaceutical formulation as defined in any one of the embodiments 6 to 15, wherein the maleate salt is present in an amount of 4 to 7% w/w when determined by using a compendial method as per "Ph. Eur" and/or "USP" methods.
17. The pharmaceutical composition or topical pharmaceutical formulation as defined in any one of the embodiments 6 to 16, wherein the maleate salt is present in an amount of 5.0% w/w when determined by using a compendial method as per "Ph. Eur" and/or "USP" methods.
18. The topical pharmaceutical formulation as defined in any one of embodiments 11 to 17, wherein the maleate salt is present in an amount of 1.0 to 10% w/w, particularly 5.0% w/w, and wherein the topical pharmaceutical formulation is an ointment, and wherein said ointment is administered 1 to 10 times a day, or 2 to 10 times a day, or 3 to 8 times a day, or 3 to 7 times a day, or 4 to 6 times a day, or 5 times a day.
19. The topical pharmaceutical formulation as defined in any one of embodiments 11 to 18, wherein the maleate salt is present in an amount of 1.0 to 7.5% w/w, particularly 5.0% w/w, and wherein the topical pharmaceutical formulation is an ointment, and wherein said ointment is administered 1 to 10 times a day, or 2 to 10 times a day, or 3 to 8 times a day, or 3 to 7 times a day, or 4 to 6 times a day, or 5 times a day, and wherein the ointment is administered over a period of 2 to 14 day, 3 to 10 days, 3 to 7 days, 4 to 5 days, or over 5 days, or over 4 days.
20. The topical pharmaceutical formulation as defined in any one of embodiments 1,1 to 19, and wherein the maleate salt is present in an amount of 5.0% w/w, wherein the topical pharmaceutical formulation is an ointment, and wherein said ointment is administered 5 times a day, and wherein the ointment is administered over a period of 4 days.
    In an adjacent embodiment to embodiment 20, said maleate salt is present in an amount of 5.0% w/w, wherein the topical pharmaceutical formulation is a gel, and wherein said gel is administered 5 times a day, and wherein the gel is administered over a period of 4 days.

In an adjacent embodiment to embodiment 20, said maleate salt is present in an amount of 5.0% w/w, wherein the topical pharmaceutical formulation is a cream, and wherein said cream is administered 5 times a day, and wherein the cream is administered over a period of 4 days.

In addition to embodiment 20, also the sulfate-, hemiethane-1,2-disulfonate-, benzenesulfonate-, and ethanesulfonate salts of the free base of pritelivir are present in an amount of 5.0% w/w, wherein the topical pharmaceutical formulation is either an ointment, a gel, or a cream and wherein either said ointment, gel or cream is administered 5 times a day, and wherein either said ointment, gel or cream is administered over a period of 4 days.

21. The topical pharmaceutical formulation as defined in any one of embodiments 11 to 20, wherein the maleate salt is present in an amount sufficient to reach a concentration of at least ≥10 nM in the epidermis and dermis after at least 1 hour of application to an individual subjected in a method of topical treatment with said composition when determined by using a compendial method as per "Ph. Eur" and/or "USP" methods.

22. The topical pharmaceutical formulation as defined in any one of embodiments 11 to 21, wherein the topical pharmaceutical formulation has an apparent pH as of from 3.5 to 7.0, particularly as of from 4.0 to 5.0, when determined by using a compendial method as per "Ph. Eur" and/or "USP" methods.

23. The topical pharmaceutical formulation as defined in any one of embodiments 11 to 22, wherein the maleate salt has a physico-chemical stability of at least 85% after two weeks storage at room temperature and at an apparent pH as of from 3.5-7.0, particularly as of from 4.0 to 5.0, when determined by using a compendial method as per "Ph. Eur" and/or "USP" methods.

24. The maleate salt according to any of the embodiments 1 to 5 for use as a medicament.

In addition to embodiment 24, also the sulfate-, hemiethane-1,2-disulfonate-, benzenesulfonate-, and ethanesulfonate salts of the free base of pritelivir are provided for use as a medicament.

25. The maleate salt according to any of the embodiments 1 to 5 for use in a method of treatment and/or prevention of herpes virus infections.

In addition to embodiment 25, also the sulfate-, hemiethane-1,2-disulfonate-, benzenesulfonate-, and ethanesulfonate salts of the free base of pritelivir are provided for use in a method of treatment and/or prevention of herpes virus infections.

26. The maleate salt according to any of the embodiments 1 to 5 for use in a method of treatment and/or prevention of herpes virus infections, wherein said herpes viruses are selected from the order of simplex viruses.

In addition to embodiment 26, also the sulfate-, hemiethane-1,2-disulfonate-, benzenesulfonate-, and ethanesulfonate salts of the free base of pritelivir are provided for the use in a method of treatment and/or prevention of herpes virus infections, wherein said herpes viruses are selected from the order of simplex viruses.

27. The maleate salt for the use according to any of the embodiments 25 to 26, wherein said simplex virus is selected from Herpes Simplex Virus 1 and Herpes Simplex Virus 2.

In addition to embodiment 27, also the sulfate-, hemiethane-1,2-disulfonate-, benzenesulfonate-, and ethanesulfonate salts of the free base of pritelivir are provided for the use in a method of treatment and/or prevention of herpes virus infections, wherein said herpes viruses are selected from the order of simplex viruses.

28. A method of treatment or suppression of the incidence of a herpes simplex virus subtype 1 or 2 infection, or suppression of transmission of a herpes simplex virus subtype 1 or 2 infection, comprising administering to a subject in need thereof an effective amount of a maleate salt of the free base of N-[5-(aminosulfonyl)-4-methyl-1,3-thiazol-2-yl]-N-methyl-2-[4-(2-pyridinyl)-phenyl] as defined in the embodiments 1 to 5.

In addition to embodiment 28, a method of treatment or suppression of the incidence of a herpes simplex virus subtype 1 or 2 infection, or suppression of transmission of a herpes simplex virus subtype 1 or 2 infection is provided, comprising administering to a subject in need thereof an effective amount of a salt selected from a group comprising a sulfate-, a hemiethane-1,2-disulfonate-, a benzenesulfonate-, and a ethanesulfonate salt of the free base of pritelivir as disclosed herein.

29. The maleate salt according to any of the embodiments 1 to 5 for use in an oral pharmaceutical formulation in the treatment of a subject in need thereof.

In addition to embodiment 29, also the sulfate-, hemiethane-1,2-disulfonate-, benzenesulfonate-, and ethanesulfonate salts of the free base of pritelivir are provided for use in an oral pharmaceutical formulation in the treatment of a subject in need thereof.

30. The maleate salt according to any of the embodiments 1 to 5 for use in a oral pharmaceutical formulation in the treatment and/or prevention of a herpes, virus infection, particularly of herpes simplex infections, in a subject in need thereof.

In addition to embodiment 30, also the sulfate-, hemiethane-1,2-disulfonate-, benzenesulfonate-, and ethanesulfonate salts of the free base of pritelivir are provided for use in a oral pharmaceutical formulation in the treatment and/or prevention of a herpes virus infection, particularly of herpes simplex infections, in a subject in need thereof.

31. The maleate salt according to any of the embodiments 1 to 5 for use in a topical pharmaceutical formulation in the treatment of a subject in need thereof.

In addition to embodiment 31, also the sulfate-, hemiethane-1,2-disulfonate-, benzenesulfonate-, and ethanesulfonate salts of the free base of pritelivir are provided for use in a topical pharmaceutical formulation in the treatment of a subject in need thereof.

32. The maleate salt according to any of the embodiments 1 to 5 for use in topical administration to a subject in need thereof, wherein said topical administration is comprising the application to skin and mucosal surfaces, e.g. facial application, application to the mouth, the genitals, and the eyes.

In addition to embodiment 32, also the sulfate-, hemiethane-1,2-disulfonate-, benzenesulfonate-, and ethanesulfonate salts of the free base of pritelivir are provided for use in topical administration to a subject in need thereof, wherein said topical administration is comprising the application to skin and mucosal surfaces, e.g. facial application, application to the mouth, the genitals, and the eyes.

33. The maleate salt according to any of the embodiments 1 to 5 for use in systemic administration to a subject in need thereof.
   In addition to embodiment 33, also the sulfate-, hemiethane-1,2-disulfonate-, benzenesulfonate-, and ethanesulfonate salts of the free base of pritelivir are provided for use in systemic administration to a subject in need thereof.
34. The maleate salt according to any of the embodiments 1 to 5 for use in a method of treatment and/or prevention of recurrent herpes labialis.
   In addition to embodiment 34, also the sulfate-, hemiethane-1,2-disulfonate-, benzenesulfonate-, and ethanesulfonate salts of the free base of pritelivir are provided for use in a method of treatment and/or prevention of recurrent herpes labialis.
35. The maleate salt according to any of the embodiments 1 to 5 for use in a method of treatment and/or prevention of recurrent herpes labialis selected from the group of patients showing signs of the prodromal stage of herpes labialis, patients having erythema, patients showing labial papules, patients having labial vesicles, patients with labial ulcers and/or soft crusts, patients having labial hard crusts, patients having residual labial erythema.
   In addition to embodiment 35, also the sulfate-, hemiethane-1,2-disulfonate-, benzenesulfonate-, and ethanesulfonate salts of the free base of pritelivir are provided for use in a method of treatment and/or prevention of recurrent herpes labialis selected from the group of patients showing signs of the prodromal stage of herpes labialis, patients having erythema, patients showing labial papules, patients having labial vesicles, patients with labial ulcers and/or soft crusts, patients having labial hard crusts, patients having residual labial erythema.
36. The maleate salt according to any of the embodiments 1 to 5 for use in a method of treatment and/or prevention of herpes genitalis.
37. The maleate salt according to any of the embodiments 1 to 5 for use in the treatment and/or prevention of herpes keratitis
38. The maleate salt according to any of the embodiments 1 to 5 for use in the treatment and/or prevention of herpes meningitis and/or encephalitis.
39. The maleate salt according to any of the embodiments 1 to 5 for use in the treatment and/or prevention of herpes infections in newborns.
40. The maleate salt according to any of the embodiments 1 to 5 for use in the treatment and/or prevention of herpes infections in the immunocompetent and/or immunocompromised individuals.
   Likewise, in addition the subject matter of the embodiments 36 to 40 also applies to the sulfate-, hemiethane-1,2-disulfonate-, benzenesulfonate-, and ethanesulfonate salts of the free base of pritelivir.
41. The maleate salt according to any of the embodiments 1 to 5, wherein the immunocompromised individuals are selected from the group comprising recipients of an organ transplant, individuals having an infection by another virus or bacterium, particularly an infection with HIV and/or another herpes virus, and individuals infected with a herpes simplex virus that is resistant to at least one anti-viral active.
42. A method of treatment and/or prophylaxis of a herpes virus infection comprising administering a maleate salt according to any of the embodiments 1 to 5 to a subject in need thereof.
   In addition to embodiment 42, also the sulfate-, hemiethane-1,2-disulfonate-, benzenesulfonate-, and ethanesulfonate salts of the free base of pritelivir are provided for the aforementioned uses and methods of treatments.
43. A process for the manufacture of the maleate salt of the free base of N-[5-(amino-sulfonyl)-4-methyl-1,3-thiazol-2-yl]-N-methyl-2-[4-(2-pyridinyl)phenyl]acetamide as defined in the embodiments 1 to 5, said process comprising the steps of:
   i) providing a mixing means, preferably a mixing means with overhead stirring,
   ii) filling said mixing means of step i) with 460 to 490 g free base of pritelivir,
   iii) suspending the free base of pritelivir of step ii) with 3 to 5 volumes of water,
   iv) heating the suspension of step iii) to 45 to 55° C. by suitable heating means,
   v) adding 225 to 240 g of maleic acid in solid form over a time period of 40 to 90 min. until resultant solution is obtained,
   vi) cooling the solution obtained under step v) down towards 44 to 52° C.
   vii) seeding an aliquot of the solution of step vi) with a crude maleate salt of the free base of pritelivir,
   viii) over a period as of from 1.5 to 2.5 hours the resultant suspension of step vii) is allowed to cool down towards 18 to 24° C.,
   ix) stirring the suspension of step viii) overnight follows,
   x) the suspension of step ix) was filtered, so to obtain a resultant filter cake,
   xi) the solid filter cake obtained under step x) is transferred to a mixing means, preferably a flask,
   xii) rotary evaporation of the mixing means of step xi) follows for 25 to 32 hours while applying the following conditions:
      a. an ambient temperature of 30 to 40° C.,
      b. a pressure of 15 to 25 mbar,
      so to obtain a constant mass,
   xiii) homogenisation follows, preferably homogenisation with mortar and pastle follows,
   xiv) so to obtain a maleate salte of the free base of pritelivir in accordance with the invention.
44. The process of embodiment 43, comprising the steps of:
   i) providing a mixing flask with overhead stirring,
   ii) filling said mixing flask of step i) with about 475.4 g free base of pritelivir,
   iii) suspending the free base of pritelivir of step ii) with about 4 volumes of water,
   iv) heating the suspension of step iii) to about 51° C. by suitable heating means,
   v) adding about 232 g of maleic acid in solid form over a time period of about 60 min. until resultant solution is obtained,
   vi) cooling the solution obtained under step v) down towards about 48° C.,
   vii) seeding an aliquot of the solution of step vi) with a crude maleate salt of the free base of pritelivir,
   viii) over a period of about 2 hours the resultant suspension of step vii) is allowed to cool down towards about 21° C., ix) stirring the suspension of step viii) overnight follows, x) the suspension of step ix) was filtered, so to obtain a resultant filter cake, xi) the solid filter cake obtained under step x) is transferred to a mixing means, preferably a flask, xii) rotary evaporation of the mixing means of step xi) follows for about 28 hours while applying the following conditions:
  a. an ambient temperature of about 35° C.,
  b. a pressure of about 20 mbar,
  so to obtain a constant mass, xiii) homogenisation follows, preferably homogenisation with mortar and pastle follows, xiv) so to obtain a maleate salte of the free base of pritelivir in accordance with the invention.

BRIEF DESCRIPTION OF THE DRAWINGS

FIG. 1: Representative characteristic properties of a maleate salt of the free base of pritelivir of the invention.

FIG. 10: The table of FIG. 10 shows a peak list of the PXRD pattern of the maleate salt of the free base of pritelivir as further depicted in FIG. 11. The characteristic peaks for the said maleate salt have been highlighted therein.

FIG. 13: Peak list of the $^1$H-NMR spectrum of the maleate salt of the free base of pritelivir of FIG. 12. Legend: s=singlet; d=doublet; t=triplet; m=multiplet.

FIG. 15: Peak list of the $^{13}$C-NMR spectrum (proton decoupled) of the maleate salt of the free base of pritelivir of FIG. 14. Legend: s=singlet; d=doublet; t=triplet; m=multiplet.

FIG. 17: Peak list of the FT-IR spectrum of the maleate salt of the free base of pritelivir of FIG. 16. Legend: s=sharp; b=broad; st=strong; me=medium; we=weak.

FIG. 21: Relevant peaks in the MS spectrum of the maleate salt of the free base of pritelivir of FIG. 20.

FIG. 47: Solubility properties in terms of FaSSGF, FaSSIF and FeSSIF comparison of the test items: free base of pritelivir, mesylate salt thereof, sulfonate salt thereof, maleate salt thereof, esylate salt thereof, mono benzenesulfonate thereof, hemi ethane-1,2,-disulfonate.

FIG. 48: Solubility comparison of the test items in water: free base of pritelivir, mesylate salt thereof, sulfonate salt thereof, maleate salt thereof, esylate salt thereof, mono benzenesulfonate thereof, hemi ethane-1,2,-disulfonate.

FIG. 49: Solubility comparison of the test items in different pharmaceutical excipients: free base of pritelivir, mesylate salt thereof, sulfonate salt thereof, maleate salt thereof, esylate salt thereof, mono benzenesulfonate thereof, hemi ethane-1,2,-disulfonate.

FIG. 50: Stability comparison of the test items in different pharmaceutical excipients when stored for two weeks at ambient temperature: free base of pritelivir, mesylate salt thereof, sulfonate salt thereof, maleate salt thereof, esylate salt thereof, mono benzenesulfonate thereof, hemi ethane-1,2,-disulfonate.

FIG. 51: Stability comparison of the test items in different pharmaceutical excipients when stored for two weeks at 50° C.: free base of pritelivir, mesylate salt thereof, sulfonate salt thereof, maleate salt thereof, esylate salt thereof, mono benzenesulfonate thereof, hemi ethane-1,2,-disulfonate.

FIG. 52: Peak % area of irradiated solutions of the test items and dark control: free base of pritelivir, mesylate salt thereof, sulfonate salt thereof, maleate salt thereof, esylate salt thereof, mono benzenesulfonate thereof, hemi ethane-1,2,-disulfonate.

FIG. 53: Peak % area of irradiated solutions of the test items and dark control: free base of pritelivir, mesylate salt thereof, sulfonate salt thereof, maleate salt thereof, esylate salt thereof, mono benzenesulfonate thereof, hemi ethane-1,2,-disulfonate.

Figure 2:
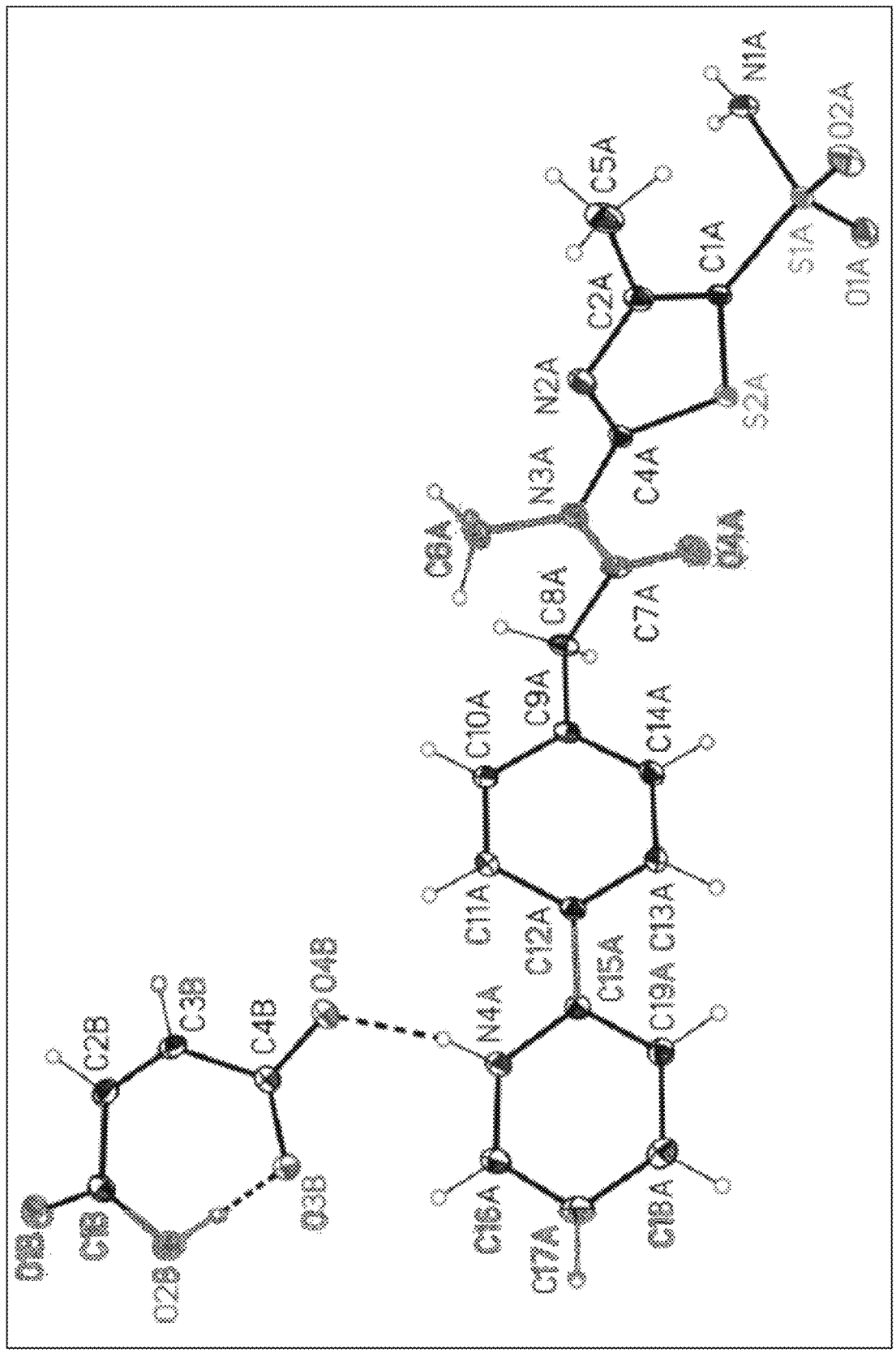
FIG. 2: An Ortep plot of a maleate salt of the free base of pritelivir. Crystal Structure of a maleate salt of the free base of pritelivir (code: P071-02-ACE-11-01-SCXRD-01). Thermal ellipsoids are shown with an electron density set at 50% probability level.
Figure 3:
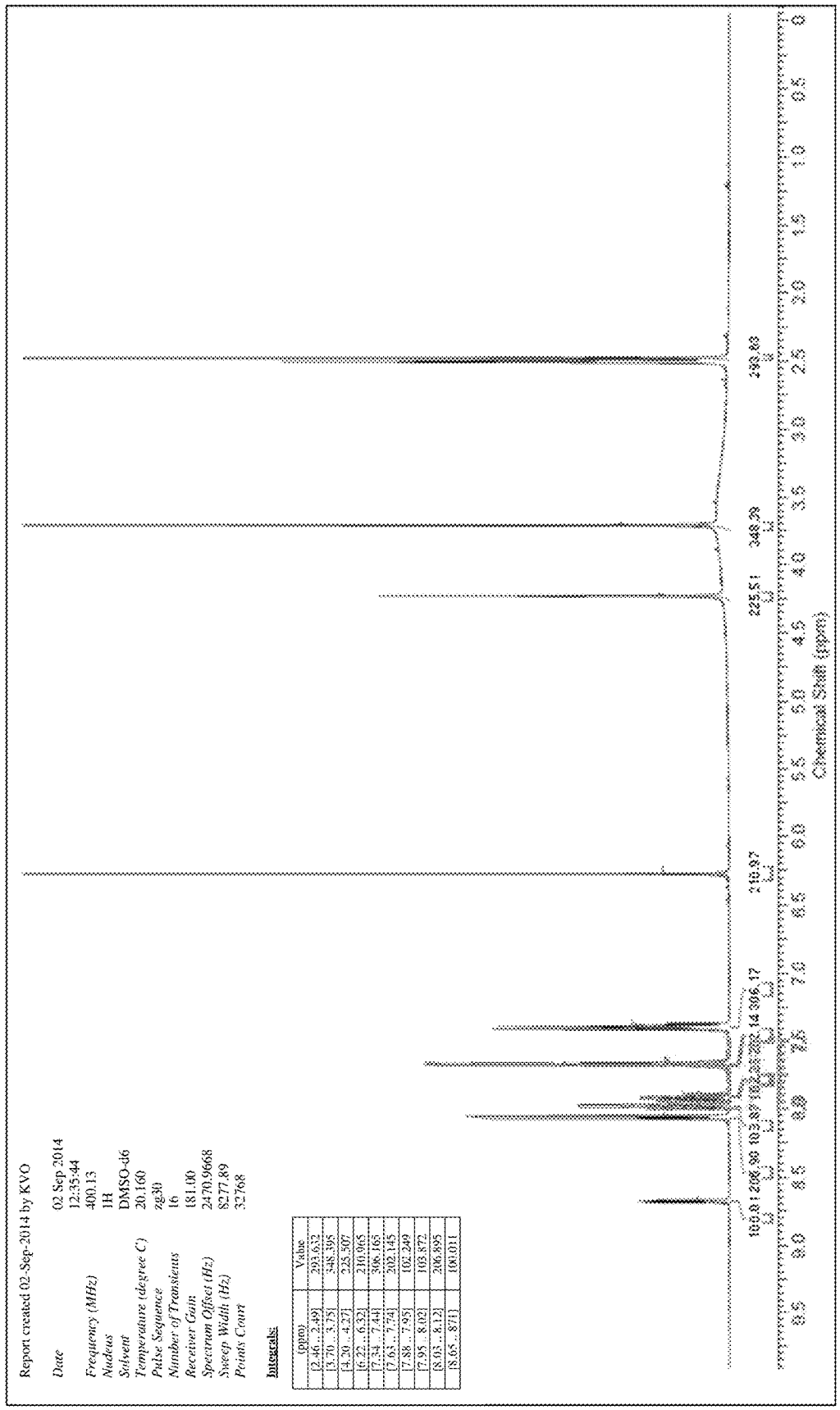
FIG. 3: $^1$H NMR spectrum of a maleate salt of the free base of pritelivir in accordance with the invention.
Figure 4:
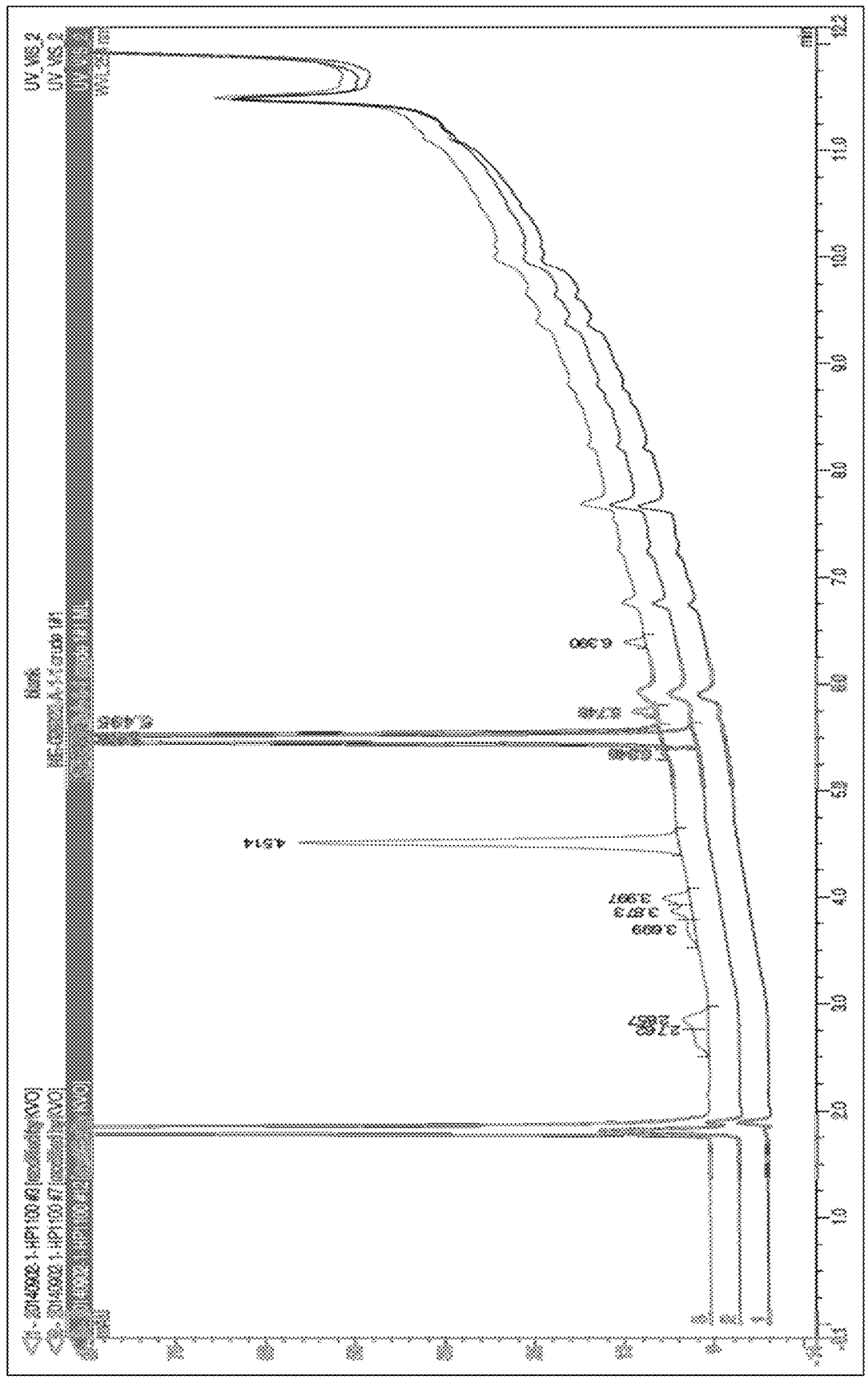
FIG. 4: HPLC overlay of a maleate salt of the free base of pritelivir (middle, 100.0% a/a); with corresponding mother liquor (top, 75.64% a/a) and blank (bottom).
Figure 5:
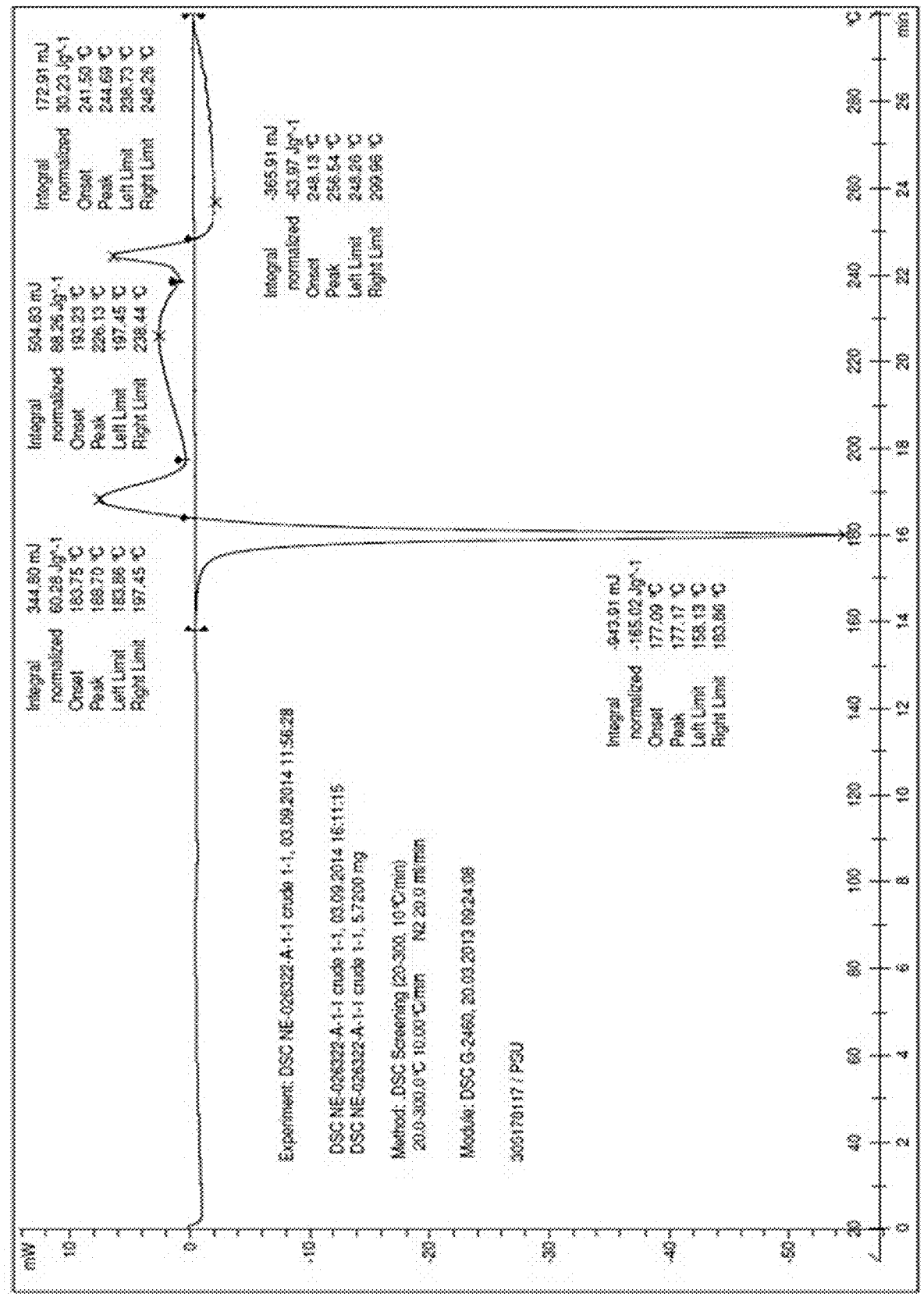
FIG. 5: DSC of a maleate salt of the free base of pritelivir in accordance with the invention. Melting endotherm at 177° C.
Figure 6:
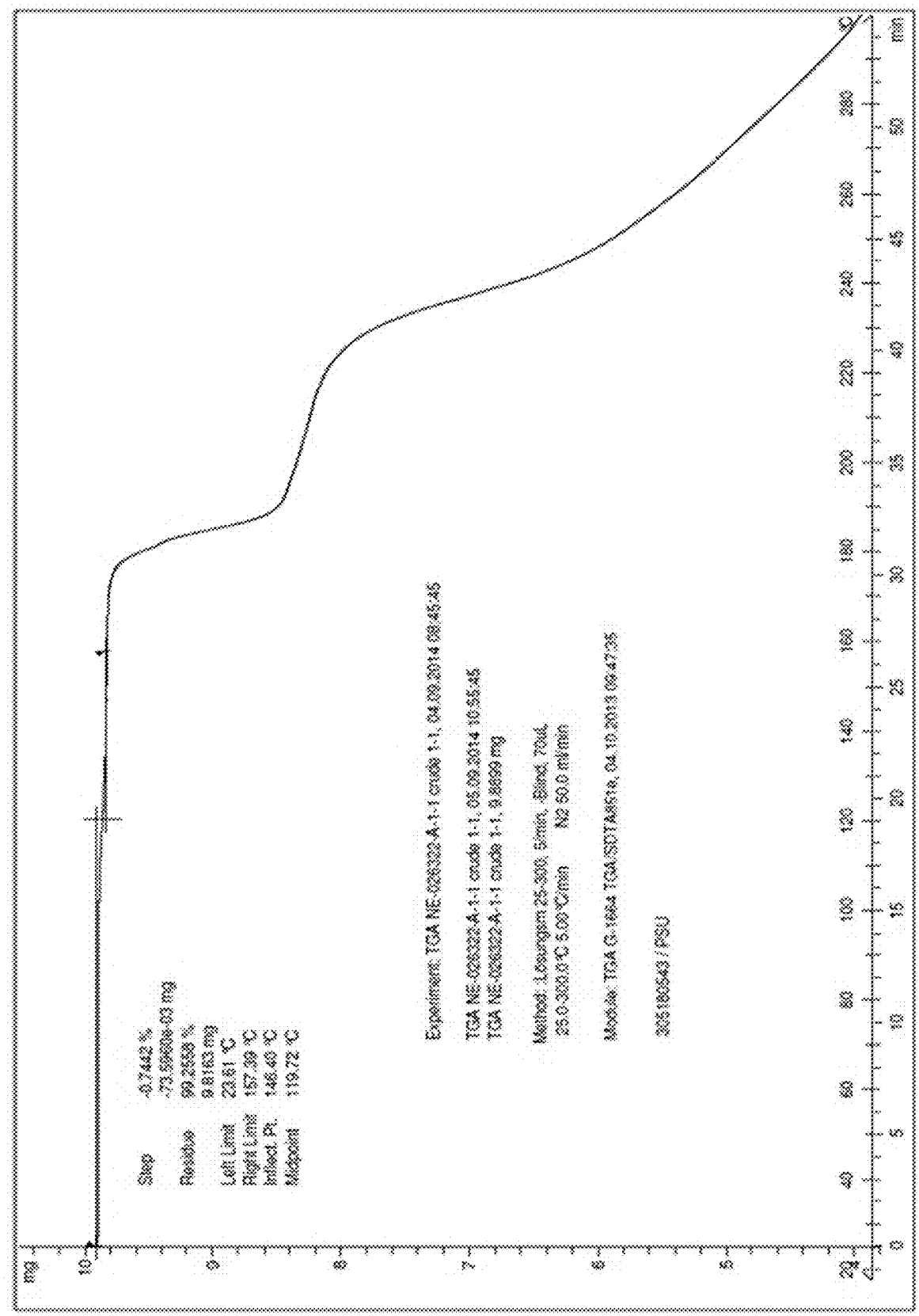
FIG. 6: TGA of a maleate salt of the free base of pritelivir in accordance with the invention with a weight loss of 0.74% w/w up to 150° C. The next steps indicates decomposition of maleic acid in the melt.
Figure 7:
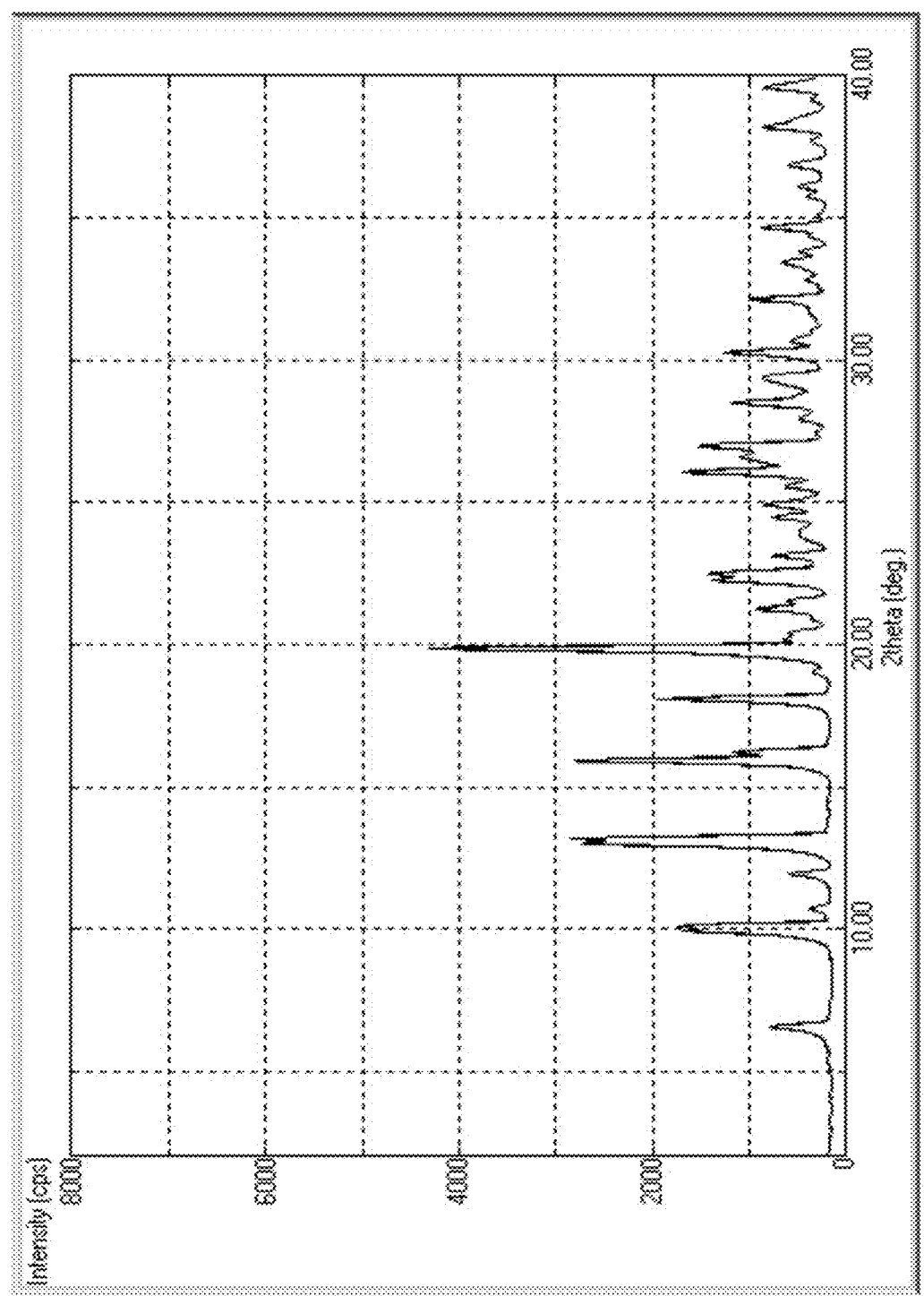
FIG. 7: XRPD of a maleate salt of the free base of pritelivir in accordance with the invention, which shows a crystalline form.
Figure 8:
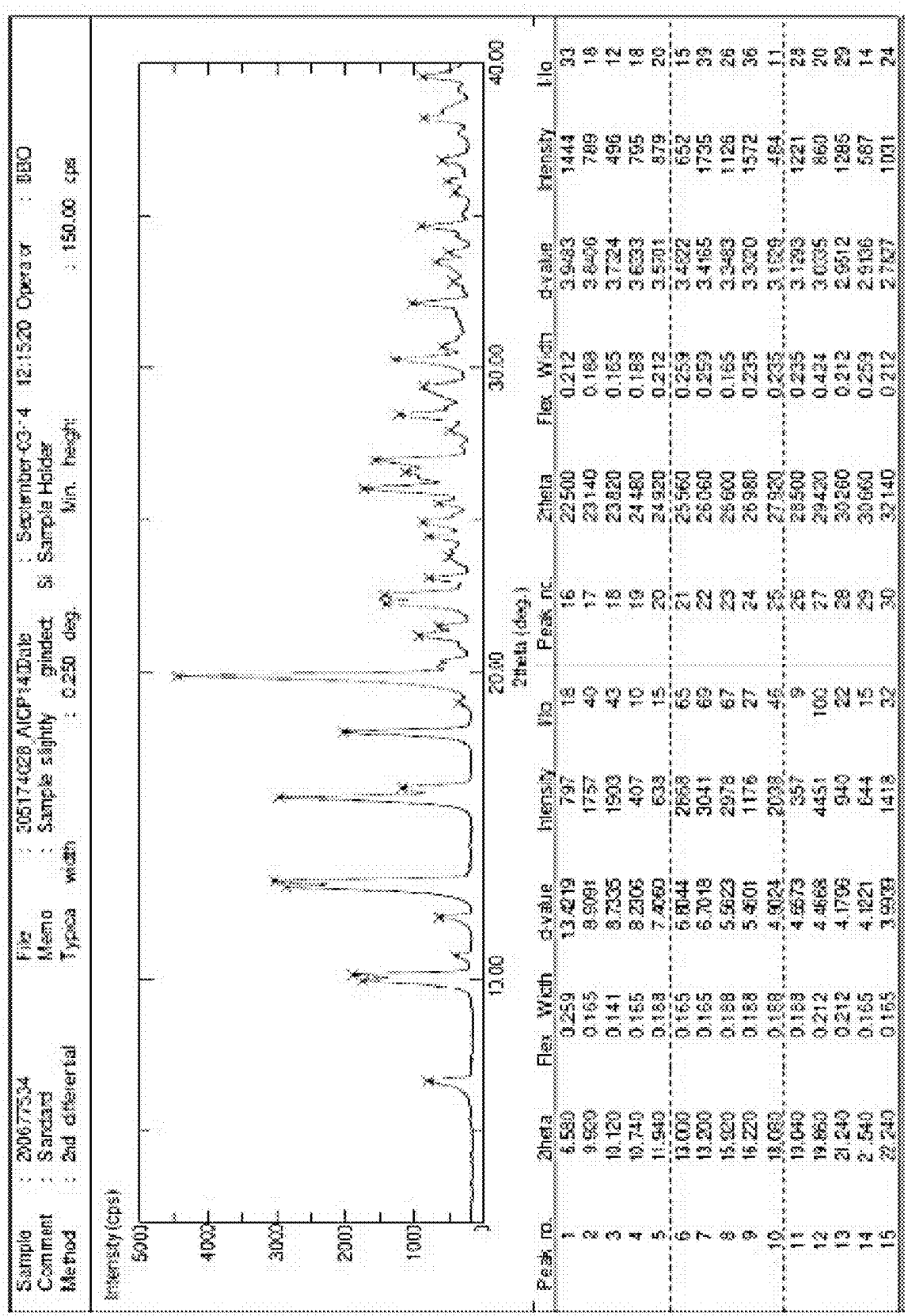
FIG. 8: XRPD data for a maleate salt of the free base of pritelivir in accordance with the invention.
Figure 9:
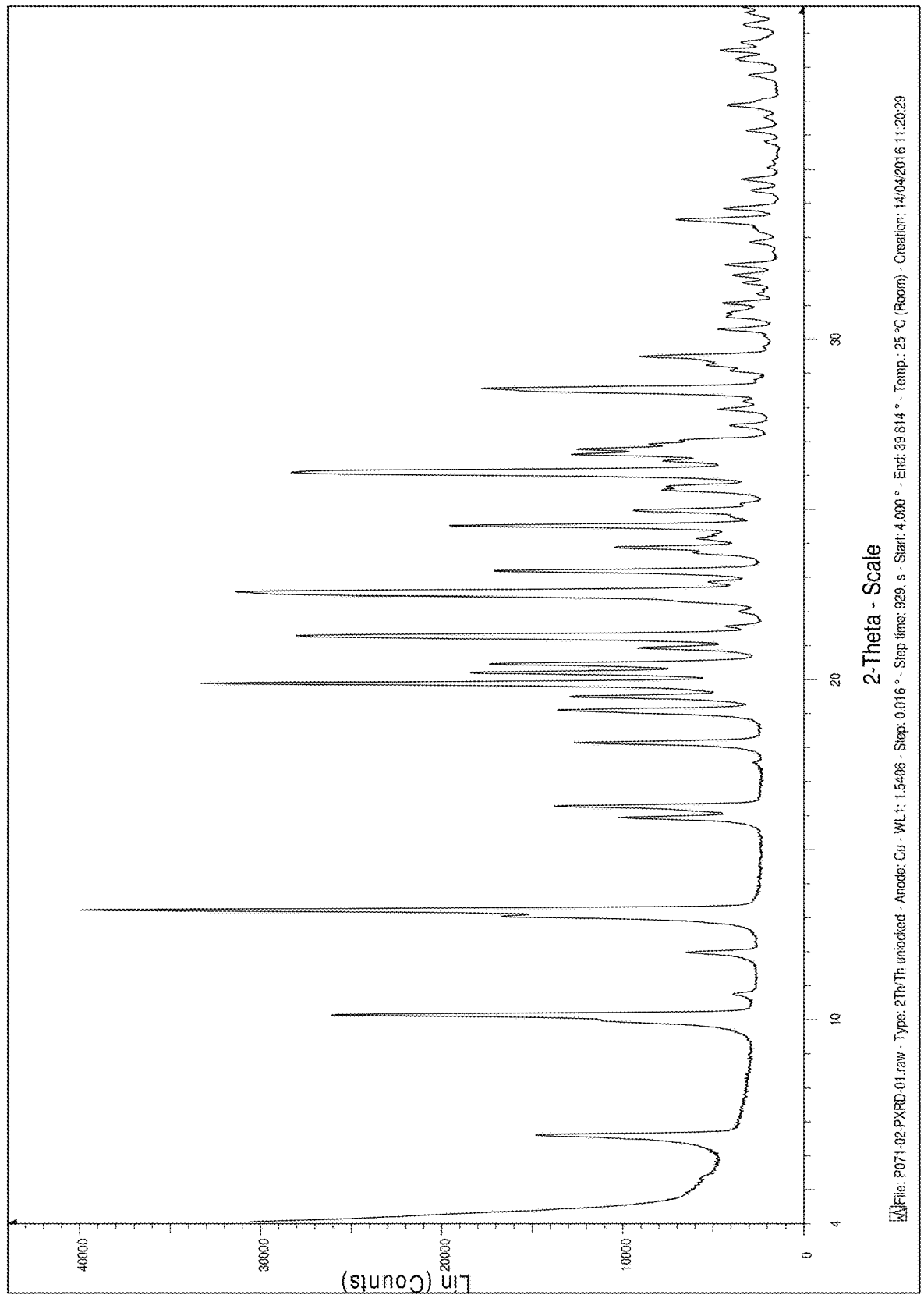
FIG. 9: XRPD of a maleate salt of the free base of pritelivir in accordance with the invention, which shows a crystalline form.

The following examples are included to demonstrate preferred embodiments of the invention. It should be appreciated by those of skill in the art that the techniques disclosed in the examples, which follow, represent techniques discovered by the inventor to function well in the practice of the invention, and thus can be considered to constitute preferred modes for its practice.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention.

EXAMPLES

General Analytical Methods Applied:
Melting Point by DSC
    Principle: Differential scanning calorimetry with power compensation.
    Equipment: DSC-systems (DSC 822e—Mettler Toledo)/analytical micro balance.
    Procedure: An accurately weighed amount of sample (typically 1-5 mg), is placed in a clean
    and dry aluminium crucible and closed with an aluminium cap with a hole. A second crucible is the reference crucible.
    Conditions: starting temperature: 20° C.
    heating rate: 10° C./min.
    final temperature: 300° C.
    atmosphere: $N_2$ (flow 20 mL/min.)
TGA Volatile Components
    Principle: Thermogravimetry.
    Equipment: TGA 851e apparatus comprising oven, oven temperature sensor and sample temperature sensor/aluminium oxide pan/analytical micro balance.
    Procedure: An empty aluminium oxide pan is used to collect the background curve. Afterwards an accurately weighed amount of sample (typically 10 mg) is placed in a clean and dry pan.
    The measurement is done as described in the analytical instruction.
    Conditions: starting temperature: 25° C.
    heating rate: 5° C./min.
    final temperature: 300° C.
    atmosphere: $N_2$ (flow 50 mL/min.)
$^1$H NMR
    Equipment: Bruker AVANCE 400 MHz
    Solvent: DMSO-D6 or CDCl3
    Internal Standard: Tetramethylsilane (TMS) or solvent peak
    Decoupling: Inverse gate decoupling
    Assays: Assays are determined using a macro for the ACD/Spec Manager 9 by comparison of integration areas of the compound with those of an internal standard (typically hydrochinondimethylether) are compared.
Light Microscopy with Hot Stage
    Equipment: Olympus BX41 with Di-Li 5MP camera and grab & measure software; Hotstage Mettler Toledo FP90 with FP 82 heating table.
    Method: Samples are prepared with brushes onto object holders. Observation is done using unpolarised light or polarised light using two polarisation filters at 40, 100, 200 or 400× magnification. Pictures are taken by software and exported as JPEG, scale is only approximate and not validated.

X-Ray Powder Diffraction
Equipment: MiniFlex by Rigaku Corporation using silicon low background sample holders (diameter 24 mm, pit 0.2 mm).
Tube: Cu, λ=1.54056 Å, 15 kV
Method:
Angle: 2θ=2 Å to 2θ=40 Å
Sampling width 0.02 [2θ]
Measurement time: 75 minutes.
Preparation: Samples were ground with mortar and pestle when a sufficient amount was isolated; this leads to more consistent results, less preferred orientation and better handling of material with huge particle size. Solid positioned on sample holder prepared with grease and flattened with a disc of glass.

HPLC
For purity estimation and determination of the solubility in solution a generic in-house method is used.
Column: Phenomenex Luna 3 µm C18 (50×4.6 mm)
Detection: DAD detector, recording at 254 nm
Diluent: 0.5 mg/mL in ACN/$H_2O$ 1:1+1% TFA
Eluents:

A="$H_2O$+0.05% $CF_3COOH$"

B="$CH_3CN$+0.05% CF3COOH"

Method:
Injection: 5 µL
Flow: 1.0 mL/min
Min Eluents

|       |          |
|-------|----------|
| 0.00% | A = 90.0 |
| %     | B = 10.0 |
| 0.10% | A = 90.0 |
| %     | B = 10.0 |
| 10.1% | A = 10.0 |
| %     | B = 90.0 |
| 12.1% | A = 10.0 |
| %     | B = 90.0 |
| 13.1% | A = 90.0 |
| %     | B = 10.0 |
| 15.1% | A = 90.0 |
| %     | B = 10.0 |

Example I—Identification of the Maleate Salt of the Free Base of N-[5-(aminosulfonyl)-4-methyl-1,3-thiazol-2-yl]-N-methyl-2-[4-(2-pyridinyl)-phenyl]acetamide Structure Confirmation by Single Crystal XRD (SCXRD)

Concentrated solutions of the maleate salt of the invention were subjected to various crystallization experiments, which include various techniques such as crystallization by cooling, by evaporation, by vapor diffusion or from the melt.

I.1 Powder X-Ray Diffraction Patterns of the Maleate Salt of the Free Base of Pritelivir Equipment and Methodology Used Sample preparation: In order to acquire a powder diffraction pattern of the obtained solid of the maleate salt, approximately 20 mg of the samples were prepared in standard sample holders using two foils of polyacetate.

Data collection: Powder diffraction patterns were acquired on a Bruker D8 Advance Series 2Theta/Theta powder diffraction system using CuKα1-radiation (1.54060 Å) in transmission geometry. The system is equipped with a VANTEC-1 single photon counting PSD, a Germanium monochromator, a ninety positions auto-changer sample stage, fixed divergence slits and radial soller.

Figure 11:
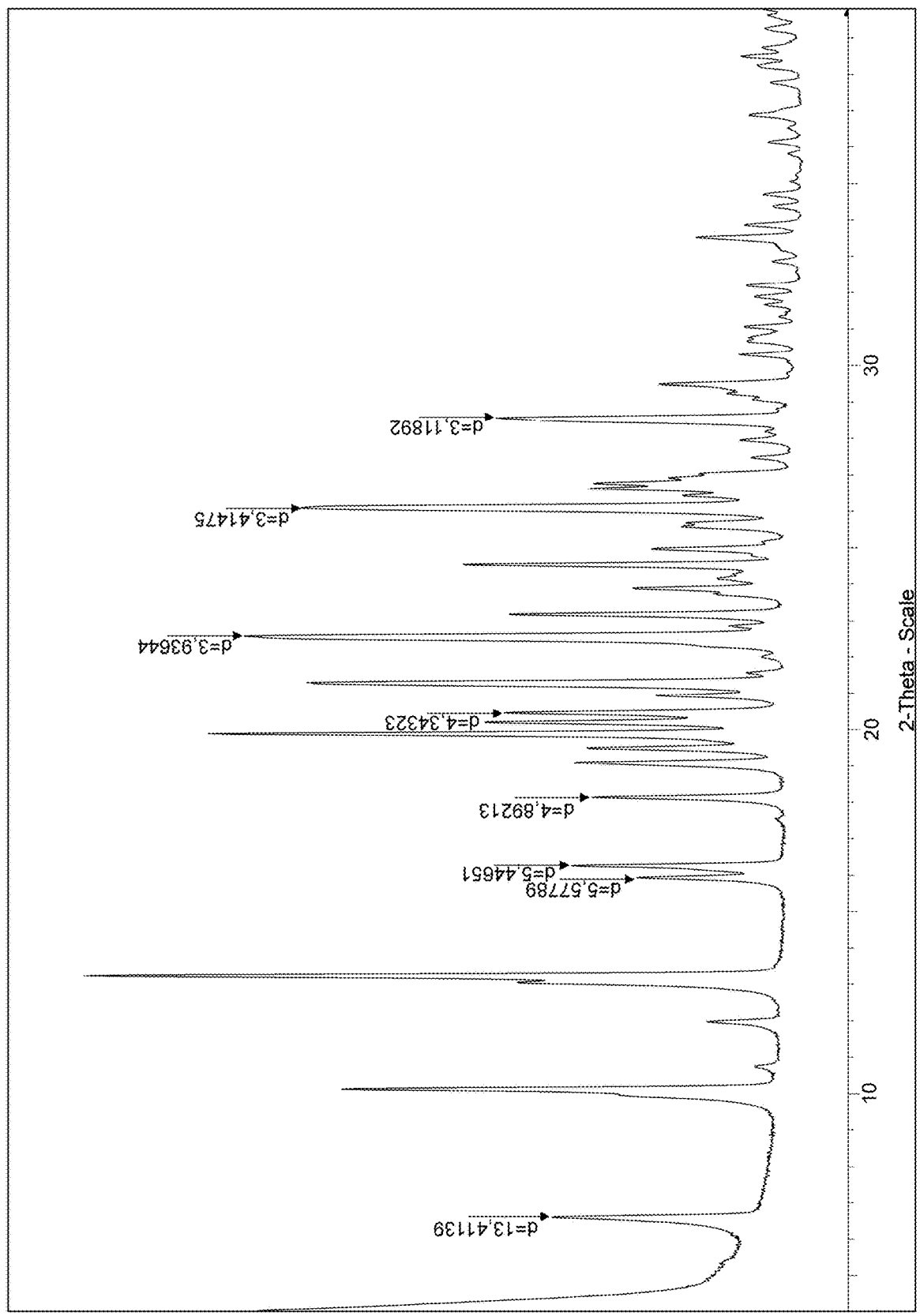
FIG. 11: Characteristic peaks in the Powder X-ray Diffraction Pattern of the maleate salt of the free base of pritelivir (code: P071-02-PXRD-01). Said characteristic peaks of each phase have been marked with an arrow.

Programs used: Data collection with DIFFRAC plus XRD Commander V.2.4.1 and evaluation with EVA V.12.0 and Microsoft Excel™. The samples were measured in 20-minute scans in a range from 4° to 40° in 2θ (step size: 0.016°). See FIGS. 7-11. By the characteristic peaks of e.g. the FIGS. 10 to 11, for the person skilled in the art it could be demonstrated that the maleate salt is a pure crystalline solid.

The physical characterization of the maleate salt of the free base of pritelivir as referred to herein was performed using compendial methods as per European Pharmacopoeia (Ph. Eur.) and/or the U.S. Pharmacopeial Convention (USP).

Whereas all the experiments afford solids via crystallization, the majority are powders or very small single crystals at best (organized in clusters), not suitable for the SCXRD analysis. A suitable, small crystal was obtained via cooling crystallization in acetone and was used for the SCXRD determination, whereas bigger crystals could be obtained after various weeks via vapor diffusion (Methyl Ethyl Ketone/Ethyl Acetate, Methyl Ethyl Ketone/Diethyl Ether and Acetone/Diethyl Ether, not used for SCXRD determination).

Data for structure determination were collected at low temperature (100 K). The asymmetric unit contains one molecule of the cationic organic compound and one molecule of the maleate anion. The structure is unambiguously a salt with maleic acid.

In the maleate salt molecule of the invention one of the carboxylic groups shows clearly different bond lengths for the oxygen atoms (1.22 and 1.32 Å), indicating the protonation of the oxygen atom with the longer bond. The experimental residual electron density confirmed the presence of the hydrogen atom, since it could be clearly localized at the expected position. On the other hand, the second carboxylic group of the maleate shows identical bond lengths (1.26 and 1.27 Å) for the oxygen atoms, whereas no electron densities could be localized at the expected distances for a hydrogen atom. Both the identical bond length and the missing electron densities confirm the presence of a carboxylate group. In the organic molecule, a hydrogen atom could be clearly identified from the residual electron density located at the expected position close to the nitrogen atom of the pyridine ring, confirming the cationic form of the molecule.

The maleate salt of the invention forms an intra-molecular hydrogen bond between both carboxylic groups, which probably stabilize the structure, and the anionic form. Additionally, the carboxylate makes a hydrogen bond with the hydrogen of the pyridine ring. In the crystal packing it can be observed that the maleate salt of the invention makes several additional weak interactions to the organic molecule, which should additionally stabilize the structure. The structure is of excellent quality (R1: 3.81%). All relevant hydrogen atoms were localized experimentally from the residual electron density.

The simulated PXRD pattern from the single crystal data closely resembles the experimental PXRD pattern of the maleate salt of the invention during Phase 1 (see FIGS. 7-11), confirming that the bulk and the measured single crystal correspond to the same crystalline phase.

A series of crystallization experiments of the maleate salt of the invention were performed in various solvents. A single cooling crystallization experiment and three vapor diffusion experiments afforded suitable crystals for SCXRD.

TABLE 1

List of solvents used in the Single Crystal XRD experiments

| Name | Role | Code | Molecular formula | bp (° C.) | mp (° C.) |
| --- | --- | --- | --- | --- | --- |
| Acetone | Solvent | ACE | $C_3H_6O$ | 56 | −94 |
| Acetonitrile | | ACN | $C_2H_3N$ | 82 | −45 |
| Methyl Ethyl Ketone | | MEC | $C_4H_8O$ | 80 | −86 |
| Cyclohexanone | | CHC | $C_6H_{10}O$ | 156 | −16 |
| Methyl Isobutyl Ketone | | MIC | $C_6H_{12}O$ | 118 | −85 |
| 3-Pentanone | | POA | $C_5H_{10}O$ | 102 | −39 |
| Tetrahydrofuran | | THF | $C_4H_8O$ | 66 | −108 |
| Ethyl Acetate | Antisolvent | AET | $C_4H_8O_2$ | 77 | −84 |
| Methyl Acetate | | MAC | $C_3H_6O_2$ | 57 | −98 |
| Diethyl Ether | | EET | $C_4H_{10}O$ | 35 | −116 |

The crystal structure of the maleate salt of the invention was resolved, confirming that the molecule is a salt. The calculated PXRD pattern from the single crystal measurement corresponds to that of the maleate salt of the invention Phase 1 standard.

I.2 Maleate Salt Advantages Over the Freebase and the Mesylate Salt of N-[5-(aminosulfonyl)-4-methyl-1,3-thiazol-2-yl]-N-methyl-2-[4-(2-pyridinyl)-phenyl]acetamide The different salts in accordance with the invention, namely:

The sulfate, the ethanesulfonate, the maleate, the benzene sulfonate, the hemiethane-1,2-disulfonate, the free base and the mesylate salt of N-[5-(aminosulfonyl)-4-methyl-1,3-thiazol-2-yl]-N-methyl-2-[4-(2-pyridinyl)-phenyl]acetamide have been successfully scaled-up and were subsequently studied in more detail with respect to their solubility and stability properties.

I.3 Solubility Properties of the Maleate Salt of Free Base Pritelivir in Water and Relevant Formulation Vehicles (for Oral Route Administration)

| Tested vehicle | Solubility in mg/mL |
| --- | --- |
| Water | 0.48 |
| 30% Capitsol | 24.5 |
| 30% HPBCD | 24.1 |
| Propylene glycol | 5.23 |
| Ethanol | 0.439 |
| PEG400 | 32.2 |

I.4 Solubility Determination in Different Pharmaceutical Excipients

Study objective was to determine the solubility of the free base of pritelivir, the mesylate thereof, the sulfate salt thereof, the mono ethane sulfonate thereof, the maleate salt thereof, the mono benzene sulfonate thereof and the hemi ethane-1,2-disulfonate salt thereof at ambient temperature in 30% Captisol®, 30% Hydroxypropyl-β-cyclodextrin (HP-beta CD), ethanol, propylene glycol (PG) and polyethylene glycol (PEG 400). Dimethyl sulfoxide (DMSO) served as control solvent.

Materials
Test Items
  Reference Item: The free base of pritelivir
  MW free form: 402.5 g/mol
  Purity: 99%
  Batch no.: BX01AWL micronized
Test Items:
  Mesylate salt of free base of pritelivir
  Sulfonate salt of free base of pritelivir
  Mono ethane sulfonate salt of free base of pritelivir
  Maleate salt of free base of pritelivir
  Mono benzene sulfonate salt of free base of pritelivir
  Hemi ethane-1,2-disulfonate of free base of pritelivir
Methods
Sample Preparation Suspensions were prepared by weighing the test items into glass vials and addition of the appropriate solvent. The suspensions were shortly vortex-mixed and shaken overhead for 22 hours. Aliquots (500 µL) were transferred to filtration devices with polyvinylidene fluoride membranes and the solid matter was separated by centrifugation. The filtrates were diluted (1:100) in acetonitrile/methanol/water/acetic acid (25+25+50+0.5, v+v+v+v).

Control solutions of all salts were prepared in DMSO at a concentration of 20 mg/mL and treated as described above. The solubility was determined by concentration measurement of the diluted filtrate of the oversaturated solutions.

Calibration and QC-Samples

Calibration samples were prepared covering a range of 20.0-1001 µg/L. QCs were prepared at three different concentration levels (50.0, 300, 801 µg/mL) for intra batch control.

Chromatography and Detection

Chromatographic separation was performed on a Phenomenex Luna C18(2), 5 µm column (150×2 mm) by gradient elution using 1% acetic acid and acetonitrile/methanol (1+1, v+v) containing 1% acetic acid. For detection, a diode-array detector was used. Absorption was recorded at a wavelength of 300 nm. A detailed method description was filed in the raw data folder.

Data Evaluation

All calculations were carried out with Microsoft Excel 2010. Mean data are given as arithmetic means.

Results:

The free base of pritelivir, the mesylate salt thereof, the sulfonate salt thereof, the mono ethane sulfonate salt thereof, the maleate salt thereof, the mono benzene sulfonate salt thereof, and the hemi ethane-1,2-disulfonate thereof were solved at ambient temperature in Captisol®, HP-β-cyclodextrin (HP-beta CD), ethanol, propylene glycol (PG) and polyethylene glycol (PEG 400). Dimethyl sulfoxide (DMSO) served as control solvent.

Highest solubility was found for all tested salts in 30% Captisol® and 30% β-cyclodextrin solution. In Captisol®, the maximal soluble concentrations under the applied test conditions ranged from 18.5 to 37.6 mg/mL. Similar concentrations were found in D-cyclodextrin in a range of 21.0 to 37.7 mg/mL. The free base of pritelivir showed significantly lower solubility with values of 1.79 and 1.91 mg/mL in Captisol® and β-cyclodextrin, respectively.

The lowest concentrations were observed in ethanol, similar for the free base and all salts, ranging from 0.197 to 0.485 mg/mL. Higher variability with respect to solubility was determined in PG and PEG. The sulfate salt showed the highest concentration in PG at 12.5 mg/mL, followed by the mesylate salt at 11.6 mg/mL, the mono ethane sulfonate salt and the maleate salt between 5 and 6 mg/mL. Lowest solubility was determined for the hemi ethane-1,2-disulfonate salt at 0.769 mg/mL. In PEG, the free base of pritelivir showed highest concentrations at 89.6 mg/mL. The solubility of the maleate salt in PEG was found to be 32.2 mg/mL. All other salts showed values ≤15.2 mg/mL. The recovery from DMSO solution ranged between 93.0 to 109% and confirmed the appropriateness of the assay.

Highest solubility was found for all tested salts in 30% Captisol® and 30% D-cyclodextrin solution. In Captisol®, the maximal soluble concentrations under the applied test conditions ranged from 18.5 to 37.6 mg/mL. Similar concentrations were found in D-cyclodextrin in a range of 21.0 to 37.7 mg/mL. The free base of pritelivir showed significantly lower solubility with values of 179 and 1.91 mg/mL in Captisol® and β-cyclodextrin, respectively.

The lowest concentrations were observed in ethanol, similar for the free base and all salts, ranging from 0.197 to 0.485 mg/mL. Higher variability with respect to solubility was determined in PG and PEG. The sulfate salt showed the highest concentration in PG at 12.5 mg/mL, followed by the mesylate salt at 11.6 mg/mL, the mono ethane sulfonate salt and the maleate salt between 5 and 6 mg/mL. Lowest solubility was determined for the hemi ethane-1,2-disulfonate salt at 0.769 mg/mL. In PEG, the free base showed highest concentrations at 89.6 mg/mL. The solubility of the maleate salt in PEG was found to be 32.2 mg/mL. All other salts showed values ≤15.2 mg/mL.

See FIGS. 48 to 49 for details.

I.5 Solubility in Simulated Gastric and Intestinal Fluids (n=3, Unless Mentioned Differently):

The objective of this study was to determine the relative solubility of the mono ethane sulfonate salt, the maleate salt, the mono benzene sulfonate salt and the hemi ethane-1,2-disulfonate salt in fasted state simulated gastric fluid (FaSSGF), fed state simulated intestinal fluid (FeSSIF) and fasted state simulated intestinal fluid (FaSSIF).

The relative solubility of the free base of pritelivir and the mesylate salt thereof was additionally determined and used as reference.

Materials
Test Items
  Test item: The mono ethane sulfonate salt
  MW mono ethane sulfonate salt: 530.6 g/mol
  MW free form: 402.5 g/mol
  Purity: 99%
  Batch no.: Carbogen-NE-023931-Z-0-2-VV4
  Test item: The maleate salt
  MW maleate salt: 939.1 g/mol
  MW free form: 402.5 g/mol
  Purity: 99%
  Batch no.: Carbogen-NE-023931-Z-0-2-VV3
  Test item: The mono benzene sulfonate salt
  MW mono benzene sulfonate salt: 578.7 g/mol
  MW free form: 402.5 g/mol
  Purity: 99%
  Batch no.: Carbogen-NE-023931-Z-0-2-VV2
  Test item: The hemi ethane-1,2-disulfonate salt
  MW hemi ethane-1,2-disulfonate salt: 1013.2 g/mol
  MW free form: 402.5 g/mol
  Purity: 99%
  Batch no.: Carbogen-NE-023931-Z-0-2-VV1
  Reference item: The pritelivir free base
  MW pritelivir free base form: 402.5 g/mol
  Purity: n.d.
  Batch no.: BHC-BXO1AWL micronized
  Reference item: The mesylate salt
  MW mesylate salt: 516.2 g/mol
  MW free form: 402.5 g/mol
  Purity: 99.8%
  Batch no.: BHC-BXR3NC1 micronized Matrix
Fasted State Simulated Gastric Fluid (FaSSGF)
  SIF Powder Original was added to sodium chloride solution (34.2 mM, pH 1.6) giving a final concentration of 0.06 g/L.

Fasted State Simulated Intestinal Fluid (FaSSIF)
  A buffer was prepared consisting of 10.5 mM sodium hydroxide (MW 40), 28.7 mM sodium dihydrogen phosphate (MW 119.98) and 106 mM sodium chloride (MW 58.44). The pH was adjusted to 6.5 by addition of 1 N hydrochloric acid. SIF Powder Original was added giving a final concentration of 2.24 g/L.

Fed State Simulated Intestinal Fluid (FeSSIF)
  A buffer was prepared consisting of 101 mM sodium hydroxide (MW 40), 144 mM glacial acetic acid (MW 60.05) and 203 mM sodium chloride (MW 58.44). The pH was adjusted to 5 by addition of 1 N hydrochloric acid. SIF Powder Original was added giving a final concentration of 11.2 g/L.

Methods
  All samples were prepared as triplicates with 3 individual initial weights.

Sample Preparation
  Suspensions of the mono ethane sulfonate salt, the maleate salt, the mono benzene sulfonate salt, the hemi ethane-1,2-disulfonate, the mesylate salt or the pritelivir free base were prepared as triplicates by weighing approximately 12 mg test item and addition of 600 µL FaSSGF, FaSSIF or FeSSIF (final concentration 20 mg/mL). The suspensions were incubated at 37° C. Aliquots (100 µL) were transferred into centrifugation devices (polyvinylidene difluoride membrane, 0.2 µm) for removal of solid matter (10 minutes at approximately 15000×g and 37° C.) after 0, 0.5, 1 and 2 hours. FaSSGF filtrates were diluted in acetonitrile to a final dilution of 1:1000. FaSSIF filtrates were diluted in acetonitrile to a final dilution of 1:50 and FeSSIF filtrates to a final dilution of 1:100.

Calibration and QC-Samples
  Calibration- and quality control solutions of the mesylate salt of the free base of pritelivir were prepared in acetonitrile/DMSO 4+1 (v+v). 10 µL calibration or quality control solution were added to methanol/water (1+1, v+v) containing internal standard (i.e. a stable isotope of pritelivir free base in methanol/water (1+1, v+v)+1% acetic acid, 1000 µg/L). Calibration samples were prepared in a range from 10 to 1000 µg/L. Quality control samples were prepared at three different levels (25, 300 and 800 µg/L) as intra batch controls.

Chromatography and Detection
  Chromatographic separation was performed on a Phenomenex Luna PFP(2), 3 µm column (100×2 mm) by gradient elution using 1% acetic acid and acetonitrile/methanol (1/1, v/v) containing 1% acetic acid as mobile phases. For detection, a triple stage mass spectrometer (3200 QTrap) was used operating in positive multiple reaction monitoring mode (MRM transition 403.6→196.3).

The samples were analyzed for their content of the free base of pritelivir. Stability of the free base in the medium was not taken into account as the pH of the simulated fluids was not changed significantly by addition of the low amount of sample and therefore no differences in hydrolysis rate of the base was expected. As hydrolysis products were not determined only relative solubility was used for further evaluations of the results.

Results and Discussion

The relative solubility of the mono ethane sulfonate salt, the maleate salt, the mono benzene sulfonate salt, the hemi ethane-1,2-disulfonate, the free base of pritelivir and the mesylate salt thereof was determined in FaSSGF, FaSSIF and FeSSIF during incubation at 37° C. for 2 hours. The mono ethane sulfonate salt showed the highest relative solubility of all test items in the investigated media FaSSGF, FaSSIF and FeSSIF. The solubility of the hemi ethane-1,2-disulfonate in FaSSGF was found to be higher than the solubility of the maleate salt and the mono benzene sulfonate. In FaSSIF and FeSSIF, the maleate salt, the mono benzene sulfonate and the hemi ethane-1,2-disulfonate showed essentially similar concentrations. The unusual concentration decrease over time in FaSSGF and FaSSIF might be partly explained by hydrolysis of the free base which has been observed in several experimental settings. As hydrolysis products were not determined, only relative solubility should be used for further evaluations of the results. The solubility of the reference items free base pritelivir and the mesylate salt thereof was found to be as expected and in good agreement to earlier investigations. The summarized results are depicted in FIG. 47.

According to the data shown in FIG. 47, the tested salts demonstrate significant advantages over the free base of N-[5-(aminosulfonyl)-4-methyl-1,3-thiazol-2-yl]-N-methyl-2-[4-(2-pyridinyl)-phenyl]acetamide under FeSSIF conditions, where their solubility properties are significantly higher than the solubility of said free base.

In contrast, under FaSSIF conditions, the tested salts of N-[5-(aminosulfonyl)-4-methyl-1,3-thiazol-2-yl]-N-methyl-2-[4-(2-pyridinyl)-phenyl]acetamide only demonstrated advantages over the free base in terms of enhanced solubility properties only over a short period of time, i.e. over 30 min.

Solubility of, the N-[5-(aminosulfonyl)-4-methyl-1,3-thiazol-2-yl]-N-methyl-2-[4-(2-pyridinyl)-phenyl]acetamide salts vis-á-vis the free base thereof was also determined in water and in the presence of different pharmaceutical excipients.

The free base showed the lowest solubility in water at 0.00130 mg/mL. The sulfate salt, the mono ethane sulfonate, the maleate salt, the mono benzene sulfonate salt and the hemi ethane-1,2-disulfonate salt showed similar solubility by ranging from 0.175 to 0.606 mg/mL. The corresponding pH ranged from 3.03 to 3.69. The highest solubility was determined for the mesylate salt, which was found being dissolved in water up to 1.20 mg/mL with a pH of 2.8. These results indicate that the pH has a great impact on solubility. Counter ions with a higher acidity led to a lower pH and a higher solubility. Hereto, see FIG. 47 for the results.

The free base, the mesylate salt, the sulfate, the ethane sulfonate, the maleate, the benzene sulfonate, and the hemiethane-1,2-disulfonate salts have been also tested on their solubility properties at ambient temperature in Captisol®, Hydroxypropyl-β-cyclodextrin (hereinafter abbreviated HP-beta CD), ethanol, propylene glycol (hereinafter abbreviated PG) and polyethylene glycol 400 (hereinafter abbreviated PEG 400). Dimethyl sulfoxide (hereinafter abbreviated DMSO) served as control solvent.

Surprisingly, it has been found by the inventors that the tested salts exhibit significantly higher (i.e. more than 10 times higher) solubility in aqueous cyclodextrin solutions when comprising 30% Captisol® and 30% Hydroxypropyl-β-cyclodextrin (HP-beta CD).

Highest solubility was found for all tested salts in 30% Captisol® and 30% HP-beta CD solution. In Captisol®, the maximal soluble concentrations under the applied test conditions ranged from 18.5 to 37.6 mg/mL. Similar concentrations were found in HP-beta CD in a range as of 21.0 to 37.7 mg/mL. The free base showed significantly lower solubility with values of 1.79 and 1.91 mg/mL in Captisol® and HP-beta CD, respectively.

The lowest concentrations were observed in ethanol, similar for the free base and all tested salts, ranging from 0.197 to 0.485 mg/mL.

Higher variability in terms of solubility properties has been determined in PG and PEG.

The sulfate salt showed the highest concentration in PG at 12.5 mg/mL, followed by the mesylate salt at 11.6 mg/mL, the mono ethane sulfonate salt and the maleate salt between 5 and 6 mg/mL. Lowest solubility was determined for the hemi ethane-1,2-disulfonate at 0.769 mg/mL. In PEG 400, the free base showed highest concentrations at 89.6 mg/mL. The solubility of the maleate salt in PEG was found to be 32.2 mg/mL. All other salts showed values≤15.2 mg/mL.

The recovery from DMSO solution ranged as of from 93.0 to 109% and confirmed the appropriateness of the test assay.

For the detailed results see FIG. 47.

Example II—Stability Determination

Study objective was to determine the stability of the pritelivir free base and its mesylate salt, sulfate salt, mono ethane sulfonate salt, maleate salt, mono bezene sulfonate salt and hemi ethane-1,2-disulfonate salt at ambient temperature and at 50° C. in 30% Captisol®, 30% Hydroxypropyl-β-cyclodextrin (HP-beta CD), ethanol, propylene glycol (PG) and polyethylene glycol (PEG 400) across a time period of two weeks. Additionally, the solubility of the free base of pritelivir and its aforementioned salts in water was determined and the resulting pH was measured.

Materials

Test Items
  Reference Item: Free base of pritelivir
  MW free form: 402.5 g/mol
  Purity: 99%
  Batch no.: BX01AWL micronized
Test Items:
  Mesylate salt of free base of pritelivir.
  Sulfonate salt of free base of pritelivir
  Mono ethane sulfonate salt of free base of pritelivir
  Maleate salt of free base of pritelivir
  Mono benzene sulfonate salt of free base of pritelivir
  Hemi ethane-1,2-disulfonate of free base of pritelivir Methods Sample Preparation Suspensions were prepared by weighing the test items into glass vials and addition of the appropriate solvent. The suspensions were shortly vortex-mixed and shaken overhead for 22 hours. Aliquots (500 µL) were transferred to filtration devices with polyvinyliden fluoride membranes and the solid matter was separated by centrifugation. The filtrates were diluted (1:50 to 1:500) in acetonitrile/methanol/water/acetic acid (25+25+50+0.5, v+v+v+v). Stability and solubility were determined by concentration measurement of the diluted filtrate of the oversaturated solutions.

Calibration and QC-Samples

Calibration samples were prepared covering a range of 20.0-1001 μg/L. QCs were prepared at three different concentrations (50.0, 300, 801 μg/mL) for intra batch control.

Chromatography and Detection

Chromatographic separation was performed on a Phenomenex Luna C18(2), 5 μm column (150×2 mm) by gradient elution using 1% acetic acid and acetonitrile/methanol (1+1, v+v) containing 1% acetic acid. For detection, a diode-array detector was used. Absorption was recorded at a wavelength of 300 nm.

Data Evaluation

All calculations were carried out with Microsoft Excel 2010. Mean data are given as arithmetic means. Recoveries were calculated in comparison to the measured start concentration (t0).

II.1 Short-Term Stability of the Free Base and the Different Salts of N-[5-(aminosulfonyl)-4-methyl-1,3-thiazol-2-yl]-N-methyl-2-[4-(2-pyridinyl)-phenyl] acetamide in Pharmaceutical Excipients All investigated salts and the free base of N-[5-(aminosulfonyl)-4-methyl-1,3-thiazol-2-yl]-N-methyl-2-[4-(2-pyridinyl)-phenyl]acetamide showed stability for two weeks in 30% Captisol®, 30% HP-beta CD, ethanol, propylene glycol and polyethylene glycol when stored under light protecting conditions for two weeks at ambient temperature. Only the free base showed a slight decrease in ethanol, PEG and propylene glycol after two weeks.

Surprisingly, all tested salts showed sufficient solubility in all pharmaceutical excipients after 2 weeks at ambient temperature; see FIG. 50.

After storage at 50° C., the free base showed stability in the aqueous solvents containing 30% Captisol® and 30% HP-beta CD with recoveries compared to the measured start concentration of 103% and 88.9%, respectively. Slight degradation was observed in polyethylene glycol with a recovery of 78.3%. A more pronounced instability was noticed in ethanol and propylene glycol, where 21.3% and 0% were recovered after two weeks at 50° C. After storage at 50° C., the mesylate salt, the sulfate salt, the mono ethane sulfonate salt, the maleate salt, the mono benzene sulfonate salt and the hemi ethane-1,2-disulfonate salt were found to be stable in 30% Captisol®, 30% HP-beta CD, ethanol and propylene glycol with recoveries compared to the measured start concentration of ≥85% after two weeks.

The ethanesulfonate salt, the benzene sulfonate salt and the hemiethane-1,2-disulfonate salt showed degradation in polyethylene glycol after two weeks storage at 50° C. The recoveries were determined at 80.1%, 74.7% and 75.4% for ethanesulfonate salt, the benzene sulfonate salt and the hemiethane-1,2-disulfonate salt, respectively. The mesylate salt, the sulfate salt and the benzene sulfonate salt showed stability in polyethylene glycol after two weeks storage at 50° C.

Surprisingly, the above mentioned tested salts of N-[5-(aminosulfonyl)-4-methyl-1,3-thiazol-2-yl]-N-methyl-2-[4-(2-pyridinyl)-phenyl]acetamide, including the maleate salt, exhibited an improved stability in pharmaceutical excipients even after two weeks of storage at accelerated conditions of 50° C.; see FIG. 51 for further details.

Example III—Photostability Experiments of the Free Base and the Tested Salts of N-[5-(aminosulfonyl)-4-methyl-1,3-thiazol-2-yl]-N-methyl-2-[4-(2-pyridinyl)-phenyl]acetamide Study objective was to determine the photostability of the pritelivir free base versus the salts thereof in accordance with the invention; i.e a mesylate salt, a sulfate salt, a mono ethane sulfonate salt, a maleate salt, a mono benzene sulfonate salt and a hemi ethane-1,2-disulfonate salt after exposition to 2000 Wh/m$^2$ (approximately 29 hours at wavelengths of >310 nm).

The compounds were exposed as solids and dissolved in 0.1 M hydrochloric acid/acetonitrile (75+25, v+v) at a target concentration of 0.3 mg/mL. Corresponding dark control samples were prepared and placed in UV-light protected vials in the irradiation chamber to keep the ambient conditions equivalent. Additionally, untreated solids were dissolved and analyzed as reference samples.

All samples were prepared and irradiated at A&M Labor für Analytik und Metabolismusforschung Service GmbH (A&M 15-034). After treatment, the samples were stored deep frozen until shipment to AiCuris where the analysis was performed.

III.1—Materials

Reference and Test Items

Reference Item: Free base of pritelivir

MW free form: 402.5 g/mol

Purity: 99%

Batch no.: BX01AWL micronized

Test Items Batch No.

Free base of pritelivir (Batch BXR2KVE)

Mesylate salt of free base of pritelivir (Batch Car-NE-023932-Batch-05-2010)

Sulfonate salt of free base of pritelivir (Batch Carbogen-NE-021681-A-1-3 crude 1 #1)

Mono ethane sulfonate salt of free base of pritelivir (Batch Carbogen-NE-026323-A-1-1 crude 1 #1)

Maleate salt of free base of pritelivir (Batch Carbogen-NE-026322-A-1-1 crude 1 #1)

Mono benzene sulfonate salt of free base of pritelivir (Batch Carbogen-NE-026321-A-1-1 crude 1 #1)

Hemi ethane-1,2-disulfonate of free base of pritelivir (Batch Carbogen-NE-026320-A-1-1 crude 1 #1)

III.2—Methods

All samples were prepared and irradiated at A&M Labor für Analytik und Metabolismusforschung Service GmbH (A&M 15-034). After treatment, the samples were stored deep frozen until shipment to AiCuris where the analysis was performed.

Preparation of Solid Samples

Two samples were prepared from each solid test item. Approximately 20 mg of each test item (corrected for free base) was weighed into quartz glass vials. A second aliquot was weighed into light protected glass vials (dark control). Both samples were placed inside the irradiation chamber.

Preparation of Solutions

Approximately 20 mg of each test item (corrected for free base) was weighed and dissolved in 0.1 M hydrochloric acid/acetonitrile (75+25, v+v) resulting in a uniform concentration of 300 μg/mL of the free base of pritelivir. Two aliquots were prepared (irradiated and dark control sample).

The dark control samples were stored inside the irradiation chamber in closed and light protected glass vials, while the photostressed solutions were stored in quartz flasks, equipped only with a loose quartz glass cover. During irradiation, the samples were partially evaporated due to heat production inside the irradiation chamber. The extent of evaporation was variable from sample to sample (the sulphate salt of pritelivir free base was almost completely evaporated). Therefore, the irradiated solutions were filled up to the initial volume with 0.1 M hydrochloric acid/acetonitrile (75+25, v+v) in order to ensure comparability between the different solutions and to the respective dark control samples.

Irradiation

The samples (solutions and solid state) were irradiated with a xenon lamp at 765 Wh/m$^2$ through a glass filter for 29 hours (total applied dose of UV-light ca. 2000 Wh/m$^2$). The instrument used was a Suntest CPS+ (Atlas). By the use of the glass filter, only wavelengths >310 nm were irradiated, leading to simulation of the ID65 standard (indoor indirect daylight standard). The irradiated light also included the full VIS spectrum. The recorded average chamber heat temperature was 38° C. After irradiation, all samples were stored deep frozen until analysis.

Sample Preparation for Chromatography

The irradiated solids and the dark controls were thawed and 2-3 mg were weighed and dissolved in 0.1 M hydrochloric acid/acetonitrile (75+25, v+v) at a concentration of 3 mg/mL. The solutions were subsequently diluted in 0.1 M hydrochloric acid/acetonitrile (75+25, v+v) to a final concentration of 0.3 mg/mL. The solutions were thawed and transferred to fresh glass vials for analysis.

Chromatography and Detection

The % peak area was determined for the pritelivir free base in all tested samples. Chromatographic separation was performed on a Phenomenex Luna C18(2), 5 µm column (150×2 mm) by gradient elution using 1% acetic acid and acetonitrile/methanol (1+1, v+v) containing 1% acetic acid. For detection, a diode-array detector was used. Absorption was recorded at a wavelength of 280 nm. A detailed method description was filed in the raw data folder.

Data Evaluation

All samples (solids and solutions) were dissolved or diluted in 0.1 M hydrochloric acid/acetonitrile (75+25, v+v) prior analysis to a final concentration of approximately 0.3 mg/mL. The degree of decomposition was determined by chromatographic separation of (UV-active) degradation products and by determination of the respective percentage of the total peak area (% total peak area) per chromatogram. As salts dissociate in solution, the peak area of the pritelivir free base was determined in all samples.

Due to chromatographic issues, the dark control samples of the irradiated solutions of the sulfate salt and the hemi ethane-1,2-disulfonate were re-analyzed in a separate batch including dark controls of the free base of pritelivir and the mesylate salt thereof as reference samples. Hence, % peak area of the free base of pritelivir and the mesylate salt thereof were reported as means of n=2. All calculations were carried out with Microsoft Excel 2010.

III.4 Results and Discussion

The untreated solids of pritelivir free base and its salts were found to be highly stable when stored deep frozen with % total peak area of the free base of pritelivir between 99.7 and 100%. Individual degradation products were found with % total peak area ≤0.5%. The solid free base and the solid salts showed good stability against irradiation with UV-light at a total dose of 2000 Wh/m$^2$. No significant decomposition was observed in the solutions of irradiated solids and the corresponding dark control samples. Single degradation products were found in low amounts with % total peak area ≤0.5%. The determined % total peak area of the free base of pritelivir ranged from 97.4% to 100%.

The dark control samples of the acidic solutions showed good photostability of the free base of pritelivir with % total peak area ranging from 97.4 to 98.3% in the solutions of pritelivir free base, the mesylate salt thereof, the mono ethane sulfonate salt thereof, the maleate salt thereof and the mono benzene sulfonate salt thereof. Slight decomposition was observed for the sulfate salt and the hemi ethane-1,2-disulfonate in which 95.7 and 94.7% of the total peak area were observed to be related to the free base of pritelivir. Single impurities were observed with % peak areas ≤1.58%.

The irradiated solutions showed high degrees of decomposition after 29 hours at a total dose of 2000 Wh/m$^2$. The free base of pritelivir was found with % total peak area between 6.67 and 11.9% in solutions of the pritelivir free base, the mesylate salt thereof, the sulfate salt thereof, the mono ethane sulfonate salt thereof, the mono benzene sulfonate salt thereof and the hemi ethane-1,2-disulfonate salt thereof. The major degradation product (relative retention time 0.85) was observed in solutions of pritelivir free base and all salts (except for the maleate salt) with % total peak area between 27.8 and 36.2%. Three other decomposition products (RRT 0.64, 0.67 and 0.87) were detected reaching more than 10% total peak area in some solutions. The dissolved maleate salt of the pritelivir free base showed significantly lower degradation. After 29 hours of irradiation by UV-light, the free base of pritelivir represented 71.5% of the total peak area. The major degradation product at a RRT of 0.85, which was also seen for the other test items, was observed with 14.7% total peak area. All other degradation products were found to be ≤3.3% of total peak area.

In more detail:

The tested solid free base and the solid salts of N-[5-(aminosulfonyl)-4-methyl-1,3-thiazol-2-yl]-N-methyl-2-[4-(2-pyridinyl)-phenyl]acetamide showed sufficient stability against irradiation with UV-light at a total dose of 2000 Wh/m$^2$. No significant decomposition was observed in the solutions of irradiated solids and the corresponding dark control samples. Individual degradation products were found in low amounts with % total peak area of ≤0.5%. The determined peak areas of the free base of N-[5-(aminosulfonyl)-4-methyl-1,3-thiazol-2-yl]-N-methyl-2-[4-(2-pyridinyl)-phenyl]acetamide ranged from 97.4% to 100% as shown in the FIGS. 45 to 46 and 52 to 53.

The irradiated solutions showed high degrees of decomposition after 29 hours at a total dose of 2000 Wh/m$^2$. The free base was found with % total peak area between 6.67 and 11.9% in the tested solutions containing the free base, the mesylate salt, the sulfate salt, the mono ethane sulfonate salt, the mono benzene sulfonate salt and the hemi ethane-1,2-disulfonate salt of N-[5-(aminosulfonyl)-4-methyl-1,3-thiazol-2-yl]-N-methyl-2-[4-(2-pyridinyl)-phenyl]-acetamide. The major degradation product (showing a relative retention time 0.85 (RRT)) was observed in solutions of the free base and all tested salts (except for the maleate salt with % total peak area between 27.8 and 36.2%). Three other decomposition products (RRT at 0.64, 0.67 and 0.87) were detected reaching more than 10% total peak area in some solutions.

Surprisingly and unexpected, the dissolved maleate salt showed lower degradation. After 29 hours of irradiation by UV-light, the remaining free base content was represented by 71.5% of the total peak area. The major degradation product was to be found at a RRT of 0.85, which was also seen for the other tested salts, observed with 14.7% total peak area. All other degradation products were found to be ≤3.3% of total peak area.

The % total peak area for the free base of N-[5-(aminosulfonyl)-4-methyl-1,3-thiazol-2-yl]-N-methyl-2-[4-(2- pyridinyl)-phenyl]acetamide contents in the tested irradiated solutions and in the respective dark controls is shown in FIGS. 45 to 46 and 52 to 53.

Surprisingly and unexpected, the maleate salt exhibited a significantly higher photostability; i.e. 71.5% total peak area for the free base of N-[5-(aminosulfonyl)-4-methyl-1,3-thiazol-2-yl]-N-methyl-2-[4-(2-pyridinyl)-phenyl]acetamide versus 11.9% total peak area for the free base of N-[5-(aminosulfonyl)-4-methyl-1,3-thiazol-2-yl]-N-methyl-2-[4-(2-pyridinyl)-phenyl]acetamide with the co-tested salts and the free base itself.

Example IV—Further Characterisation of the Maleate Salt of the Free Base of Pritelivir The maleate salt of the free base of pritelivir in accordance with the invention has been further characterised by $^1$H-NMR and $^{13}$C-NMR analyses, FT-IR analyses, UV-Vis analyses, and Mass Spectrometry.

IV.1 Equipment and Methodology Used $^1$H- and $^{13}$C-Nuclear Magnetic Resonance Proton and Carbon nuclear magnetic resonance analyses were recorded in deuterated dimethylsulfoxide (DMSO-d$_6$) in a Bruker-AV 500 Mhz NMR spectrometer. Spectra were acquired solving 10-20 mg of sample in 0.6 mL of deuterated solvent. Number of scans: 128 ($^1$H-NMR), 2048 ($^{13}$C-NMR).

Fourier Transform Infrared Spectroscopy

The FTIR spectra were recorded using an Agilent Cary 630 spectrometer, equipped with a Diamond single reflection ATR system. The background was acquired before each measurement and the spectra were acquired in 128 scans at a resolution of 4 cm$^{-1}$ in the range of 4000-600 cm$^{-1}$.

UV-Visible Spectroscopy

UV-Vis measurements were carried out at room temperature in 1 cm quartz cuvettes in a Shimadzu UV-2401PC spectrophotometer equipped with a photomultiplier tube detector, double beam optics and D2 and W light sources.

For sample preparation, the sample was diluted in Acetonitrile (25 g/mL) and then analyzed by UV-visible spectroscopy in the wavelength range of 200-900 nm.

Mass Spectrometry

Mass Spectra were acquired in a Bruker Daltonics HLPC-MS-TOF MicroTOF II with a mass range of 50-20000 m/z, a resolving power of 16500 FWHM (Full Width at Half Maximum) at m/z 1220 and a mass accuracy of ≤5 ppm. Used ionization mode: ESI Negative.

IV.2 Results:

$^1$H-NMR and $^{13}$C-NMR Analyses

Figure 12:
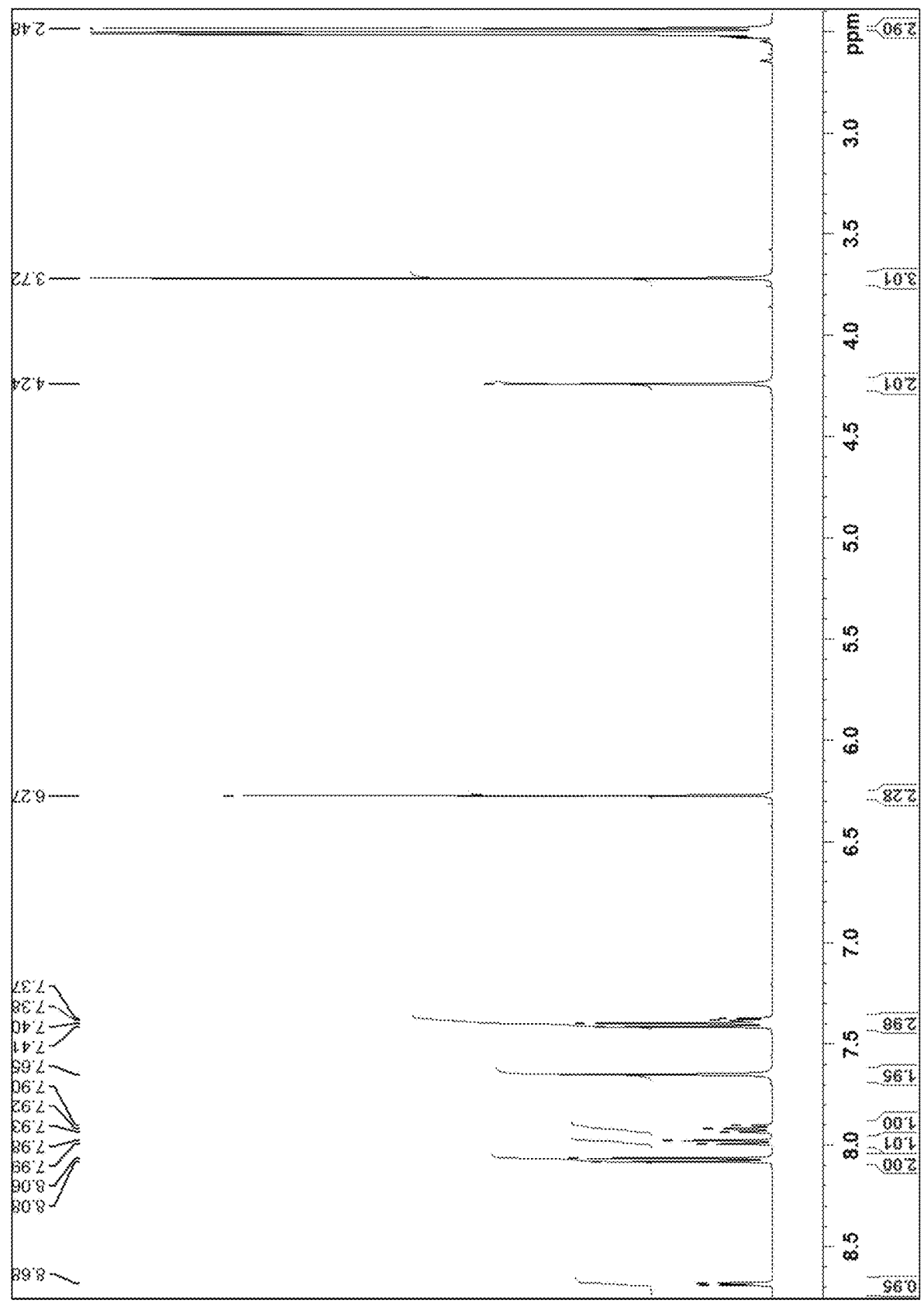
FIG. 12: $^1$H-NMR spectrum of the maleate salt of the free base of pritelivir.
Figure 14:
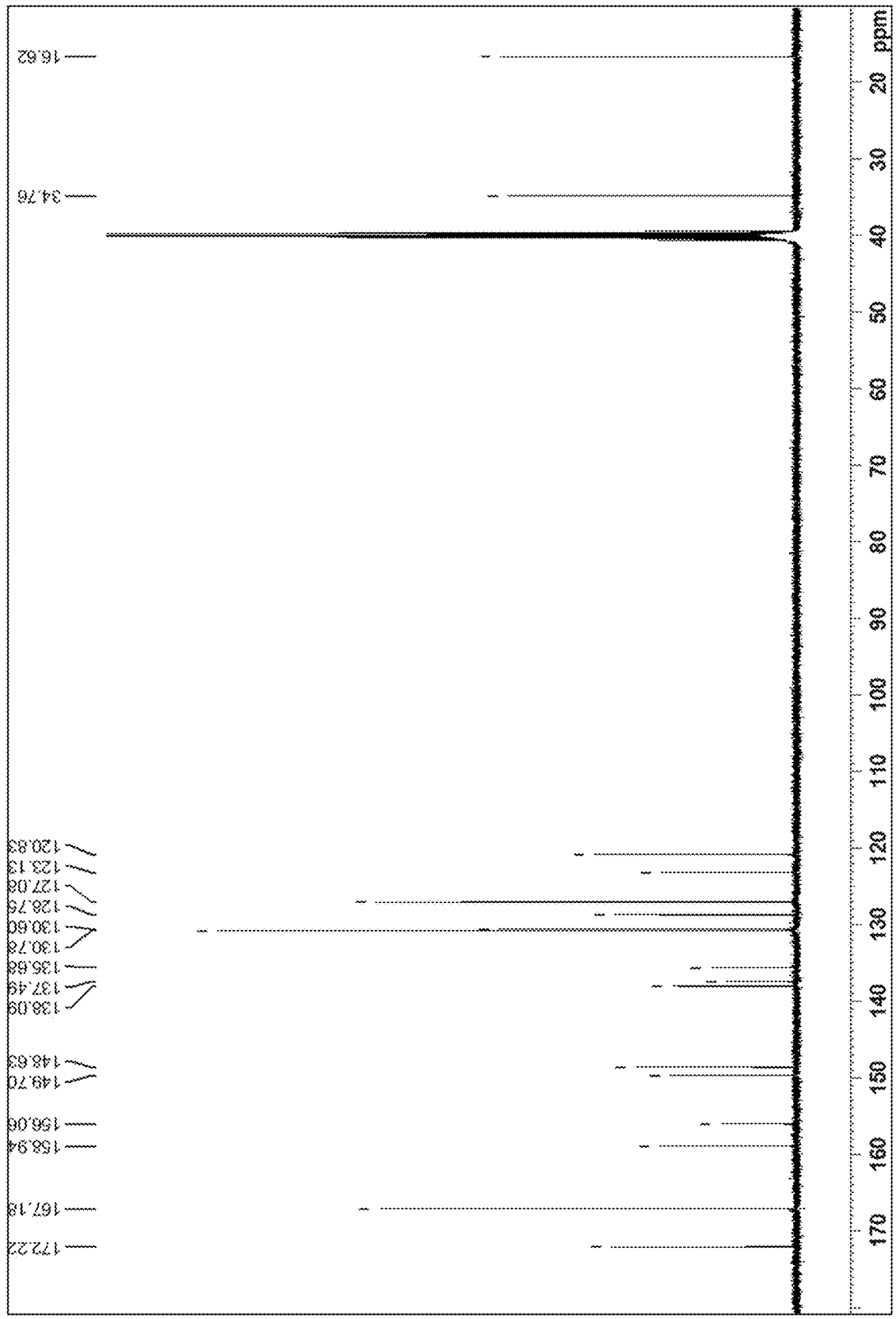
FIG. 14: $^{13}$C-NMR spectrum of the maleate salt of the free base of pritelivir.

Proton and Carbon NMR spectra of a maleate salt of the free base of pritelivir (see FIGS. 12 and 14, and the tables in FIGS. 13 and 15) in deuterated DMSO, show no significant impurities.

FT-IR Analyses

Figure 16:
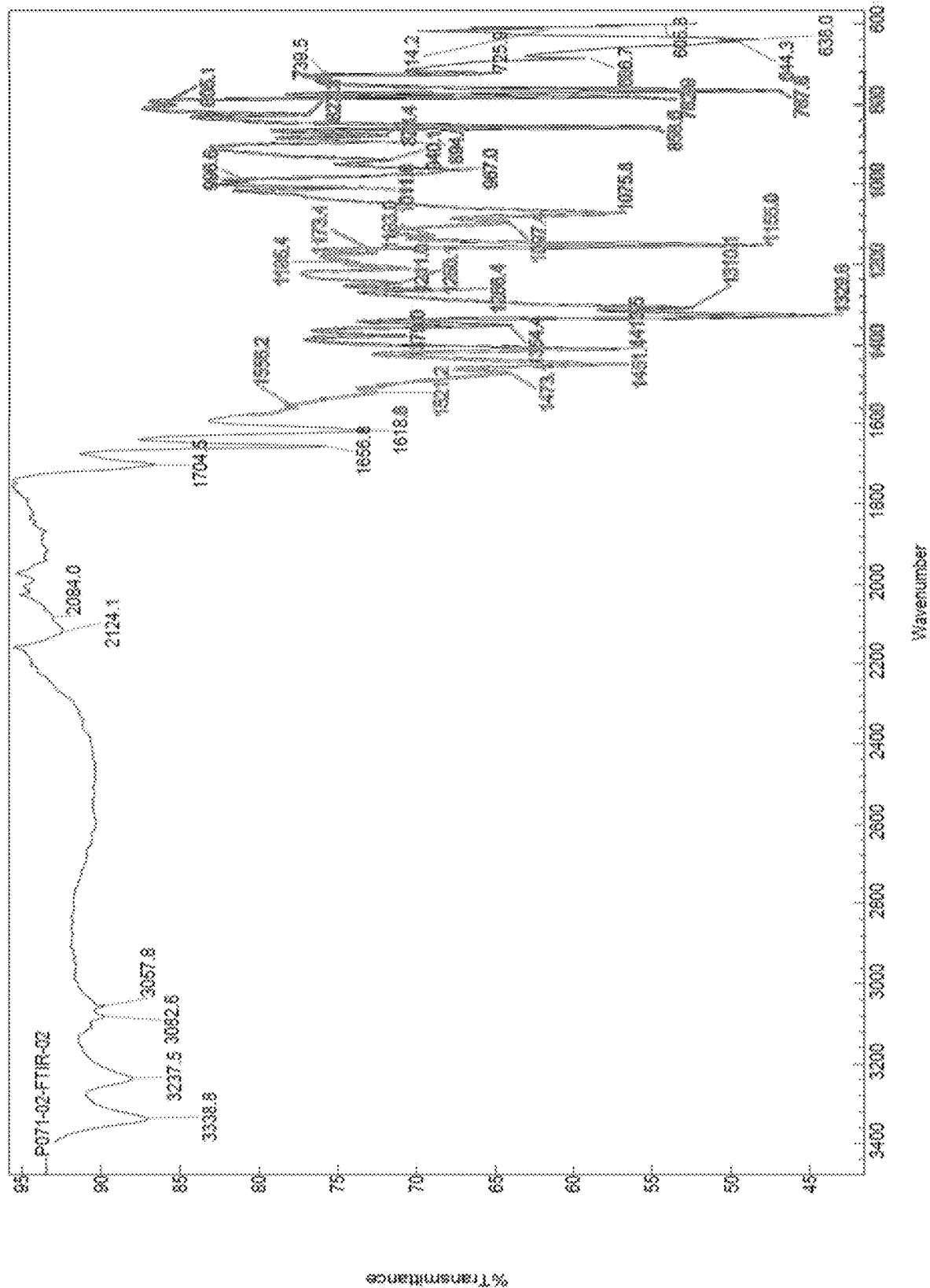
FIG. 16: FT-IR spectrum of the maleate salt of the free base of pritelivir.

FT-IR spectra of a maleate salt of the free base of pritelivir are depicted in the FIG. 16 and a corresponding peak list is available in the table of FIG. 17.

UV-Vis Analyses

Figures 18, 19:
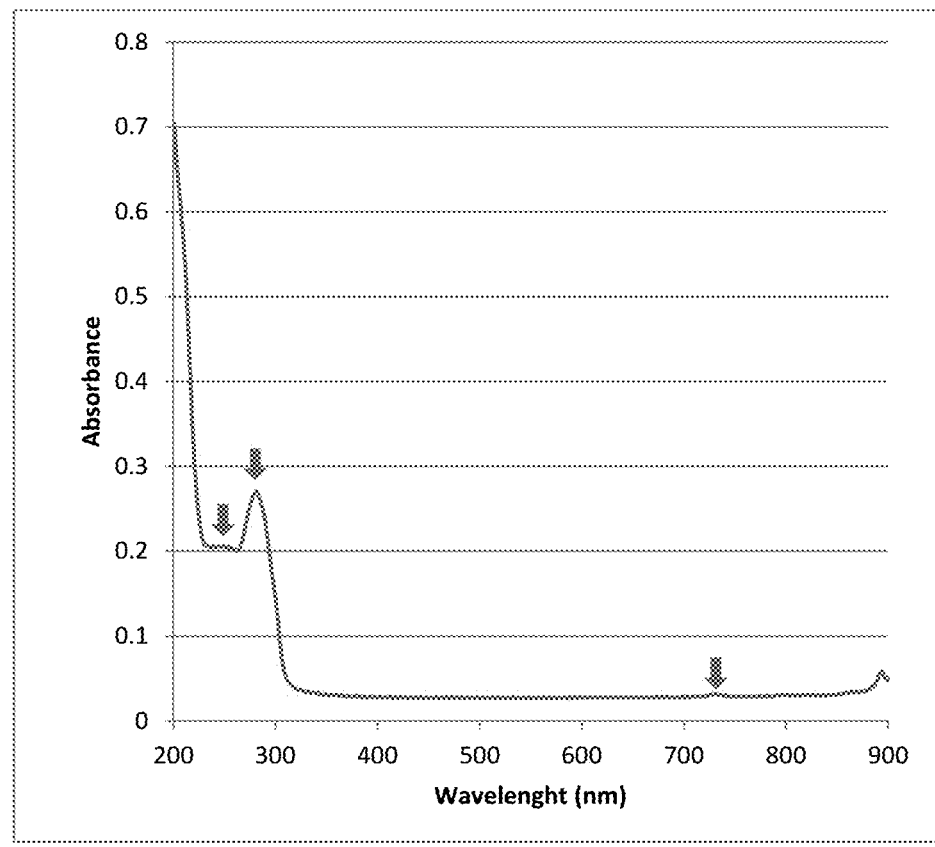
FIG. 18: UV-Vis spectrum of the maleate salt of the free base of pritelivir.
FIG. 19: Peak list for the UV-Vis spectrum of the maleate salt of the free base of pritelivir of FIG. 18.

The UV-Vis spectra (in the 200-900 nm range) of a maleate salt of the free base of pritelivir in acetonitrile (4 g/mL solutions) are depicted in FIGS. 18 to 19.

Mass Spectrometry

Figure 20:
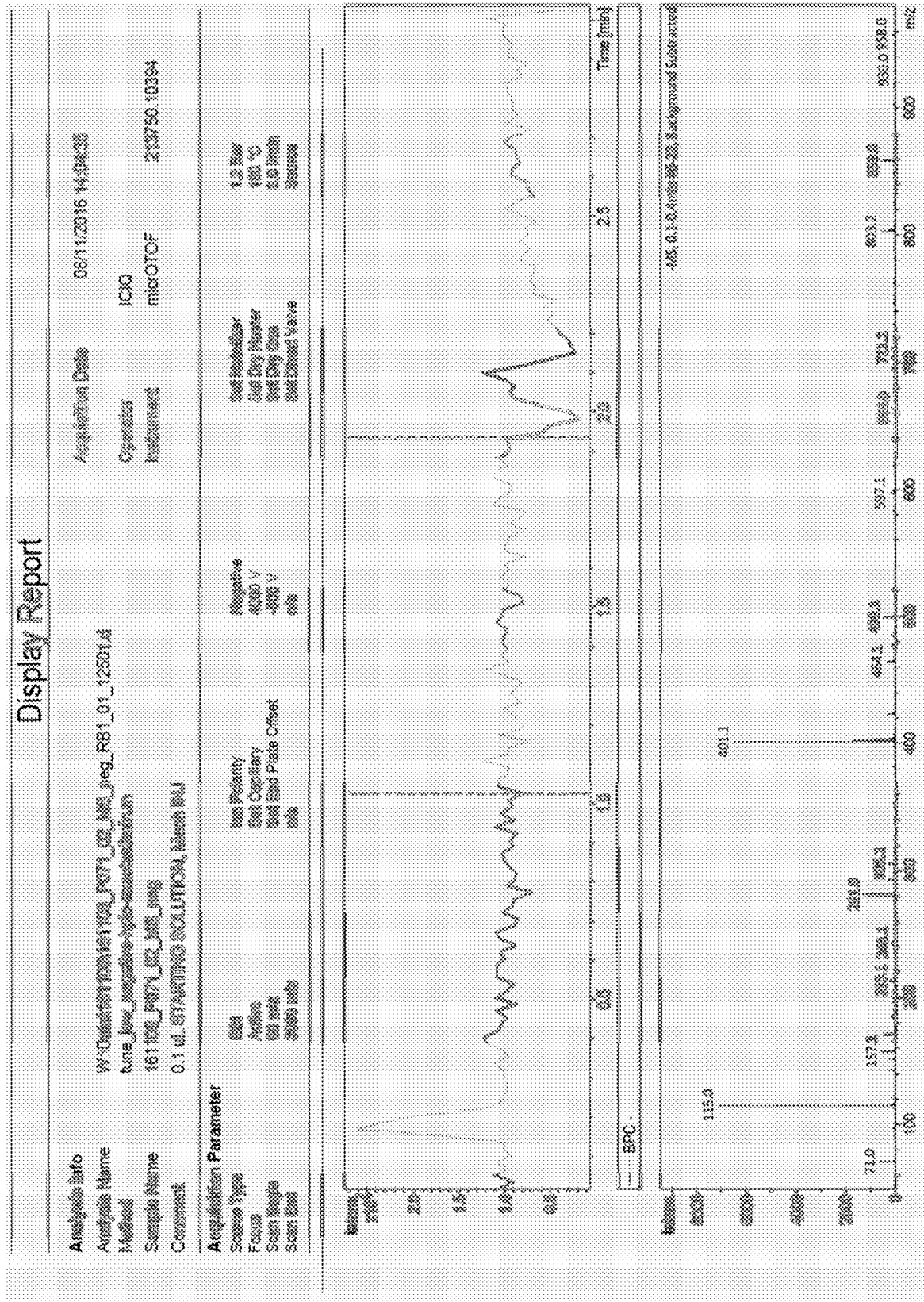
FIG. 20: MS spectrum of the maleate salt of the free base of pritelivir.
Figure 22:
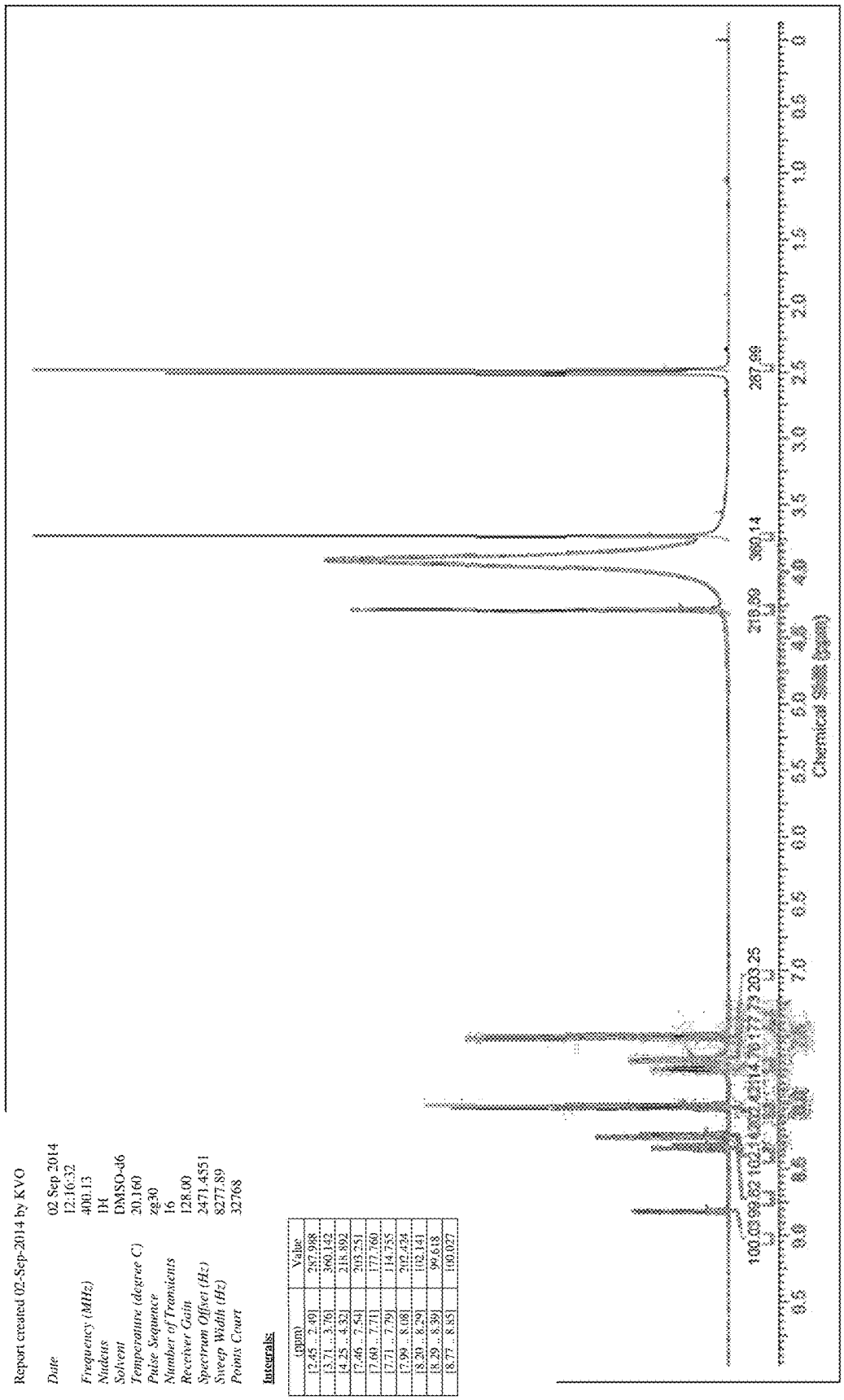
FIG. 22: $^1$H NMR spectrum of a sulfate salt of the free base of pritelivir in accordance with the invention.
Figure 23:
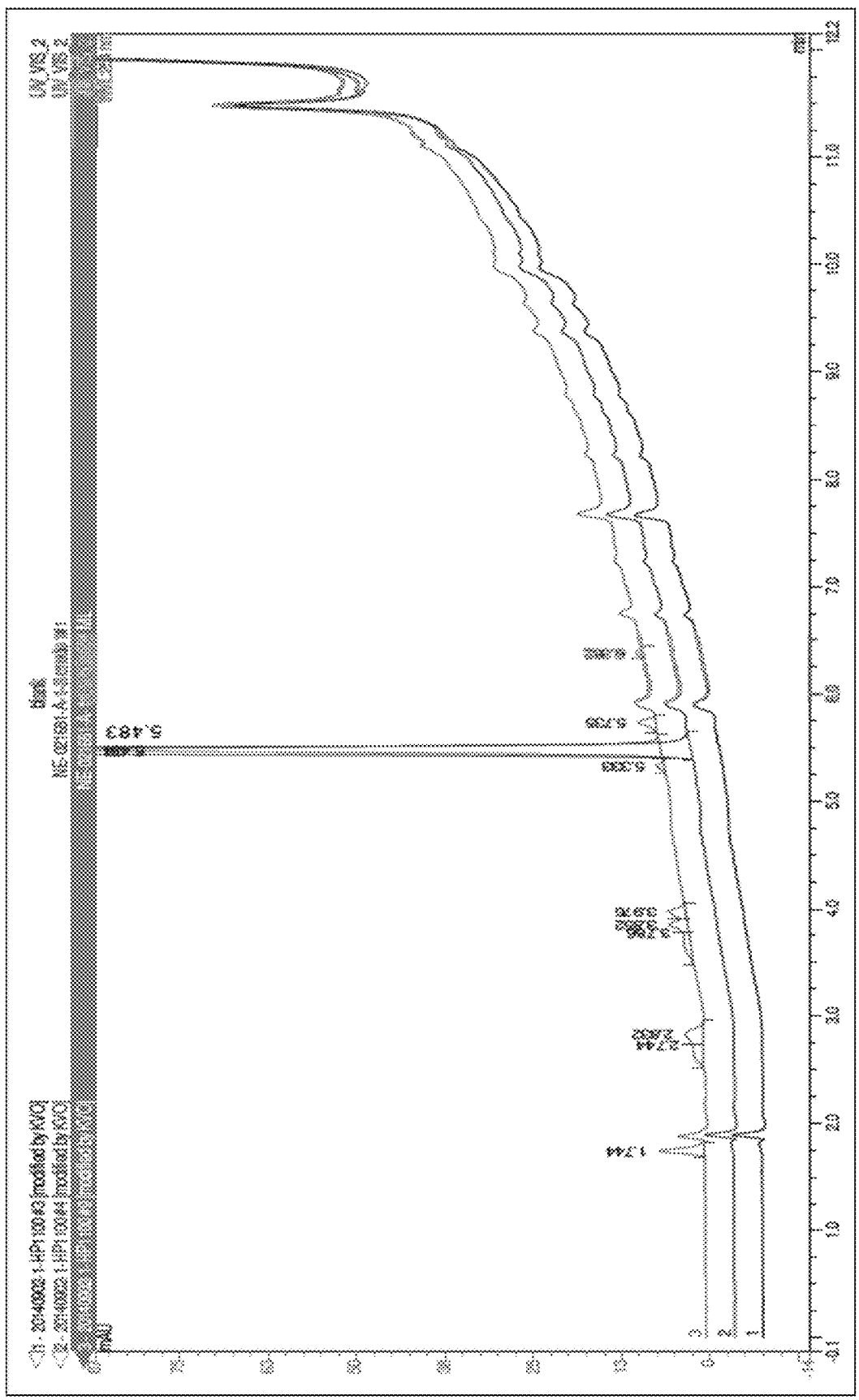
FIG. 23: HPLC overlay of a sulfate salt of the free base of pritelivir in accordance with the invention (middle, 100.0% a/a); with corresponding mother liquor (top, 73.83% a/a) and blank (bottom).
Figure 24:
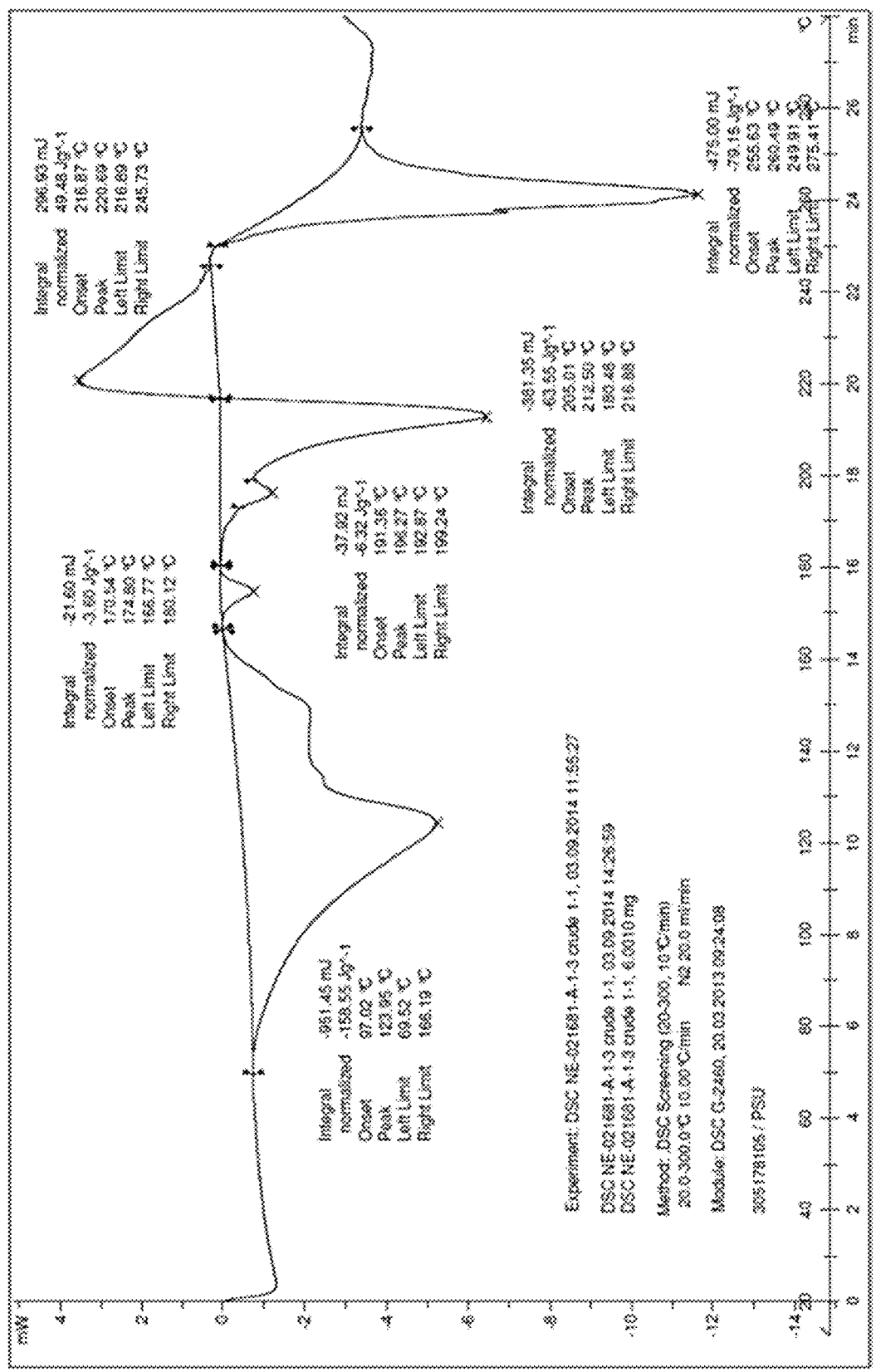
FIG. 24: DSC of a sulfate salt of the free base of pritelivir in accordance with the invention. No clear melting point is visible but a large endothermicity due to water release (97° C. onset).
Figure 25:
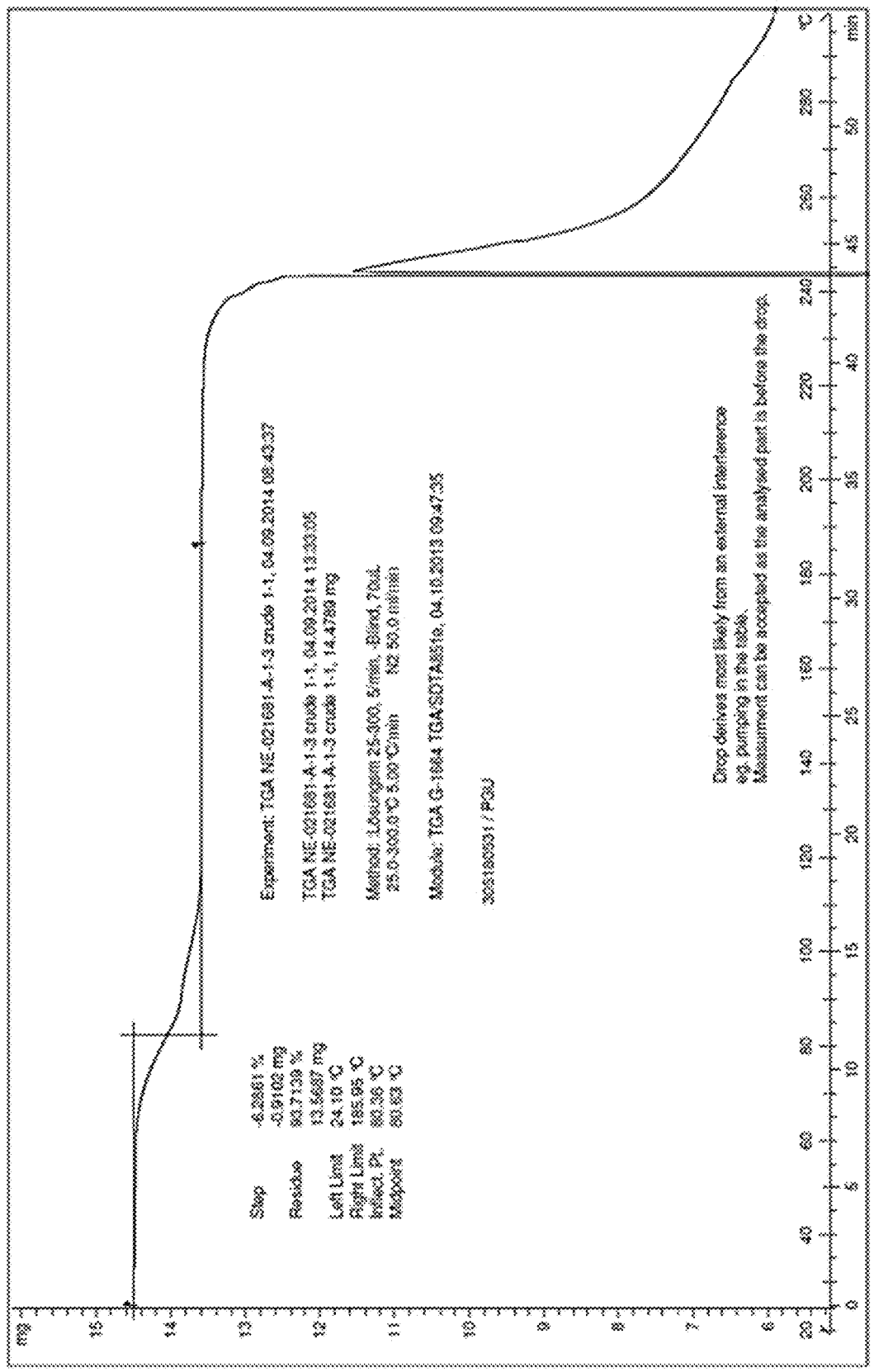
FIG. 25: TGA of a sulfate salt of the free base of pritelivir in accordance with the invention with a weight loss of 6.3% w/w.
Figure 26:
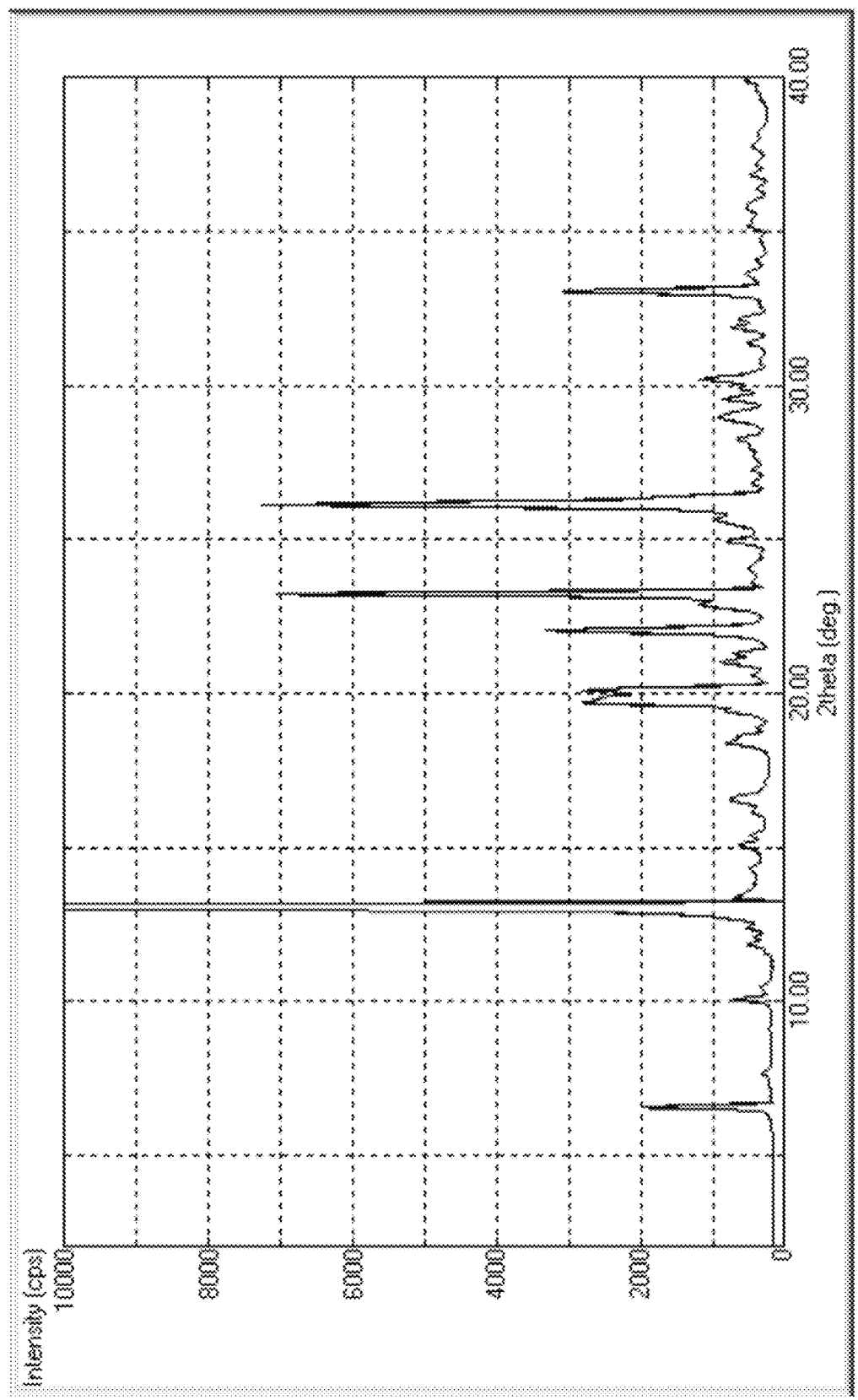
FIG. 26: XRPD of a sulfate salt of the free base of pritelivir in accordance with the invention.
Figure 27:
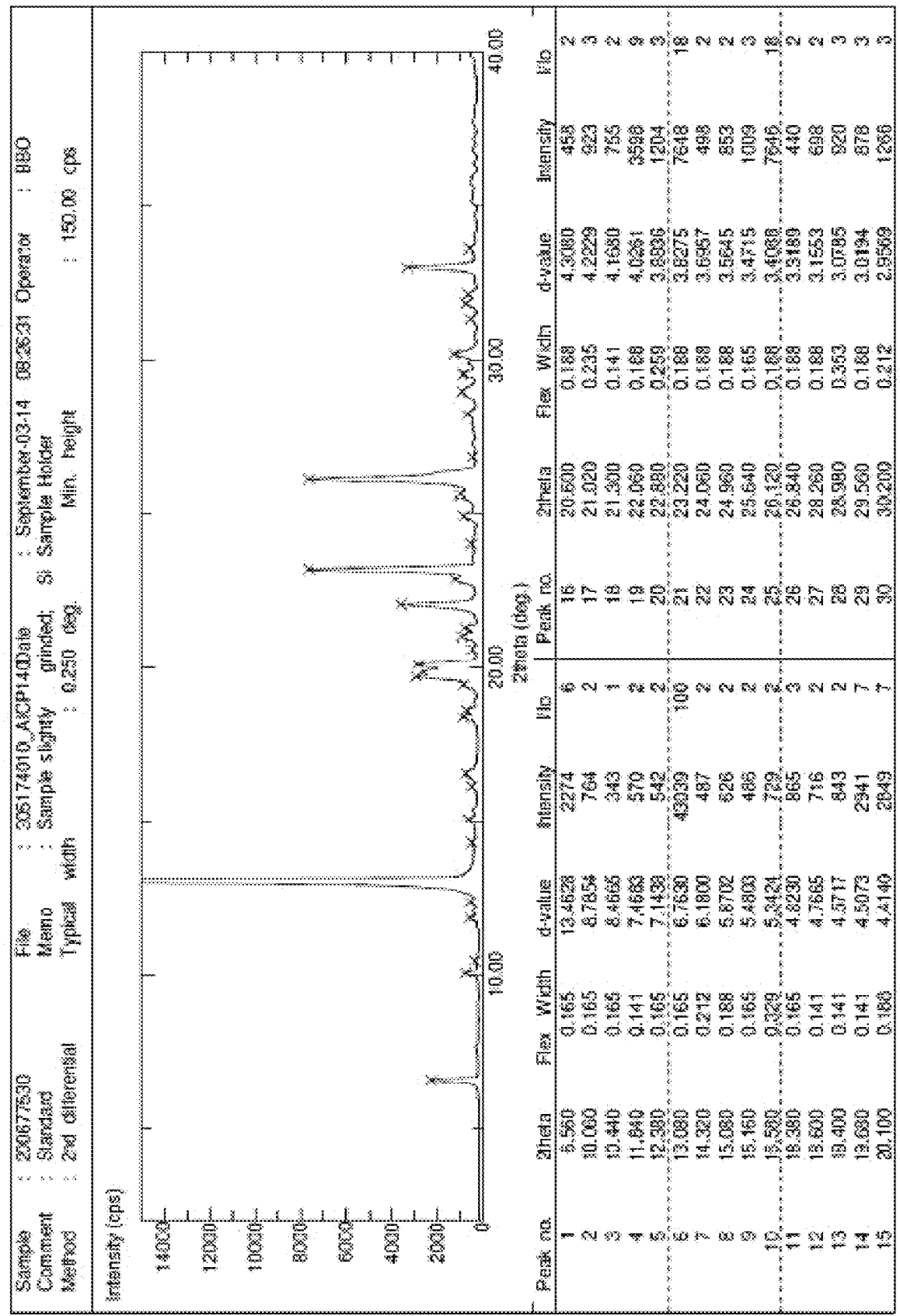
FIG. 27: XRPD data for a sulfate salt of the free base of pritelivir in accordance with the invention.
Figure 28:
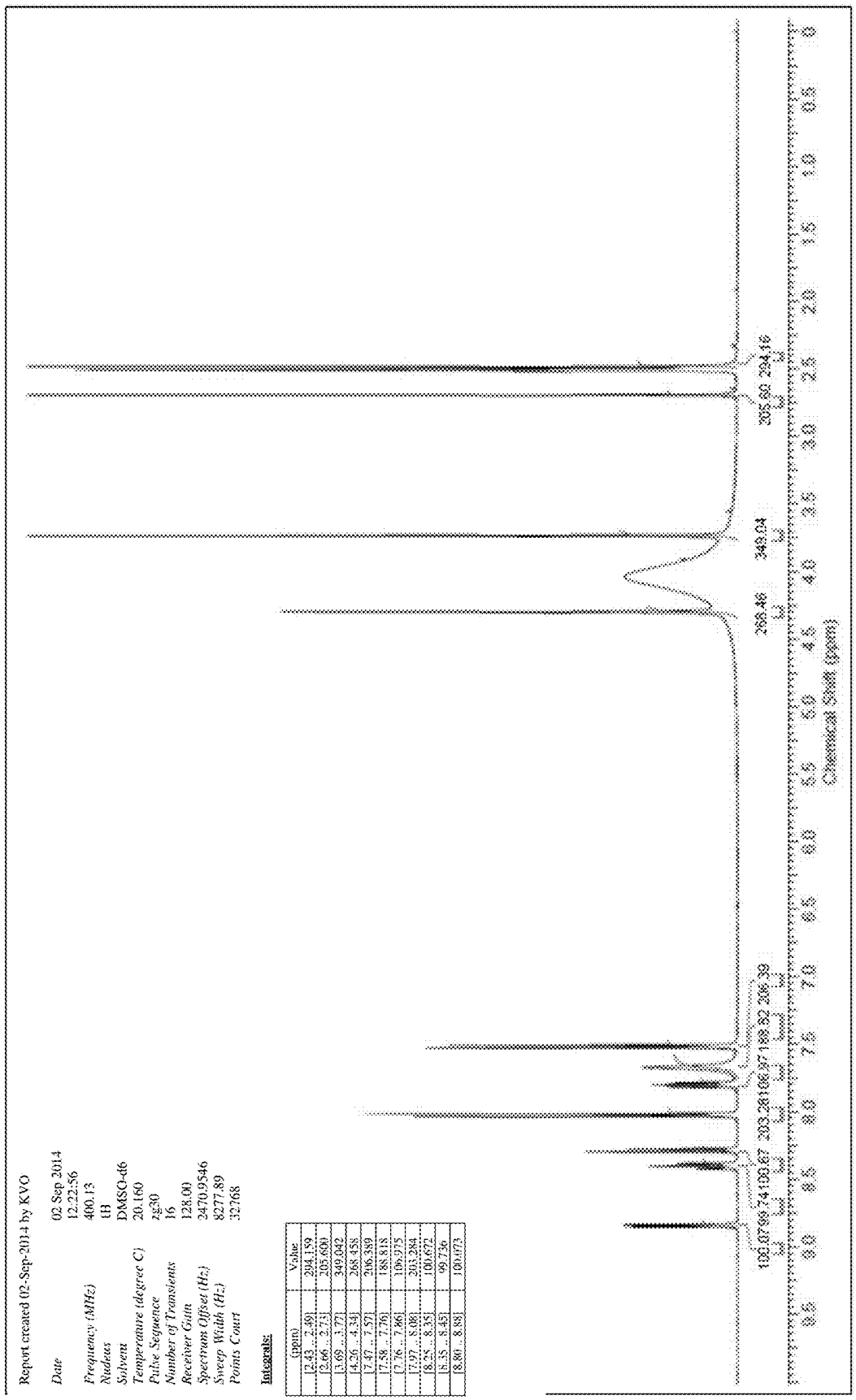
FIG. 28: $^1$H NMR spectrum of a hemiethane-1,2-disulfonate salt of the free base of pritelivir in accordance with the invention.
Figure 29:
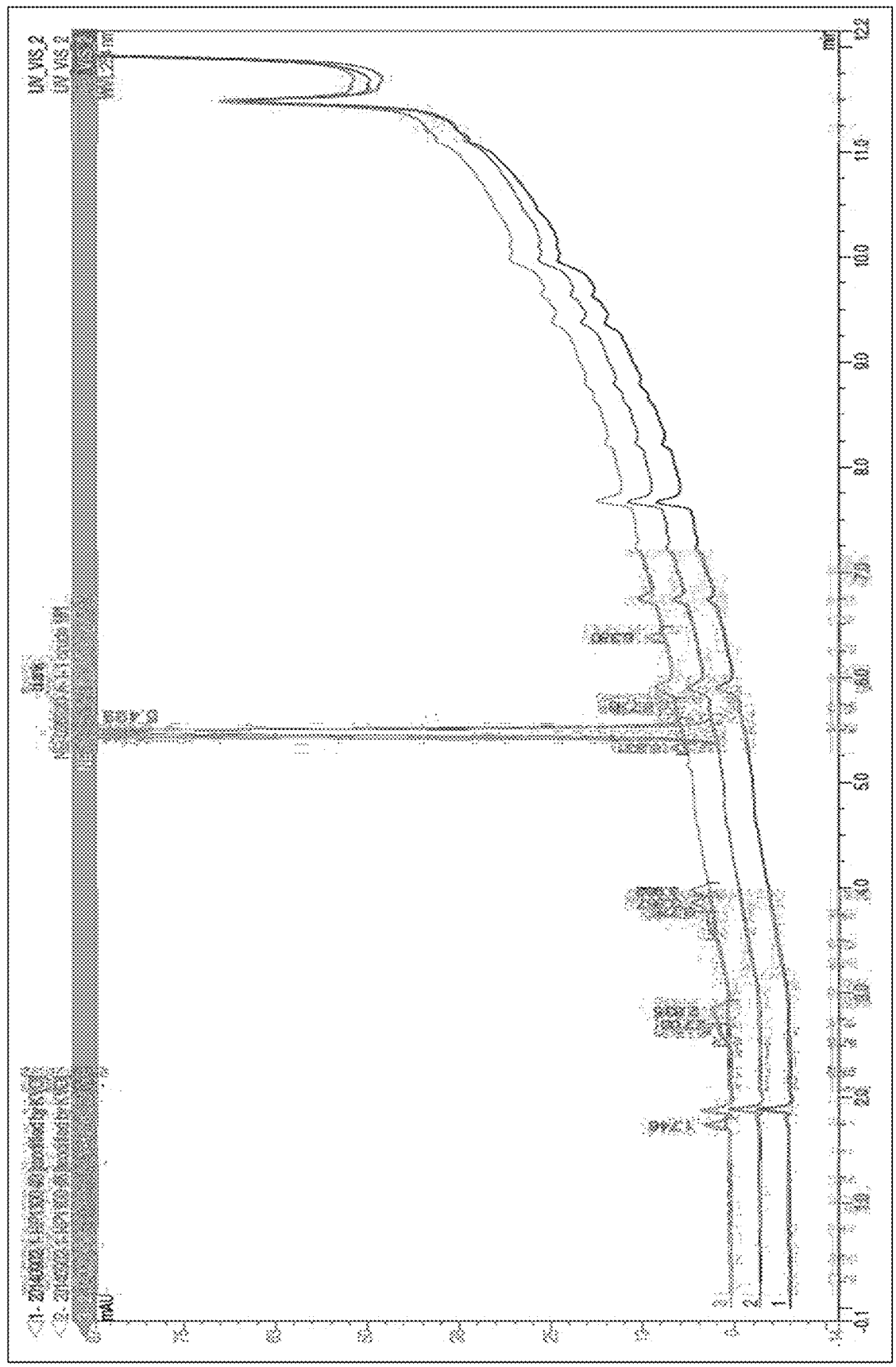
FIG. 29: HPLC overlay of a hemiethane-1,2-disulfonate salt of the free base of pritelivir in accordance with the invention (middle, 100.0% a/a) with corresponding mother liquor (top, 82.54% a/a) and blank (bottom).
Figure 30:
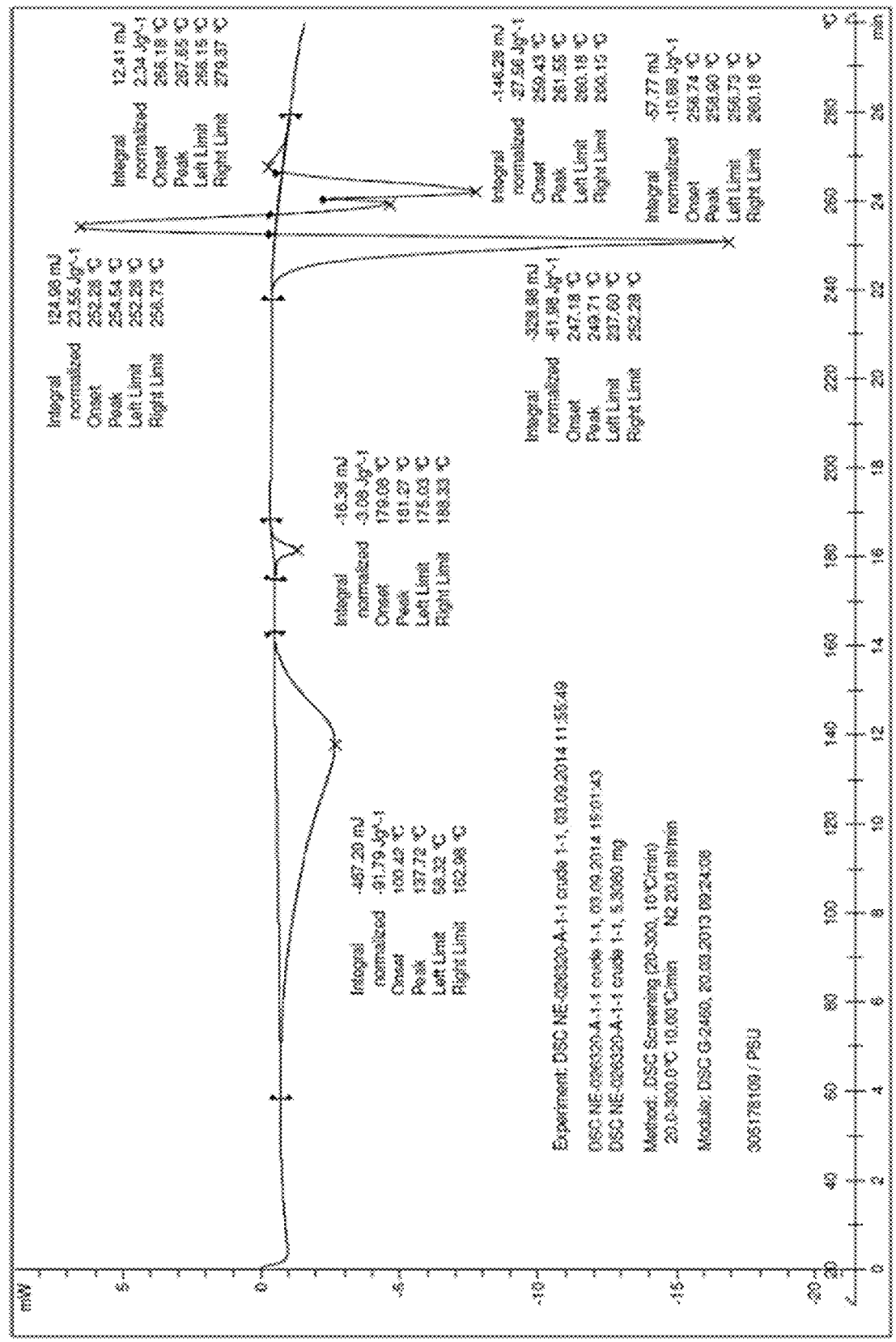
FIG. 30: DSC of a hemiethane-1,2-disulfonate salt of the free base of pritelivir in accordance with the invention. A large endothermicity due to water release (100° C. onset) as well as form conversion (180° C.) and melting endotherms (250° C.) are visible.
Figure 31:
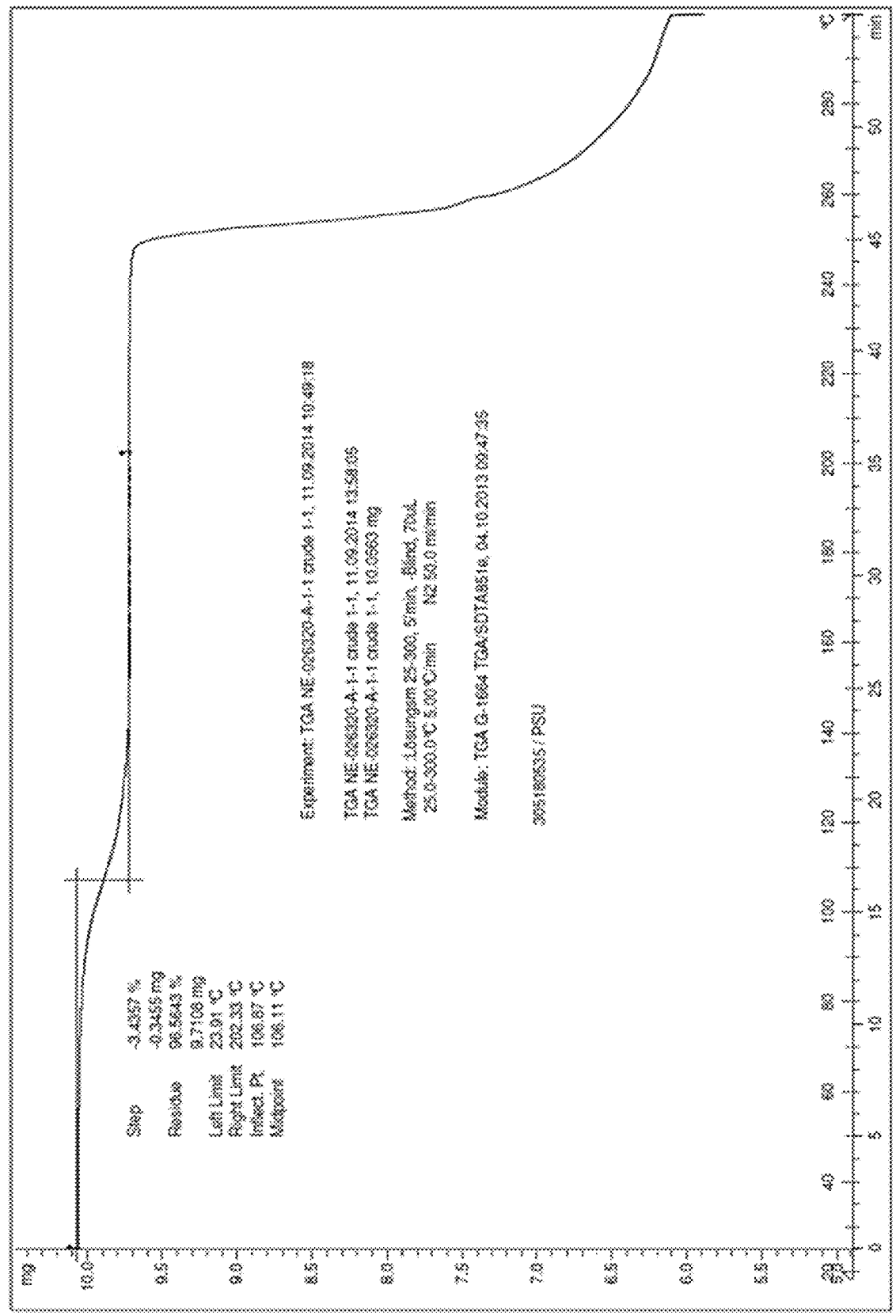
FIG. 31: TGA of a hemiethane-1,2-disulfonate salt of the free base of pritelivir in accordance with the invention with a weight loss of 3.4% w/w.
Figure 32:
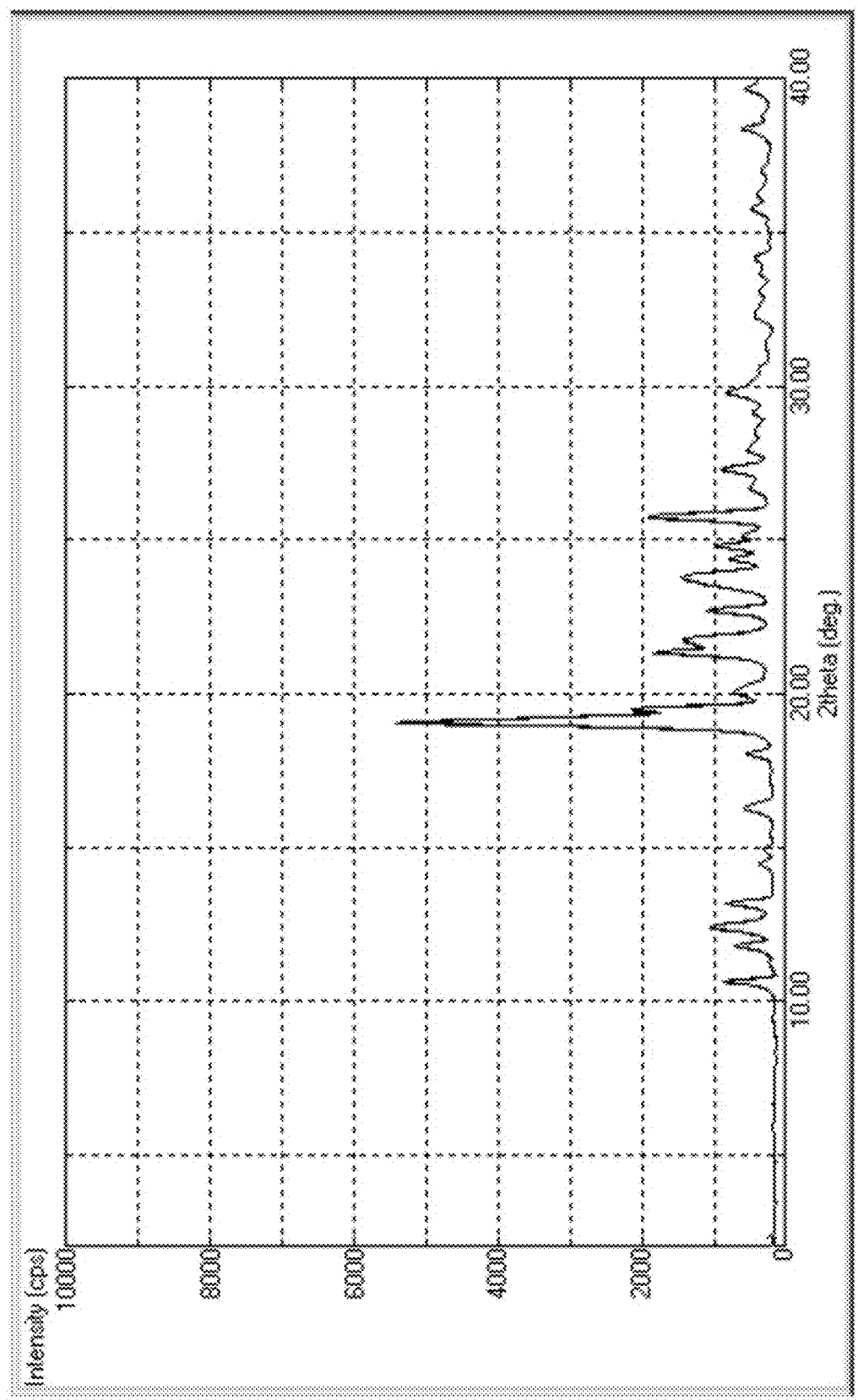
FIG. 32: XRPD of a hemiethane-1,2-disulfonate salt of the free base of pritelivir in accordance with the invention shows the crystalline form.
Figure 33:
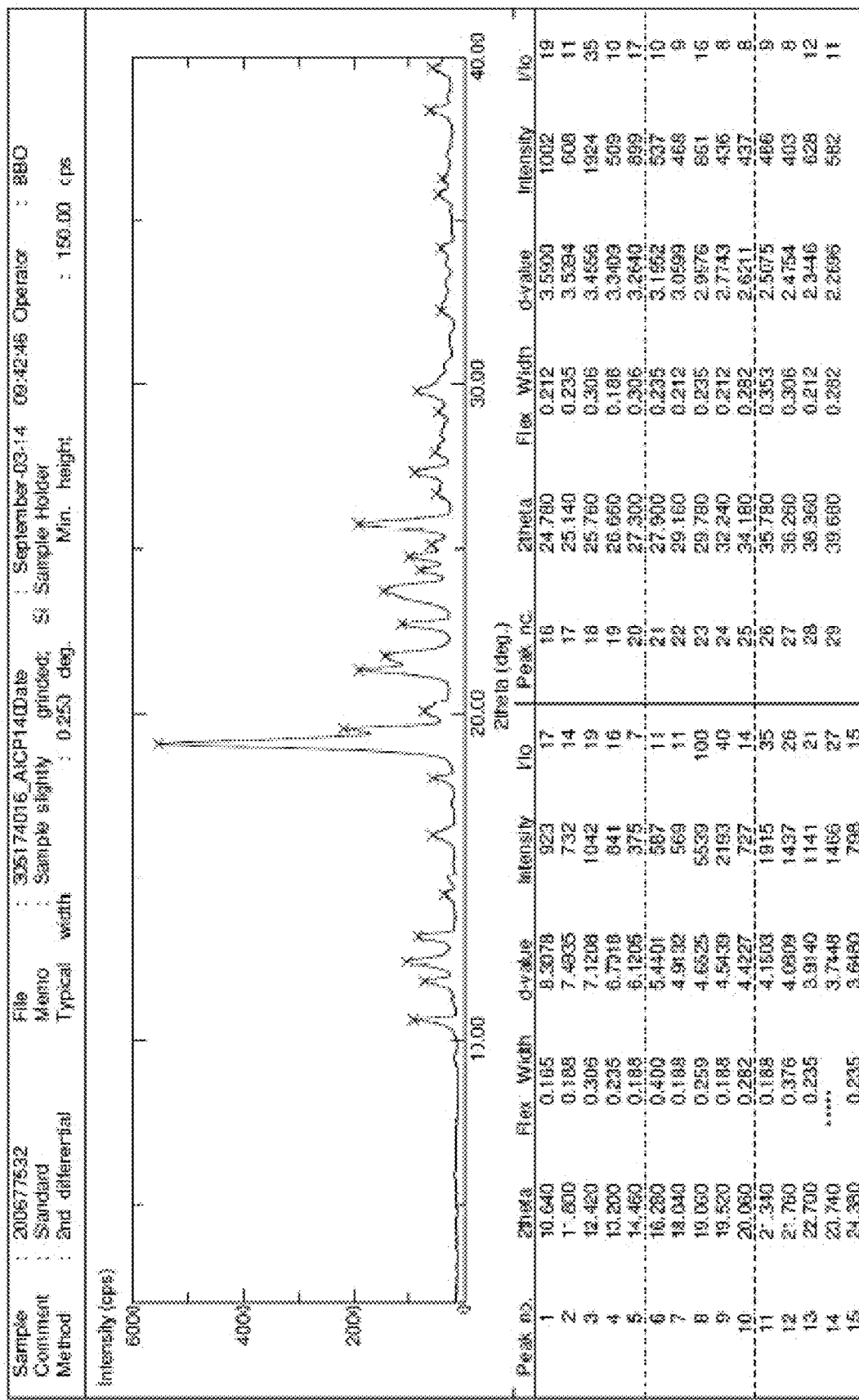
FIG. 33: XRPD data for a hemiethane-1,2-disulfonate salt of the free base of pritelivir in accordance with the invention.
Figure 34:
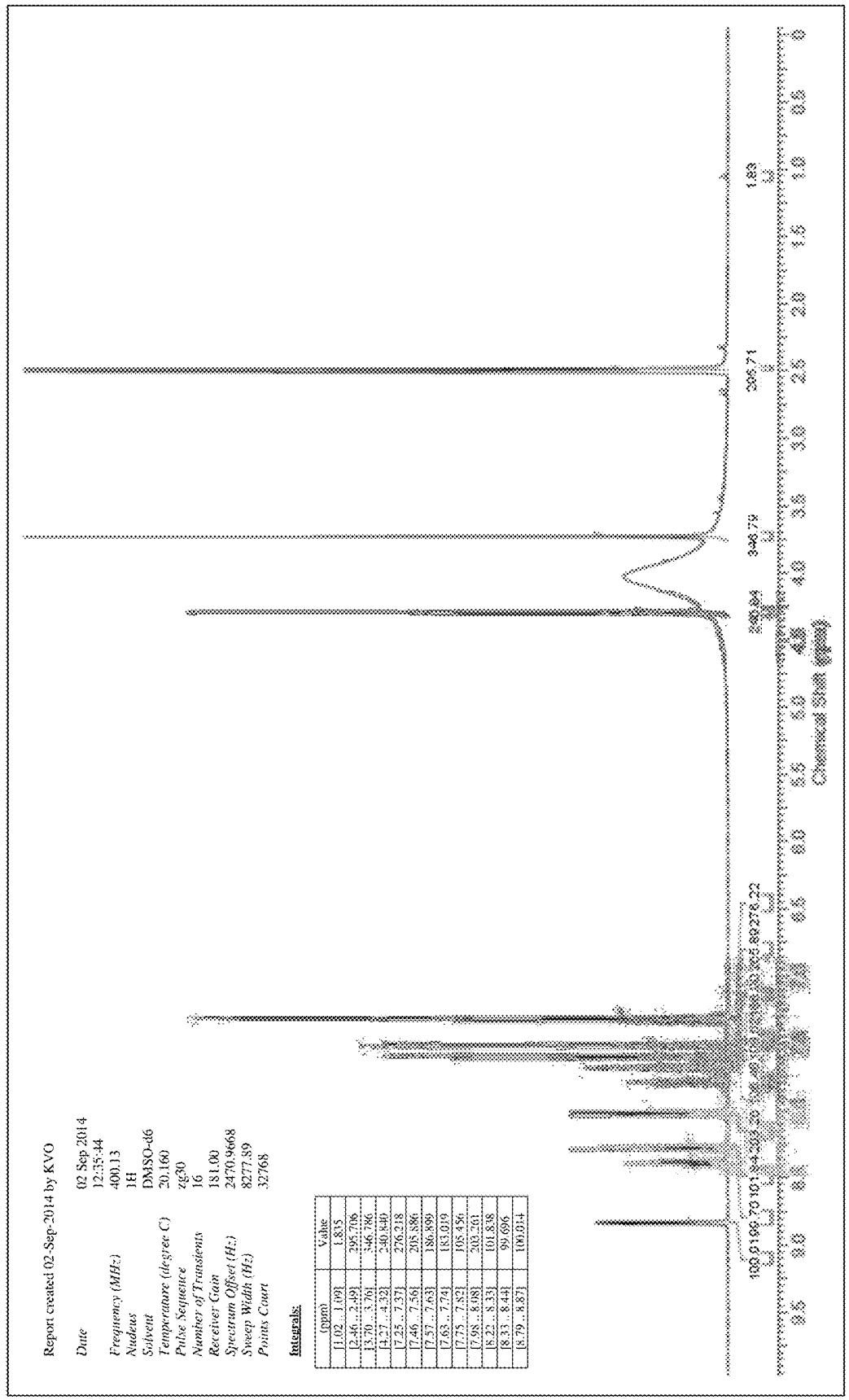
FIG. 34: $^1$H NMR spectrum of a benzenesulfonate salt of the free base of pritelivir in accordance with the invention.
Figure 35:
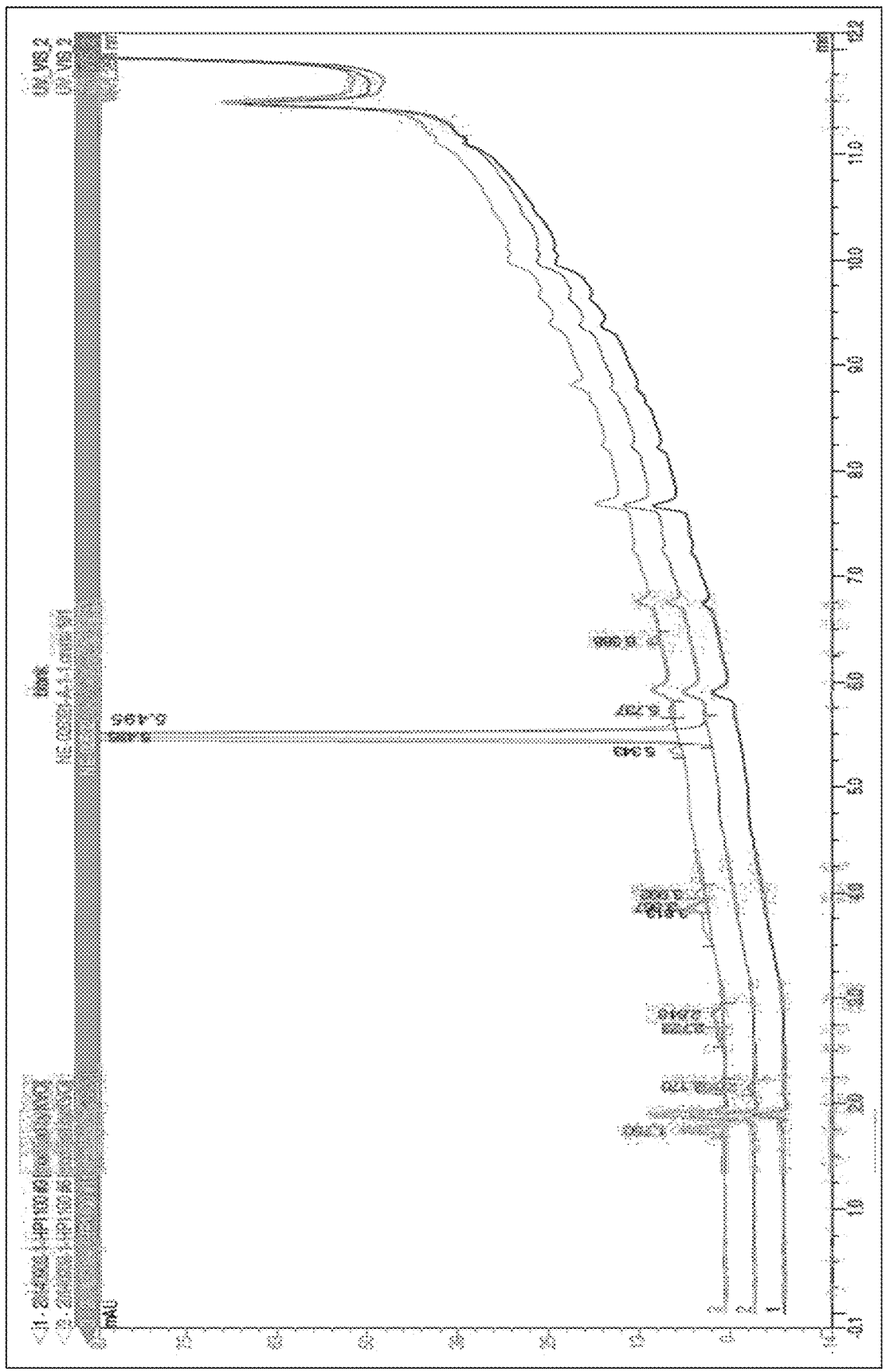
FIG. 35: HPLC overlay of a benzenesulfonate salt of the free base of pritelivir in accordance with the invention (middle, 99.64% a/a) with corresponding mother liquor (top, 83.88% a/a) and blank (bottom).
Figure 36:
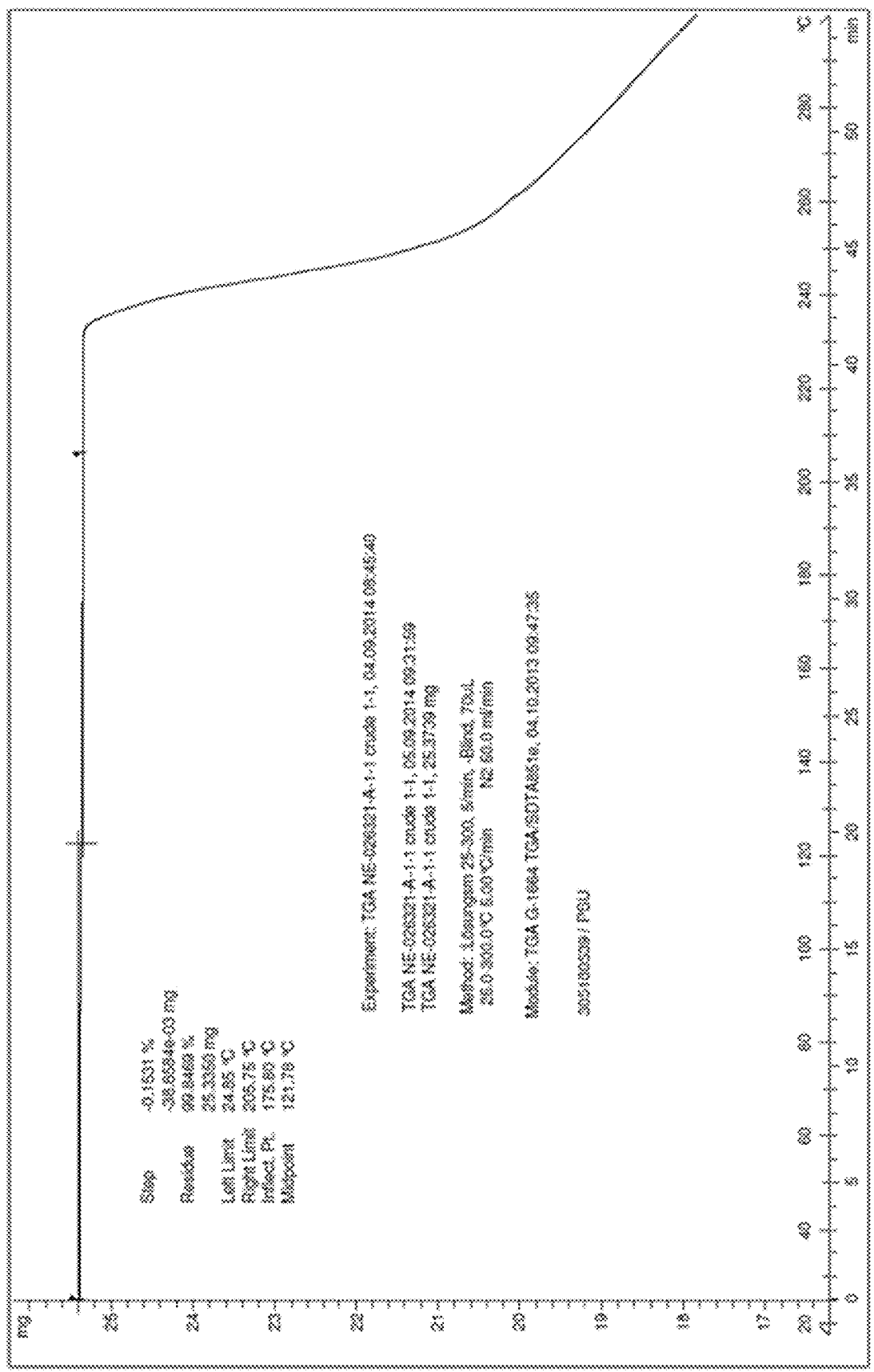
FIG. 36: TGA of a benzenesulfonate salt of the free base of pritelivir in accordance with the invention with a weight loss of 0.15% w/w.
Figure 37:
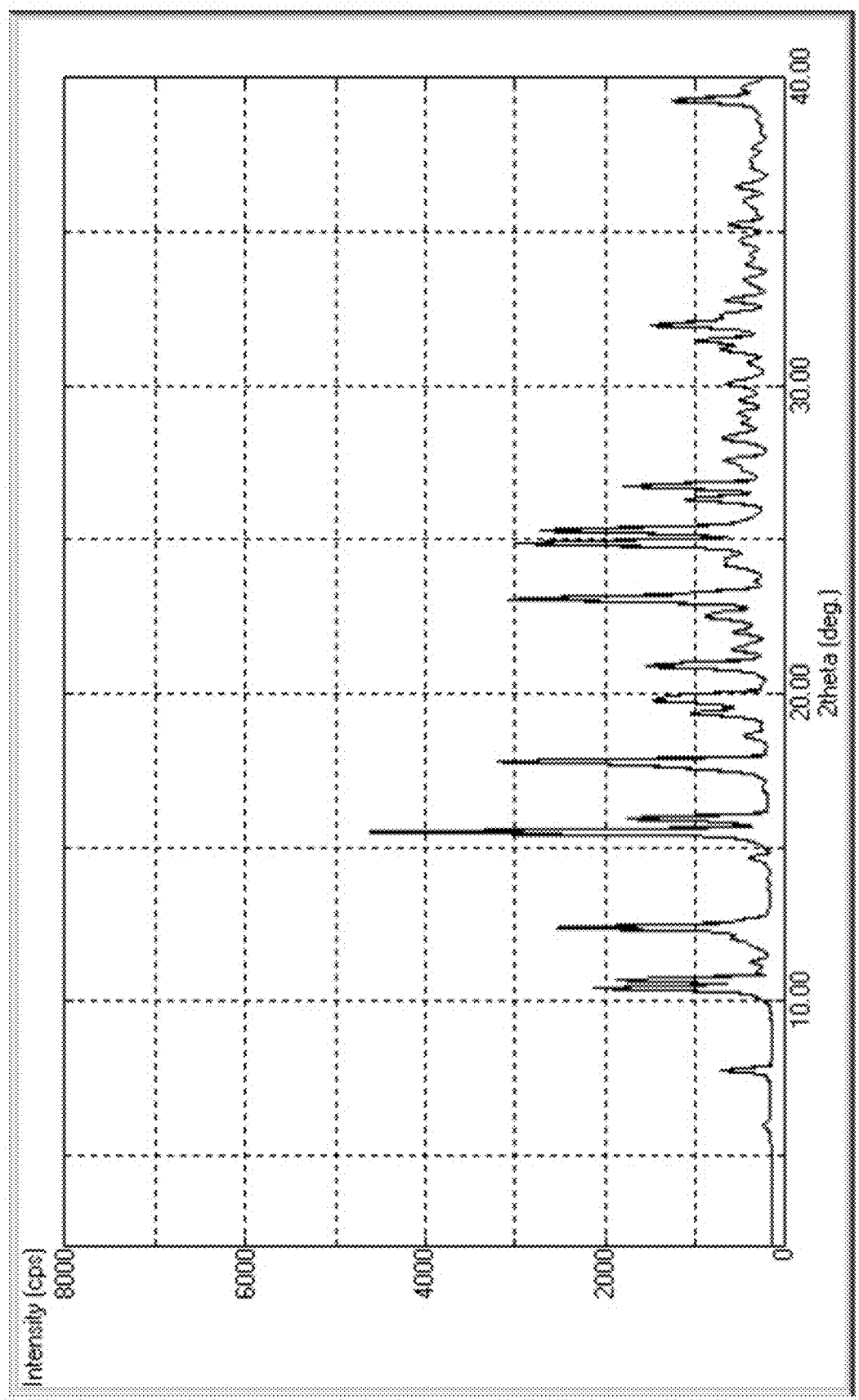
FIG. 37: XRPD of a benzenesulfonate salt of the free base of pritelivir in accordance with the invention shows a crystalline form.
Figure 38:
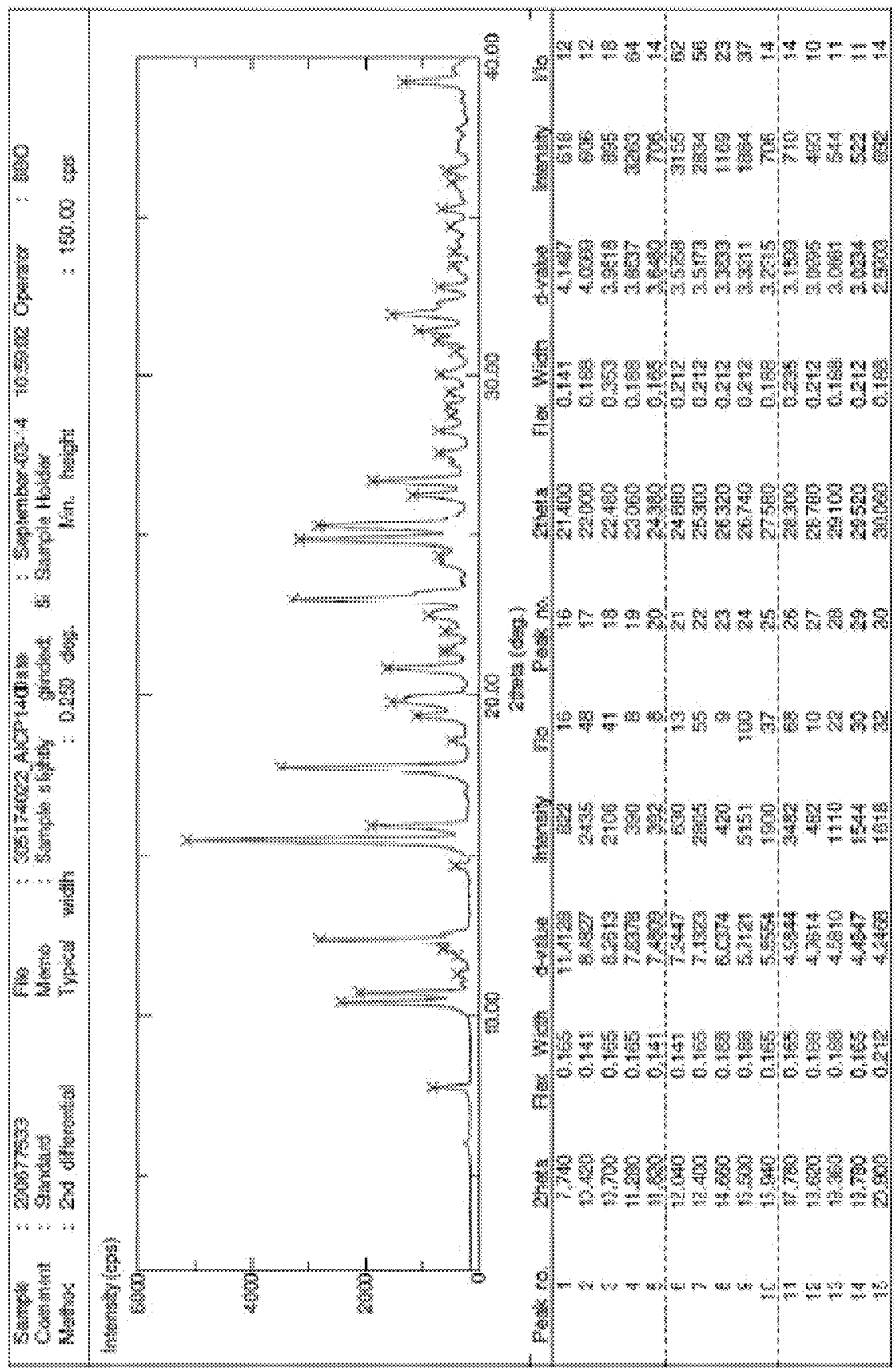
FIG. 38: XRPD data for a benzenesulfonate salt of the free base of pritelivir in accordance with the invention.
Figure 39:
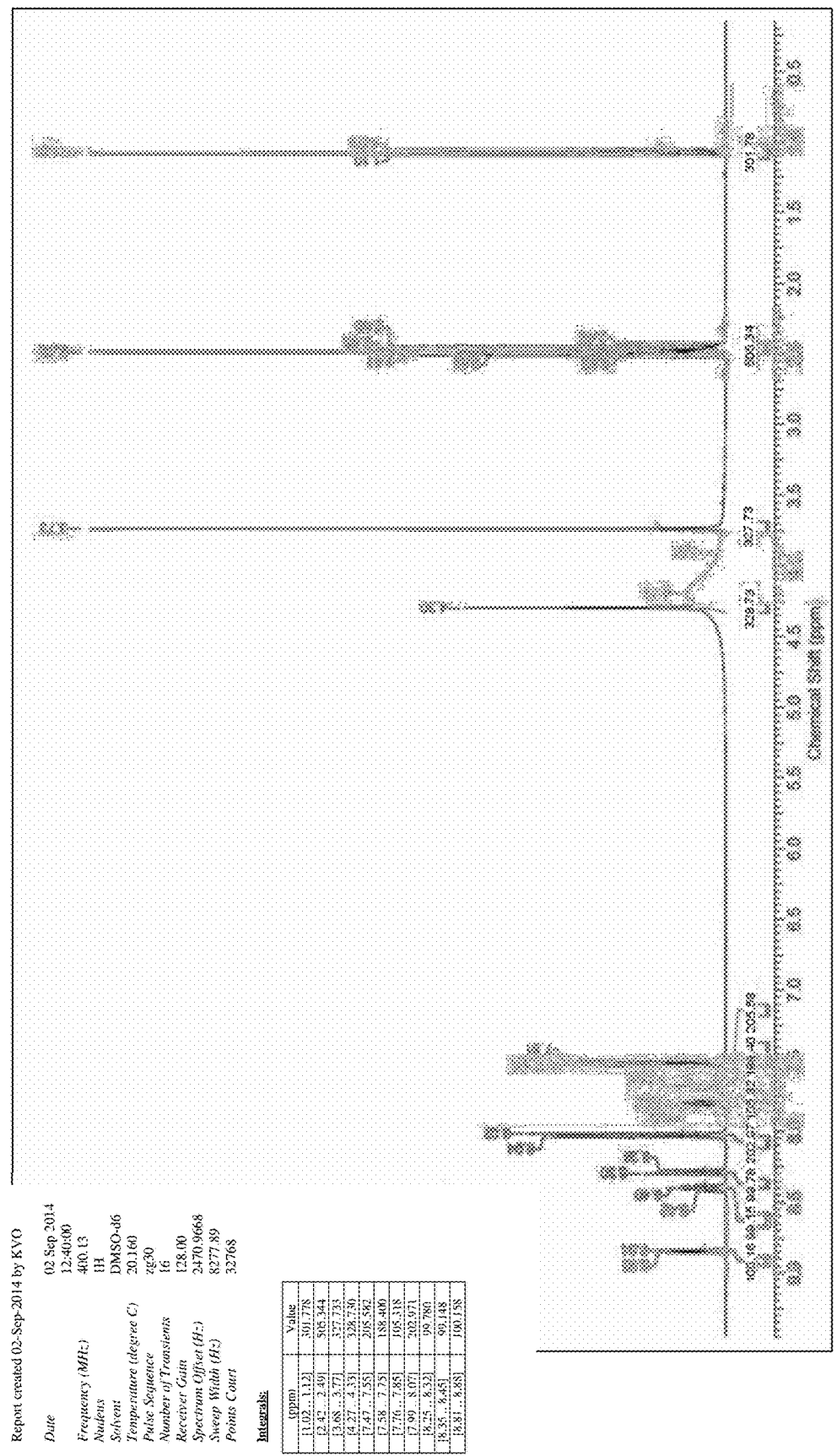
FIG. 39: $^1$H NMR spectrum of an esylate salt of the free base of pritelivir in accordance with the invention.
Figure 40:
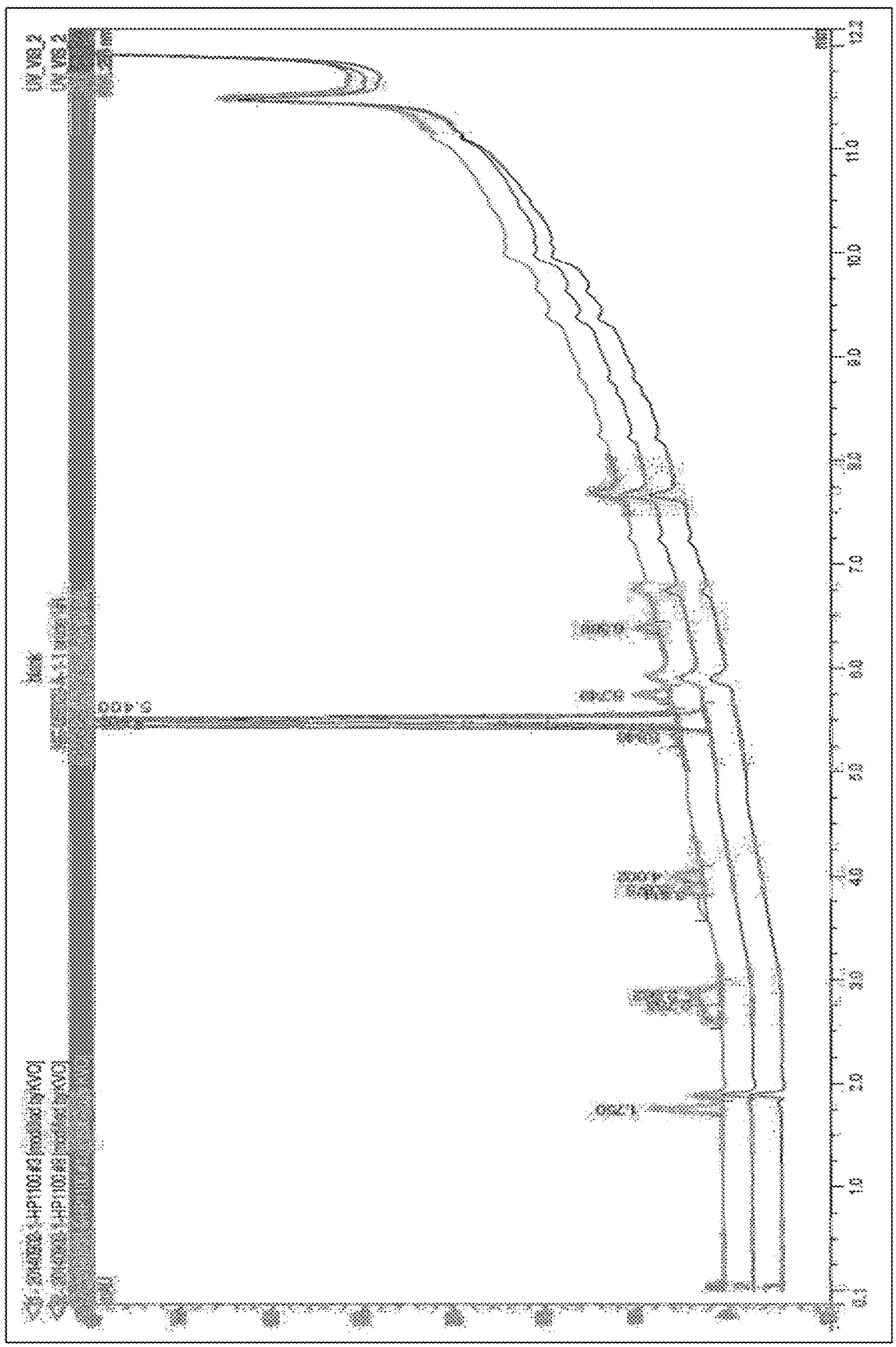
FIG. 40: HPLC overlay of an esylate salt of the free base of pritelivir in accordance with the invention (middle, 100.0% a/a); with corresponding mother liquor (top, 63.06% a/a) and blank (bottom).
Figure 41:
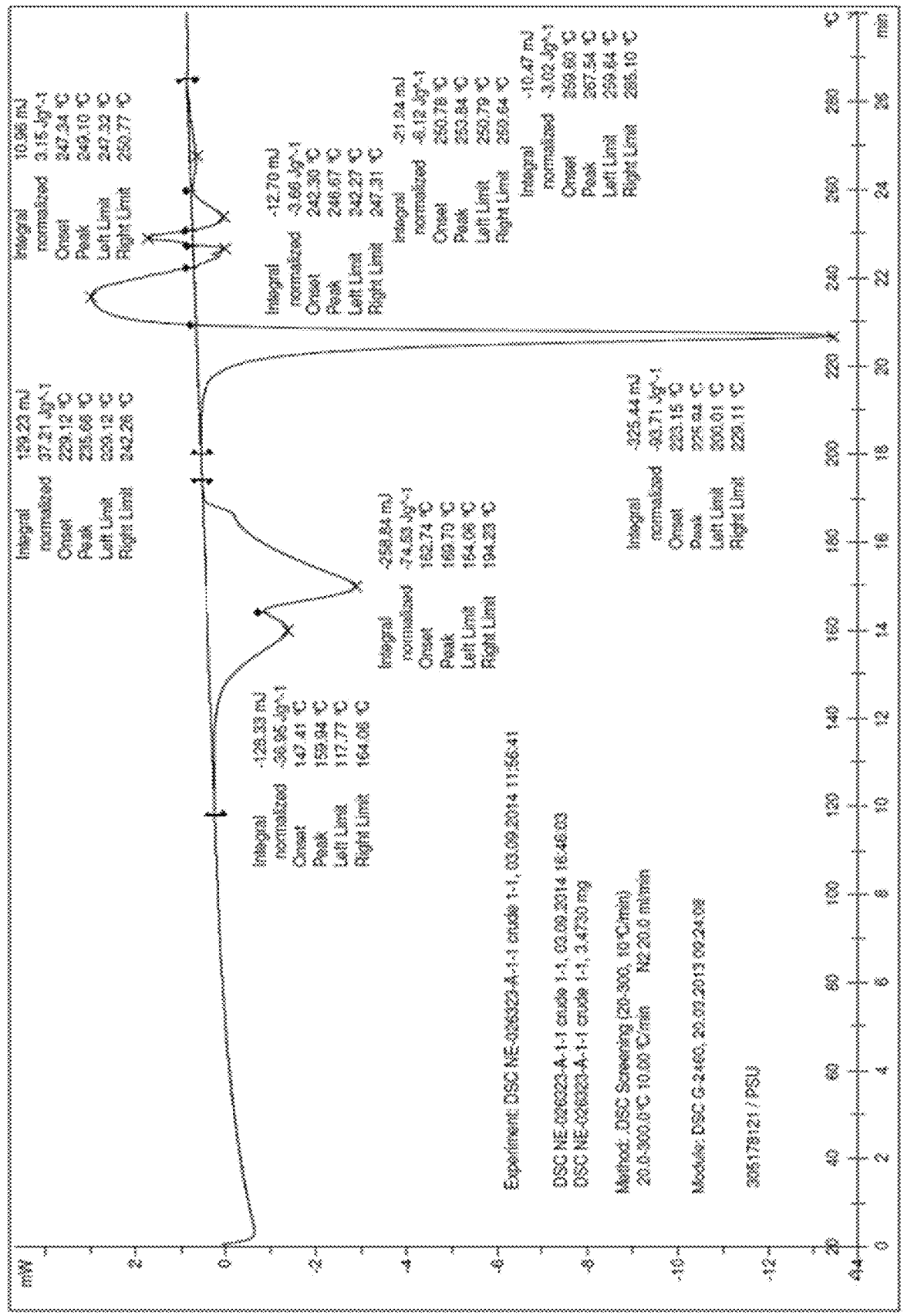
FIG. 41: DSC of an esylate salt of the free base of pritelivir in accordance with the invention. Water release/form conversion endothermicity around 150° C. and melting endotherm at 223° C.
Figure 42:
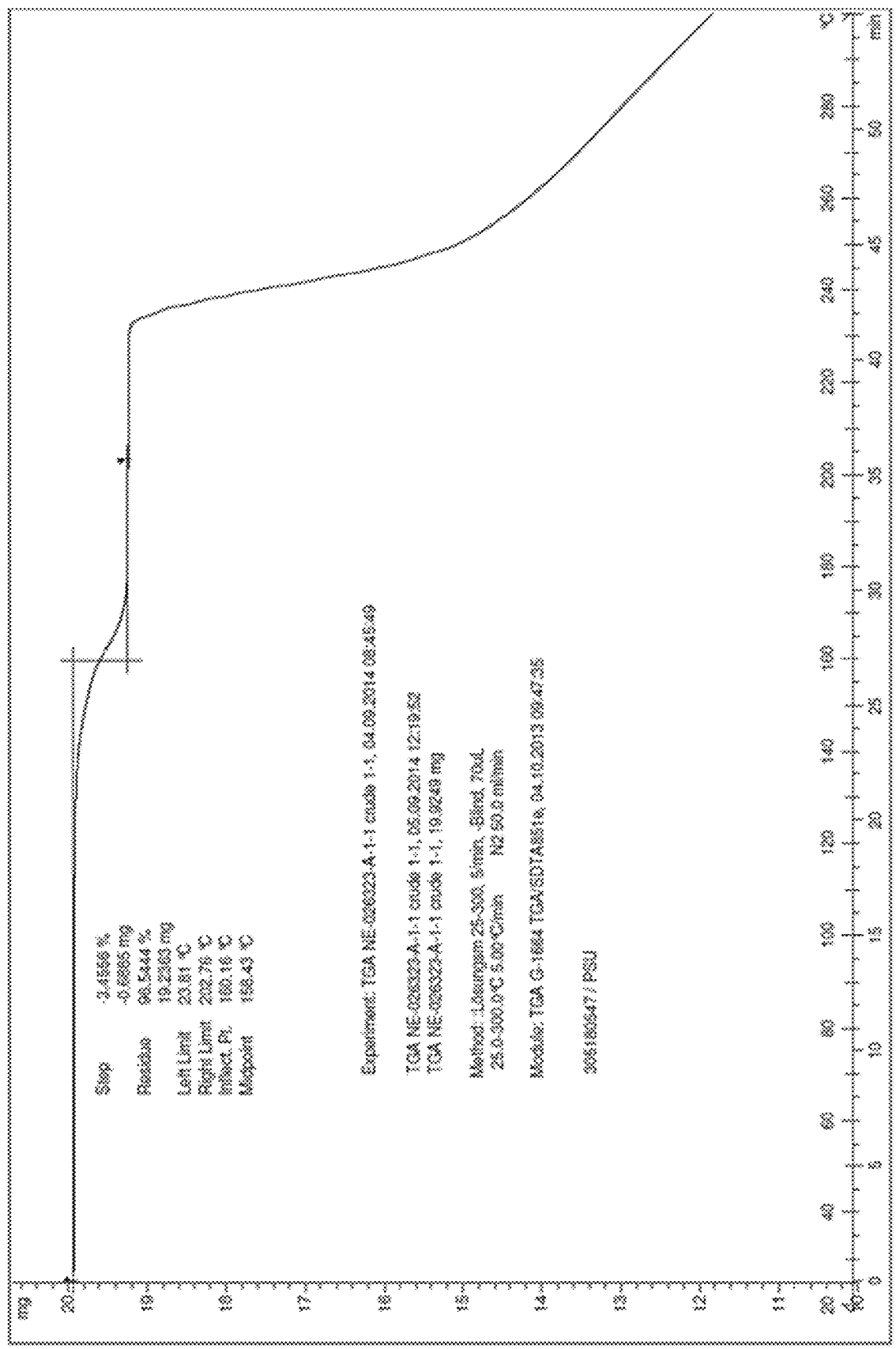
FIG. 42: TGA of an esylate salt of the free base of pritelivir in accordance with the invention with a weight loss of 3.5% w/w up to 200° C.
Figure 43:
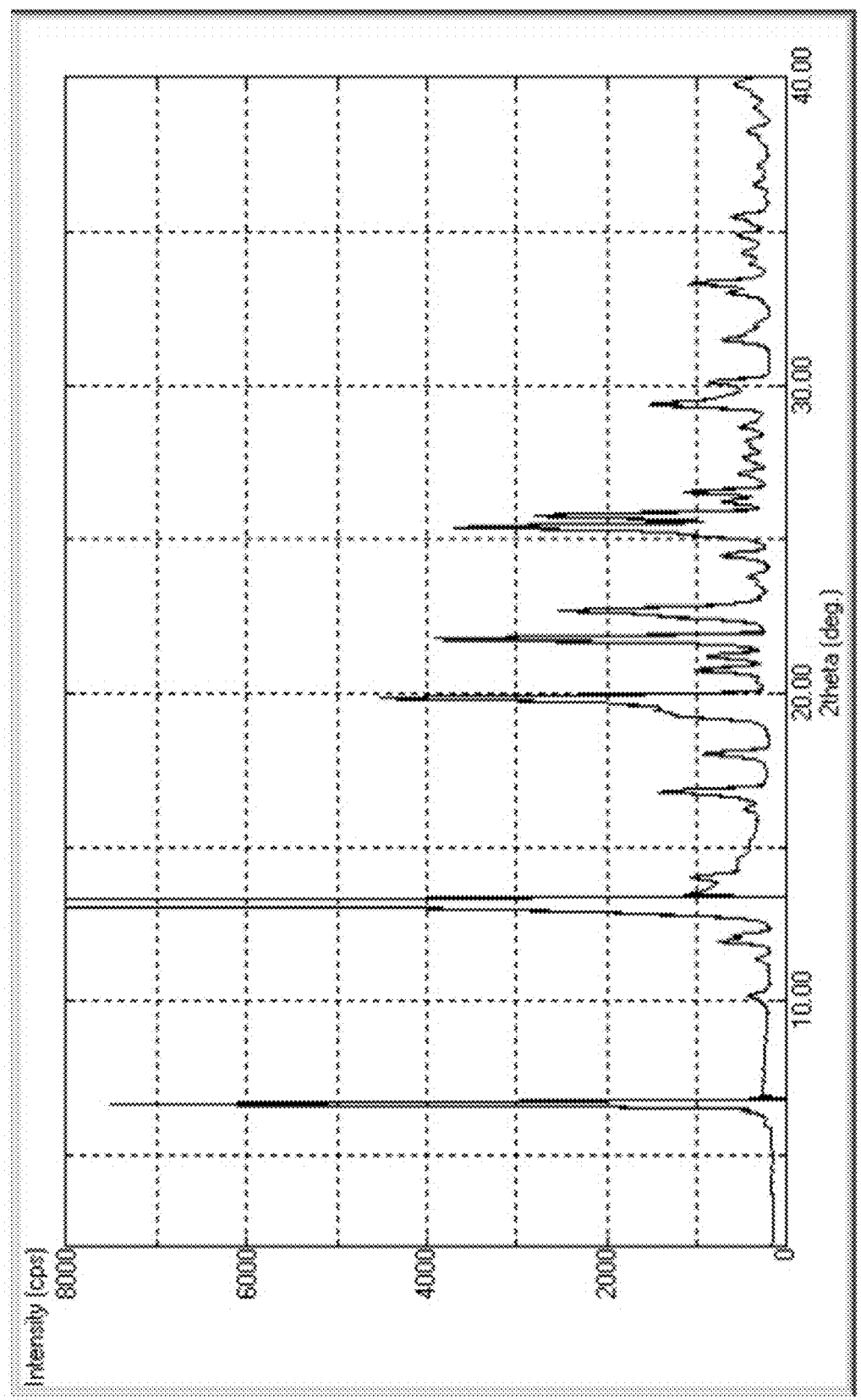
FIG. 43: XRPD of an esylate salt of the free base of pritelivir in accordance with the invention shows a crystalline form.
Figure 44:
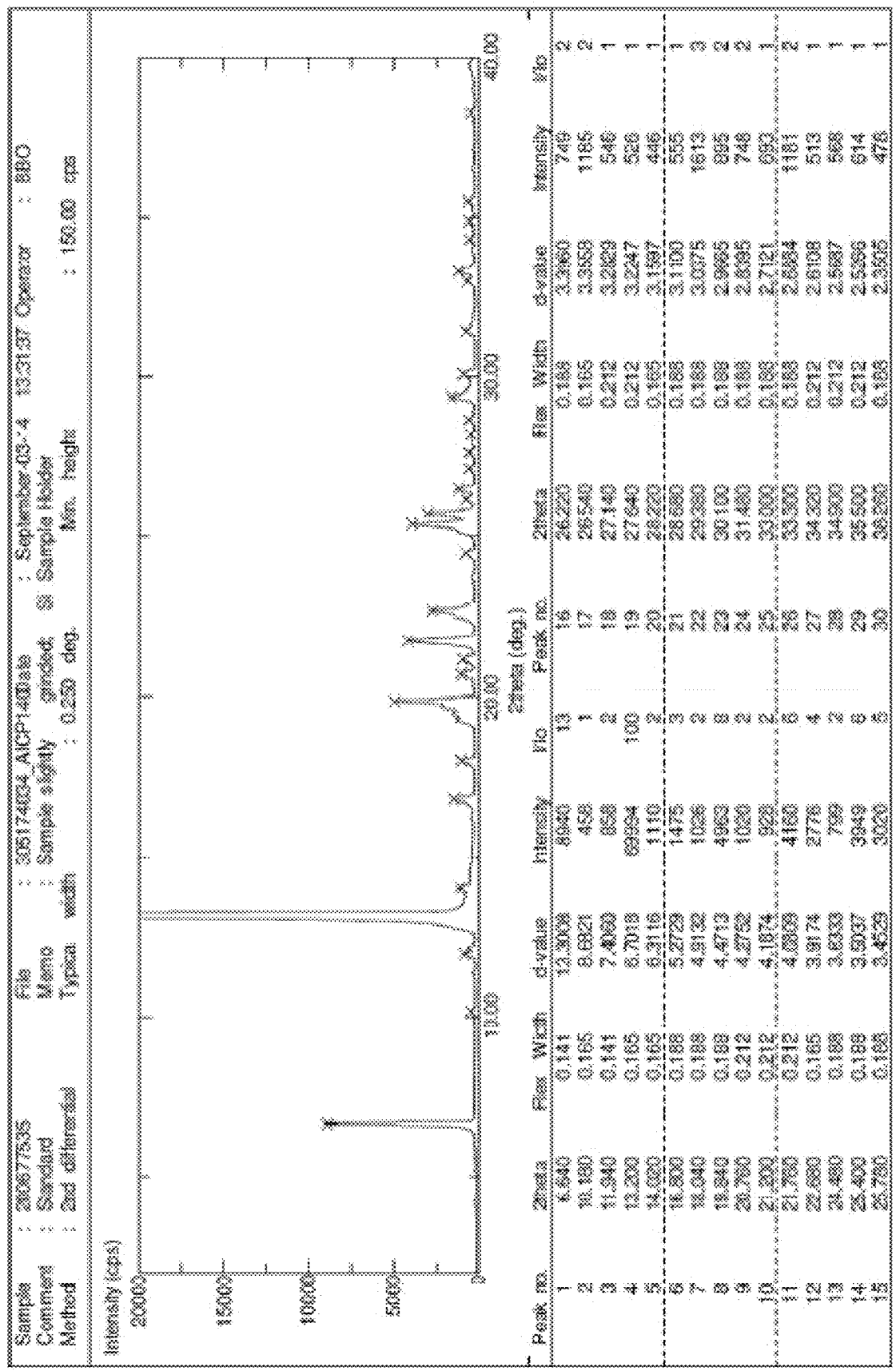
FIG. 44: XRPD data for an esylate salt of the free base of pritelivir in accordance with the invention.
Figure 45:
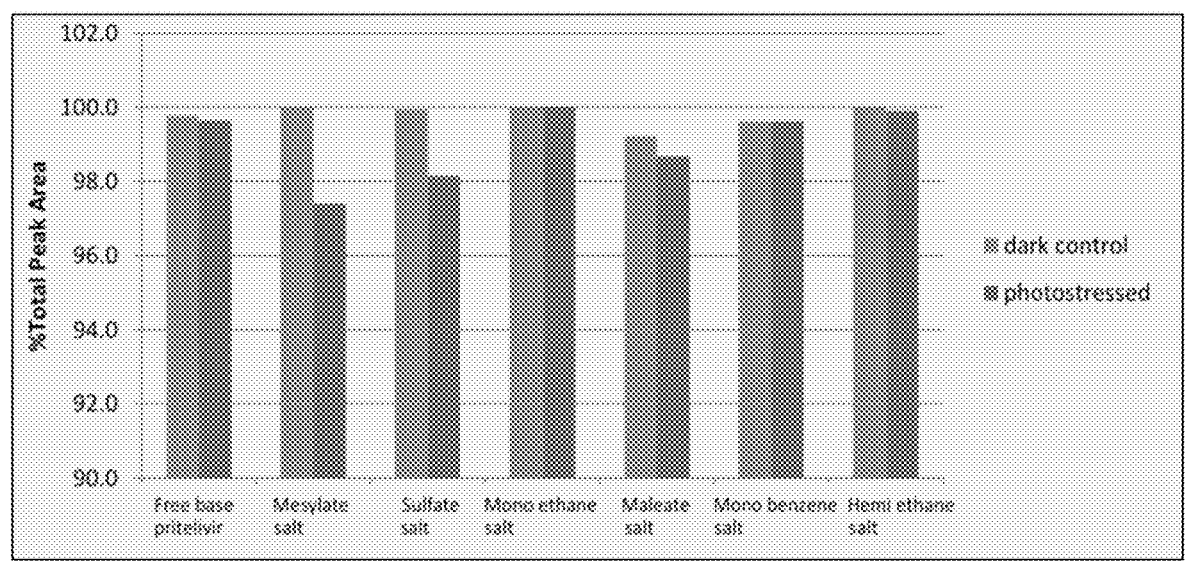
FIG. 45: Peak % area of irradiated solutions of the test items and dark control: free base of pritelivir, mesylate salt thereof, sulfonate salt thereof, maleate salt thereof, esylate salt thereof, mono benzenesulfonate thereof, hemi ethane-1,2,-disulfonate.
Figure 46:
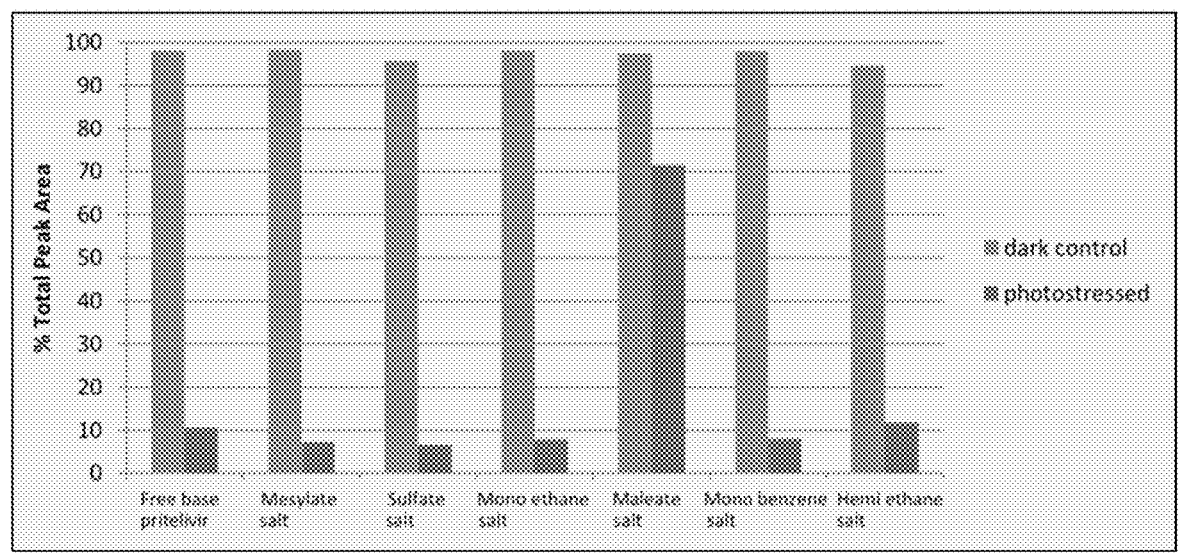
FIG. 46: Peak % area of irradiated solutions of the test items and dark control: free base of pritelivir, mesylate salt thereof, sulfonate salt thereof, maleate salt thereof, esylate salt thereof, mono benzenesulfonate thereof, hemi ethane-1,2,-disulfonate.

Mass spectra of a maleate salt of the free base of pritelivir are depicted in FIGS. 20 to 21.

Example V—Process of Manufacture

V.1 Exemplary Process for the Manufacture of the Maleate Salt of the Free Base of N-[5-(aminosulfonyl)-4-methyl-1,3-thiazol-2-yl]-N-methyl-2-[4-(2-pyridinyl)-phenyl]acetamide In the present example on the process for the manufacture of a maleate salt in accordance with the invention, all equivalents, volumes (given in L/kg) and weights (given in kg/kg) refer to the weight of the starting material free base of pritelivir. In a 5 L flask with overhead stirring the free base of pritelivir (1 eq., 1 wt., 475.4 g) was suspended in water (4.0 vol.) and ethanol (4.0 vol.). The suspension was heated to 51° C. Maleic acid (2.0 eq., 0.576 wt.) was added as solid during one hour. Towards the end of the acid addition the suspension almost completely dissolved and turned into a solution after the addition was finished. The solution was cooled to 48° C. and seeded (an aliquot of the solution was seeded with a crude maleate salt of free base of pritelivir). The suspension was allowed to cool down towards 21° C. (within approx. 2 hours) and was stirred overnight.

The suspension was filtered and the resultant filter cake was washed with a mixture of water (0.8 vol.) and ethanol (0.8 vol.). After deliquoring the filter cake on the filter, the solid was transferred to a flask and dried on a rotary evaporation device (Rotavapor®) (at temperature of 35° C., <20 mbar, over 28 hours) to constant mass. The resultant maleate salt material was homogenised with mortar and pestle.

V.2 Characterization of the Material Obtained in Example V.1

IPC: 99.26% dry mass (Ta 160° C.).

289.29 g crude maleate salt of free base of pritelivir (89.6% yield not corrected for assay).

Ethanol content measured by NMR: 1520 ppm.

Water content determined by Karl Fischer titration: 3.4% w/w (monohydrate 3.4% w/w).

Assay determined by NMR: 98.7% w/w as maleate/76.6% w/w as free base.

The invention claimed is:

1. A maleate salt of the free base of N-[5-(amino-sulfonyl)-4-methyl-1,3-thiazol-2-yl]-N-methyl-2-[4-(2-pyridinyl)phenyl]acetamide.

2. The maleate salt according to claim 1, wherein said maleate salt has a photostability of at least 70% residual free base of N-[5-(amino-sulfonyl)-4-methyl-1,3-thiazol-2-yl]-N-methyl-2-[4-(2-pyridinyl)phenyl]acetamide after light exposure with wavelengths ranging from 300 nm to 800 nm, and with a light exposure quantity of at least 1.2 million Lux hours, and with a light exposure energy of at least 200 Wh/m$^2$ over at least 29 hours, when said photostability is determined by using a compendial method as per "Ph. Eur" and/or "USP" methods.

3. The maleate salt according to claim 1, wherein said maleate salt has characteristic XRPD peaks at 6.6, 15.9, 16.2, 18.1, 20.5, 22.5, 26.1, and 28.6 2theta, when determined by using a compendial method as per "Ph. Eur" and/or "USP" methods.

4. The maleate salt according to claim 1, wherein said maleate salt is physico-chemical stable as characterised by recovery of said maleate salt of the start concentration of at least 85% after two weeks storage at room temperature and at a pH as of from 3.5-7.0 in aqueous solution, when determined by using a compendial method as per "Ph. Eur" and/or "USP" methods.

5. The maleate salt according to claim 1, wherein said maleate salt has solubility in water of about 0.48 mg/mL, when determined by using a compendial method as per "Ph. Eur" and/or "USP" methods.

6. A pharmaceutical composition comprising a maleate salt according to claim 1, wherein said pharmaceutical composition further comprises at least one pharmaceutically acceptable excipient.

7. A method for preparing the pharmaceutical composition of claim 6, which comprises formulating the maleate salt with at least one pharmaceutically acceptable excipient.

8. The pharmaceutical composition according to claim 6, further comprising another pharmaceutically active ingredient selected from the group consisting of anti-inflammatory agents, anti-viral agents, centrally and peripherally acting analgesics and local anesthetics.

9. The pharmaceutical composition according to claim 6, further comprising an ultraviolet radiation blocking agent selected from the group consisting of octisalate, titanium dioxide, zinc oxide, PABA, homosalate, trolamine salicylate, dioxybenzone, sulisobenzone, oxybenzone, avobenzone, ecasmule, meradimate, cinoxate, and octocrylene.

10. A topical pharmaceutical formulation comprising the maleate salt as defined in claim 1, and further comprising at least one pharmaceutically acceptable excipient suitable to provide the formulation in a form selected from the group consisting of: administration patches, creams, ointments, salves, gels, skin lotions, wax formulations, lipsticks, tonics, mousses, foams, films, emulsions, pastes, solutions, oils, and lipogels.

11. The topical pharmaceutical formulation as defined in claim 10, wherein the maleate salt has a mean percentage recovery of about 95 to 105% when measured according to ICH guideline Q1B.

12. The pharmaceutical composition as defined in claim 6, wherein the maleate salt is present in dissolved form in an amount of 0.1 to 10% w/w, when determined by using a compendial method as per "Ph. Eur" and/or "USP" methods.

13. The topical pharmaceutical formulation as defined in claim 10, wherein the maleate salt is present in an amount sufficient to reach a concentration of at least ≥10 nM in the epidermis and dermis of an individual after at least 1 hour of application to the individual subjected to a method of topical treatment with said composition, when determined by using a compendial method as per "Ph. Eur" and/or "USP" methods.

14. A method of treatment of herpes virus infections which comprises administering a maleate salt according to claim 1 to a patient.

15. A process for the manufacture of the maleate salt of the free base of N-[5-(amino-sulfonyl)-4-methyl-1,3-thiazol-2-yl]-N-methyl-2-[4-(2-pyridinyl)phenyl]acetamide (pritelivir) as defined in claim 1, said process comprising the steps of:
   i) providing a mixing means,
   ii) filling said mixing means of step i) with 460 to 490 g of the free base of pritelivir,
   iii) suspending the free base of pritelivir of step ii) with 3 to 5 volumes of water,
   iv) heating the suspension of step iii) to 45 to 55° C. by suitable heating means,
   v) adding 225 to 240 g of maleic acid in solid form over a time period of 40 to 90 min. until resultant solution is obtained,
   vi) cooling the solution obtained under step v) down to from 44 to 52° C.,
   vii) seeding an aliquot of the solution of step vi) with a maleate salt of the free base of pritelivir,
   viii) over a period of from 1.5 to 2.5 hours, allowing the resultant suspension of step vii) to cool down to from 18 to 24° C.,
   ix) stirring the suspension of step viii) overnight,
   x) filtering the suspension of step ix) to obtain a resultant filter cake,
   xi) transferring the solid filter cake obtained under step x) to a mixing means,
   xii) conducting rotary evaporation in the mixing means of step xi) for 25 to 32 hours while applying the following conditions:
      a. an ambient temperature of 30 to 40° C., and
      b. a pressure of 15 to 25 mbar,
      to obtain a mixture of constant mass,
   xiii) homogenizing the mixture of constant mass from step xii),
   to obtain the maleate salt of the free base of pritelivir.

* * * * *